US012703719B2

(12) United States Patent
Baba et al.

(10) Patent No.: US 12,703,719 B2
(45) Date of Patent: Aug. 11, 2026

(54) PRODUCTION OF BRIDGED ARTIFICIAL NUCLEOSIDES

(71) Applicants: NIPPON SHOKUBAI CO., LTD., Osaka (JP); OSAKA UNIVERSITY, Osaka (JP)

(72) Inventors: Takeshi Baba, Osaka (JP); Hiroshi Okamoto, Osaka (JP); Yumi Nomura, Osaka (JP); Satoshi Obika, Osaka (JP); Takao Yamaguchi, Osaka (JP)

(73) Assignees: NIPPON SHOKUBAI CO., LTD., Osaka (JP); OSAKA UNIVERSITY, Osaka (JP)

( * ) Notice: Subject to any disclaimer, the term of this patent is extended or adjusted under 35 U.S.C. 154(b) by 913 days.

(21) Appl. No.: 17/601,326

(22) PCT Filed: Mar. 31, 2020

(86) PCT No.: PCT/JP2020/014764

§ 371 (c)(1), (2) Date: Oct. 4, 2021

(87) PCT Pub. No.: WO2020/204022

PCT Pub. Date: Oct. 8, 2020

(65) Prior Publication Data

US 2022/0177509 A1 Jun. 9, 2022

(30) Foreign Application Priority Data

Apr. 5, 2019 (JP) ................................ 2019-073073

(51) Int. Cl.
*C07H 19/16* (2006.01)
*C07H 1/00* (2006.01)
*C07H 19/06* (2006.01)

(52) U.S. Cl.
CPC ............... *C07H 19/16* (2013.01); *C07H 1/00* (2013.01); *C07H 19/06* (2013.01)

(58) Field of Classification Search
CPC ................................ C07H 19/16; C07H 19/06
See application file for complete search history.

(56) References Cited

U.S. PATENT DOCUMENTS

| | | | |
|---|---|---|---|
| 6,291,670 B1 | 9/2001 | Ohrui et al. | |
| 6,333,315 B1 | 12/2001 | Ohrui et al. | |
| 2002/0022722 A1 | 2/2002 | Ohrui et al. | |
| 2003/0236216 A1 | 12/2003 | Devos et al. | |
| 2004/0266722 A1 | 12/2004 | Devos et al. | |
| 2007/0042988 A1 | 2/2007 | Klumpp et al. | |
| 2010/0003213 A1 | 1/2010 | Devos et al. | |
| 2010/0004192 A1 | 1/2010 | Martin et al. | |
| 2011/0053881 A1 | 3/2011 | Seth et al. | |
| 2012/0034184 A1 | 2/2012 | Devos et al. | |
| 2013/0237491 A1 | 9/2013 | Devos et al. | |
| 2015/0366888 A1 | 12/2015 | Blatt et al. | |
| 2015/0368287 A1* | 12/2015 | Mitsuoka | C07H 19/06 536/28.54 |
| 2016/0220595 A1 | 8/2016 | Liotta et al. | |
| 2016/0244501 A1 | 8/2016 | Ellsworth et al. | |
| 2017/0044528 A1 | 2/2017 | Obika et al. | |
| 2017/0143749 A1 | 5/2017 | Blatt et al. | |
| 2019/0248864 A1 | 8/2019 | Ellsworth et al. | |
| 2019/0298750 A1 | 10/2019 | Liotta et al. | |
| 2020/0157138 A1 | 5/2020 | Zhang et al. | |
| 2021/0060051 A1 | 3/2021 | Schinazi et al. | |

FOREIGN PATENT DOCUMENTS

| | | |
|---|---|---|
| CN | 101796062 | 8/2010 |
| CN | 109893536 | 6/2019 |
| JP | 2001-335592 | 12/2001 |
| JP | 2001-335593 | 12/2001 |
| JP | 2004-536817 | 12/2004 |
| JP | 2009-504704 | 2/2009 |
| JP | 2015-151346 | 8/2015 |
| JP | 2016-530313 | 9/2016 |

(Continued)

OTHER PUBLICATIONS

Nomura, J. Med. Chem. 1999, 42, 2901-2908. (Year: 1999).*
International Search Report (ISR) issued Jun. 30, 2020 in International (PCT) Application No. PCT/JP2020/014764.
Yasunori Mitsuoka et al., "Triazole- and Tetrazole-Bridged Nucleic Acids: Synthesis, Duplex Stability, Nuclease Resistance, and in Vitro and in Vivo Antisense Potency", The Journal of Organic Chemistry, 82(1), pp. 12-24, 2017.
Ei-ichi Kodama et al., "4'-Ethynyl Nucleoside Analogs: Potent Inhibitors of Multidrug-Resistant Human Immunodeficiency Virus Variants In Vitro", Antimicrobial Agents and Chemotherapy, vol. 45, No. 5, pp. 1539-1546, 2001.
Hiroshi Ohrui et al., "Syntheses of 4'-C-Ethynyl-β-D-arabino- and 4'-C-Ethynyl-2'-deoxy-β-D-ribo-Pentofuranosylpyrimidines and -purines and Evaluation of Their Anti-HIV Activity", Journal of Medicinal Chemistry, 43(23), pp. 4516-4525, 2000.

(Continued)

*Primary Examiner* — Layla D Berry
(74) *Attorney, Agent, or Firm* — Wenderoth, Lind & Ponack, L.L.P.

(57) ABSTRACT

Provided is a method for producing a compound represented by formula (III) from a compound represented by formula (I) as a starting material.

(I)

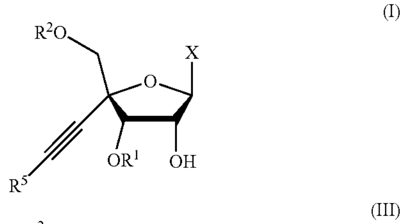

(III)

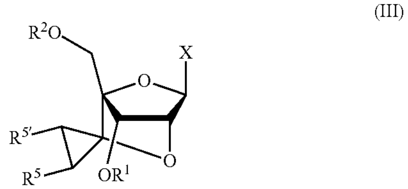

15 Claims, No Drawings

(56) References Cited

FOREIGN PATENT DOCUMENTS

| | | |
|---|---|---|
| JP | 2016-538829 | 12/2016 |
| JP | 2017-519784 | 7/2017 |
| WO | 02/100415 | 12/2002 |
| WO | 2009/006478 | 1/2009 |
| WO | 2014/126229 | 8/2014 |
| WO | 2015/125783 | 8/2015 |
| WO | 2016/145142 | 9/2016 |
| WO | 2018/227168 | 12/2018 |
| WO | 2019/133712 | 7/2019 |

OTHER PUBLICATIONS

Satoru Kohgo et al., "Synthesis of 4'-substituted nucleosides and their biological evaluation", Nucleic Acids Symposium Series, No. 42, pp. 127-128, 1999.

Satoru Kohgo et al., "Synthesis of 4'-C-Ethynyl-B-D-arabino- and 4'-C-Ethyny1-2'-deoxy-β-D-ribo-pentofuranosyl. Pyrimidines, and Their Biological Evaluation", Bioscience, Biotechnology and Biochemistry, 63(6), pp. 1146-1149, 1999.

Ritsuko Yamaguchi et al., "Synthesis of 4'-C-Ethyny1-β-D-ribo-pentofuranosyl Pyrimidines", Bioscience, Biotechnology and Biochemistry, 63(4), pp. 736-742, 1999.

Kei Fukuyama et al., "Synthesis of EFdA via a Diastereoselective Aldol Reaction of a Protected 3-Keto Furanose", Organic Letters, 17(4), pp. 828-831, 2015.

Hiroshi Ohrui, "4'-C-Ethyny1-2'-Deoxynucleosides, Modified Nucleosides", Biochemistry, Biotechnology and Medicine, pp. 425-431, 2008.

David B. Smith, et al., "Design, synthesis, and antiviral properties of 4'-substituted ribonucleosides as inhibitors of hepatitis C virus replication: The discovery of R1479", Bioorganic & Medicinal Chemistry Letters, 17(9), pp. 2570-2576, 2007.

Makoto Nomura et al., "Nucleosides and Nucleotides, 185, Synthesis and Biological Activities of 4'a-C-Branched-Chain Sugar Pyrimidine Nucleosides", Journal of Medicinal Chemistry. 42(15), pp. 2901-2908, 1999.

Jacob Werth et al., "Regioselective Simmons-Smith-type cyclopropanations of polyalkenes enabled by transition metal catalysis", Chemical Science, 9, pp. 1604-1609, 2018.

Takao Yamaguchi et al., "Synthesis and properties of 2'-O,4'-C-spirocyclo-propylene bridged nucleic acid (scpBNA), an analogue of 2',4'-BNA/LNA bearing a cyclopropane ring", ChemComm Communication, 51, pp. 9737-9740, 2015.

Masahiko Horiba et al., "Synthesis of scpBNA-$^{m}$C,-A, and -G Monomers and Evaluation of the Binding Affinities of scpBNA-Modified Oligonucleoties toward Complementary ssRNA and ssDNA", The Journal of Organic Chemistry, 81, pp. 11000-11008, 2016.

International Preliminary Report on Patentability and Written Opinion of the International Searching Authority issued Sep. 28, 2021 in International (PCT) Application No. PCT/JP2020/014764.

Extended European Search Report issued Dec. 5, 2022 in corresponding European Patent Application No. 20784778.1.

Michal Rachwalski et al., "Highly Efficient Asymmetric Simmons-Smith Cyclopropanation Promoted by Chiral Heteroorganic Aziridinyl Ligands", ChemCatChem, vol. 6, pp. 873-875, 2014.

Lorenz et al., "A Novel Class of Tunable Zinc Reagents ($RXZnCH_2Y$) for Efficient Cyclopropanation of Olefins", Journal of Organic Chemistry, 2004, vol. 69, No. 2, pp. 327-334.

* cited by examiner

PRODUCTION OF BRIDGED ARTIFICIAL NUCLEOSIDES

TECHNICAL FIELD

The present invention relates to a method for producing a spirocyclopropylene bridged nucleic acid (scpBNA). In particular, the present invention relates to a method for producing a nucleoside of a scpBNA, a compound used in the production method, and a compound produced by the production method.

BACKGROUND ART

Nucleic acid medicines have recently attracted attention and expected to serve as molecular species for drug discovery for new medicines. Naturally occurring nucleic acids are hydrolyzed by an enzyme in a living body. In order to address this and other problems, various types of modified nucleic acids have been investigated. For example, scpBNAs have high binding affinity for a single-stranded RNA, and are highly stable in a living body (see Patent literature 1 and non-patent literatures 1 and 2).

CITATION LIST

Patent Literature

Patent literature 1: WO 2015/125783

Non-Patent Literature

Non-patent literature 1: Chem. Commun., 2015, Vol. 51, 9737-9740.

Non-patent literature 2: J. Org. Chem., 2016, Vol. 81, 11000-11008.

SUMMARY OF INVENTION

Technical Problem

Conventional production methods for scpBNAs require multistage steps and need to be improved to achieve large-scale synthesis.

An object of the present invention is to provide a novel method for producing a spirocyclopropylene bridged nucleic acid (scpBNA) and a precursor thereof.

Another object of the present invention is to provide an efficient method for producing a spirocyclopropylene bridged nucleic acid (scpBNA) and a precursor thereof.

Another object of the present invention is to provide a compound that can be used in the production method, and a production method for the compound.

Solution to Problem

The inventors conducted extensive studies to solve the above problems and found that scpBNAs are efficiently synthesized via an intermediate compound represented by formula (I) as described later. On the basis of this and other findings, the inventors completed the invention.

The present invention relates to the following [1] to [37].

[1] A method for producing a compound represented by formula (II):

(II)

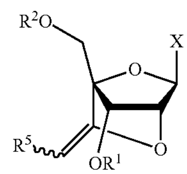

wherein X, $R^1$, $R^2$ and $R^5$ are as defined below, the method comprising at least intramolecularly cyclizing a compound represented by formula (I):

(I)

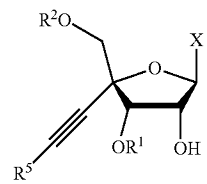

wherein

X represents a nucleic acid base moiety optionally having one or more substituents selected from a group α consisting of a hydroxy group, a hydroxy group protected by a protecting group for nucleic acid synthesis, an alkyl group of 1 to 5 carbon atoms, an alkoxy group of 1 to 5 carbon atoms, a mercapto group, a mercapto group protected by a protecting group for nucleic acid synthesis, an alkylthio group of 1 to 5 carbon atoms, an amino group, an amino group protected by a protecting group for nucleic acid synthesis, an amino group substituted with an alkyl group of 1 to 5 carbon atoms, and a halogen atom;

$R^1$ and $R^2$ each independently represent a hydrogen atom, a protecting group for a hydroxy group used in nucleic acid synthesis, an optionally branched or cyclic alkyl group of 1 to 7 carbon atoms, an optionally branched or cyclic alkenyl group of 2 to 7 carbon atoms, an aryl group of 3 to 10 carbon atoms optionally having one or more substituents selected from the group α and optionally containing a heteroatom, an aralkyl group having an aryl moiety of 3 to 12 carbon atoms optionally having one or more substituents selected from the group α and optionally containing a heteroatom, an acyl group optionally having one or more substituents selected from the group α, a silyl group optionally having one or more substituents selected from the group α, a phosphate group optionally having one or more substituents selected from the group α, a phosphate group protected by a protecting group for nucleic acid synthesis, or $—P(R^3)R^4$ (wherein $R^3$ and $R^4$ each independently represent a hydroxy group, a hydroxy group protected by a protecting group for nucleic acid synthesis, a mercapto group, a mercapto group protected by a protecting group for nucleic acid synthesis, an amino group, an alkoxy group of 1 to 5 carbon atoms, an alkylthio group of 1 to 5 carbon atoms, a cyanoalkoxy group of 1 to 6 carbon atoms, or an amino group substituted with an alkyl group of 1 to 6 carbon atoms); and $R^5$ represents a hydrogen atom, a halogen atom, an optionally branched or cyclic alkyl group of 1 to 7 carbon atoms optionally substituted with an aryl group of 3 to 12 carbon atoms optionally containing a heteroatom, an aralkyl group having an aryl moiety of 3 to 12 carbon atoms optionally containing a heteroatom, or a silyl group.

[2] The production method according to the above [1], wherein the intramolecular cyclization is performed in the presence of a base.

[3] The production method according to the above [2], wherein the base is an alkoxide.

[4] The production method according to any one of the above [1] to [3], further comprising producing a compound represented by formula (I) by deprotecting $R^6$ of a compound represented by formula (IV):

(IV)

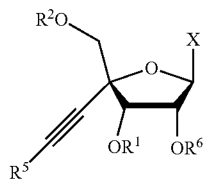

wherein

X represents a nucleic acid base moiety optionally having one or more substituents selected from a group α consisting of a hydroxy group, a hydroxy group protected by a protecting group for nucleic acid synthesis, an alkyl group of 1 to 5 carbon atoms, an alkoxy group of 1 to 5 carbon atoms, a mercapto group, a mercapto group protected by a protecting group for nucleic acid synthesis, an alkylthio group of 1 to 5 carbon atoms, an amino group, an amino group protected by a protecting group for nucleic acid synthesis, an amino group substituted with an alkyl group of 1 to 5 carbon atoms, and a halogen atom;

$R^1$ and $R^2$ each independently represent a hydrogen atom, a protecting group for a hydroxy group used in nucleic acid synthesis, an optionally branched or cyclic alkyl group of 1 to 7 carbon atoms, an optionally branched or cyclic alkenyl group of 2 to 7 carbon atoms, an aryl group of 3 to 10 carbon atoms optionally having one or more substituents selected from the group α and optionally containing a heteroatom, an aralkyl group having an aryl moiety of 3 to 12 carbon atoms optionally having one or more substituents selected from the group α and optionally containing a heteroatom, an acyl group optionally having one or more substituents selected from the group α, a silyl group optionally having one or more substituents selected from the group α, a phosphate group optionally having one or more substituents selected from the group α, a phosphate group protected by a protecting group for nucleic acid synthesis, or —$P(R^3)R^4$ (wherein $R^3$ and $R^4$ each independently represent a hydroxy group, a hydroxy group protected by a protecting group for nucleic acid synthesis, a mercapto group, a mercapto group protected by a protecting group for nucleic acid synthesis, an amino group, an alkoxy group of 1 to 5 carbon atoms, an alkylthio group of 1 to 5 carbon atoms, a cyanoalkoxy group of 1 to 6 carbon atoms, or an amino group substituted with an alkyl group of 1 to 6 carbon atoms);

$R^5$ represents a hydrogen atom, a halogen atom, an optionally branched or cyclic alkyl group of 1 to 7 carbon atoms optionally substituted with an aryl group of 3 to 12 carbon atoms optionally containing a heteroatom, an aralkyl group having an aryl moiety of 3 to 12 carbon atoms optionally containing a heteroatom, or a silyl group; and $R^6$ represents a protecting group for a hydroxy group used in nucleic acid synthesis.

[5] The production method according to the above [4], wherein $R^6$ is an acetyl group.

[6] The production method according to any one of the above [1] to [5], further comprising producing a compound represented by formula (I) using, as a starting material, a compound represented by formula (V):

(V)

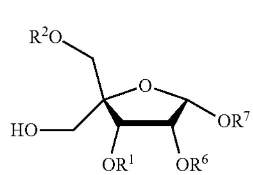

wherein $R^1$ and $R^2$ each independently represent a hydrogen atom, a protecting group for a hydroxy group used in nucleic acid synthesis, an optionally branched or cyclic alkyl group of 1 to 7 carbon atoms, an optionally branched or cyclic alkenyl group of 2 to 7 carbon atoms, an aryl group of 3 to 10 carbon atoms optionally having one or more substituents selected from a group α and optionally containing a heteroatom (wherein the group α consists of a hydroxy group, a hydroxy group protected by a protecting group for nucleic acid synthesis, an alkyl group of 1 to 5 carbon atoms, an alkoxy group of 1 to 5 carbon atoms, a mercapto group, a mercapto group protected by a protecting group for nucleic acid synthesis, an alkylthio group of 1 to 5 carbon atoms, an amino group, an amino group protected by a protecting group for nucleic acid synthesis, an amino group substituted with an alkyl group of 1 to 5 carbon atoms, and a halogen atom), an aralkyl group having an aryl moiety of 3 to 12 carbon atoms optionally having one or more substituents selected from the group α and optionally containing a heteroatom, an acyl group optionally having one or more substituents selected from the group α, a silyl group optionally having one or more substituents selected from the group α, a phosphate group optionally having one or more substituents selected from the group α, a phosphate group protected by a protecting group for nucleic acid synthesis, or —$P(R^3)$ $R^4$ (wherein $R^3$ and $R^4$ each independently represent a hydroxy group, a hydroxy group protected by a protecting group for nucleic acid synthesis, a mercapto group, a mercapto group protected by a protecting group for nucleic acid synthesis, an amino group, an alkoxy group of 1 to 5 carbon atoms, an alkylthio group of 1 to 5 carbon atoms, a cyanoalkoxy group of 1 to 6 carbon atoms, or an amino group substituted with an alkyl group of 1 to 6 carbon atoms); and $R^6$ and $R^7$ each independently represent a protecting group for a hydroxy group used in nucleic acid synthesis, an optionally branched or cyclic alkyl group of 1 to 7 carbon atoms, an optionally branched or cyclic alkenyl group of 2 to 7 carbon atoms, an aryl group of 3 to 10 carbon atoms optionally having one or more substituents selected from the group α and optionally containing a heteroatom, an aralkyl group having an aryl moiety of 3 to 12 carbon atoms optionally having one or more substituents selected from the group α and optionally containing a heteroatom, an acyl group optionally having one or more substituents selected from the group α, a silyl group optionally having one or more substituents selected from the group α, a phosphate group optionally having one or more substituents selected from the group α, or a phosphate group protected by a protecting group for nucleic acid synthesis, or $R^6$ and $R^7$ are joined together to form —$C(R^8)(R^9)$— (wherein $R^8$ and $R^9$ each independently represent a hydrogen atom, an optionally branched or cyclic alkyl group of 1 to 7 carbon atoms optionally substituted with an aryl group of 3 to 12 carbon atoms optionally containing a heteroatom, or an aralkyl group having an aryl moiety of 3 to 12 carbon atoms optionally containing a heteroatom).

[7] The production method according to the above [6], wherein $R^1$ and $R^2$ are benzyl groups.

[8] A method for producing a compound represented by formula (III):

(III)

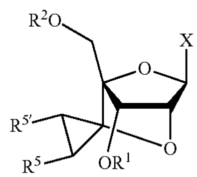

wherein X, $R^1$, $R^2$ and $R^5$ are as defined above, and $R^{5'}$ is independently as defined for $R^5$, the method comprising cyclopropanating a compound represented by formula (II) as described above, wherein the cyclopropanation comprises post-treatment of a reaction mixture with ammonia.

[9] The production method according to the above [8], wherein X is a group having a pyrimidine skeleton.

[10] A method for producing a compound represented by formula (III) as described above, the method comprising at least cyclopropanating, in the presence of an organic acid, a compound represented by formula (II) as described above.

[11] The production method according to the above [10], wherein X is a group having a purine skeleton.

[12] A method for producing a compound represented by formula (III) as described above, the method comprising at least intramolecularly cyclizing a compound represented by formula (I) as described above to produce a compound represented by formula (II) as described above, and cyclopropanating the compound represented by formula (II) as described above.

[13] The production method according to the above [12], wherein the method further comprises preparing the compound represented by formula (I) by the production method according to any one of the above [4] to [7].

[14] The production method according to the above [12] or [13], wherein the intramolecular cyclization is performed by the production method according to any one of the above [1] to [7].

[15] The production method according to any one of the above [12] to [14], wherein the cyclopropanation is performed by the production method according to any one of the above [8] to [11].

[16] A compound represented by formula (IV) as described above with the exception of the case where X is a 2,4-dioxo-1,2,3,4-tetrahydropyrimidin-1-yl group, $R^1$ and $R^2$ are benzyl groups, and $R^6$ is an acetyl group; and the case where X is a 2,4-dioxo-1,2,3,4-tetrahydropyrimidin-1-yl group, and $R^1$, $R^2$ and $R^6$ are acetyl groups.

[17] The compound according to the above [16], wherein $R^6$ is an acetyl group.

[18] The compound according to the above [16] or [17], wherein X is a group having a uracil skeleton having a substituent or a group having a cytosine skeleton having a substituent.

[19] The compound according to the above [18], wherein the substituent is selected from the group consisting of a hydroxy group and an alkyl group of 1 to 6 carbon atoms.

[20] The compound according to any one of the above [16] to [19], wherein the compound represented by formula (IV) is selected from the following:

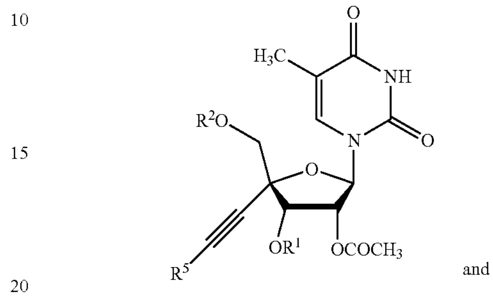

and

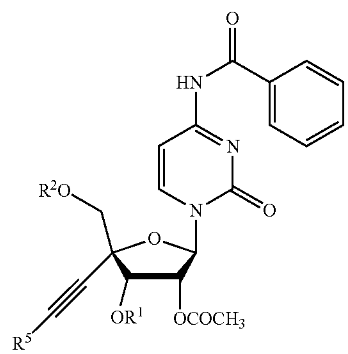

.

[21] The compound according to the above [16] or [17], wherein X is a group having a purine skeleton having a substituent.

[22] The compound according to the above [21], wherein the substituent is selected from the group consisting of a hydroxy group, an amino group, and an amino group protected by a protecting group.

[23] The compound according to any one of the above [16], [17], [21] and [22], wherein the compound represented by formula (IV) is a compound selected from the following:

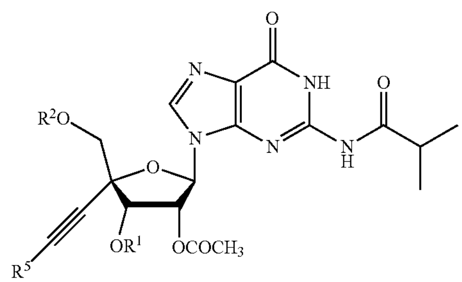

and

-continued

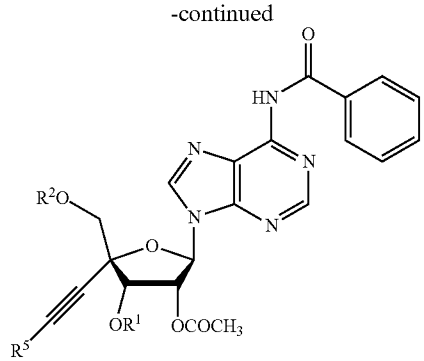

.

[24] A compound represented by formula (I) as described above with the exception of the case where X is a 2,4-dioxo-1,2,3,4-tetrahydropyrimidin-1-yl group, and $R^1$ and $R^2$ are benzyl groups; and the case where X is a 2-oxo-4-amino-1,2-dihydropyrimidin-1-yl group, and $R^1$ and $R^2$ are hydrogen atoms.

[25] The compound according to the above [24], wherein X is a group having a uracil skeleton having a substituent or a group having a cytosine skeleton having a substituent.

[26] The compound according to the above [25], wherein the substituent is selected from the group consisting of a hydroxy group and an alkyl group of 1 to 6 carbon atoms.

[27] The compound according to anyone of the above [24] to [26], wherein the compound represented by formula (I) is selected from the following:

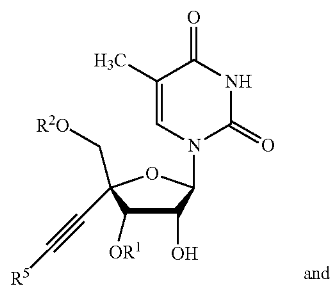

and

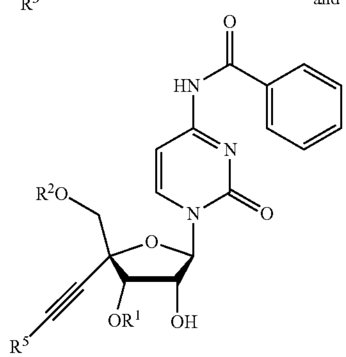

.

[28] The compound according to the above [24], wherein X is a group having a purine skeleton having a substituent.

[29] The compound according to the above [28], wherein the substituent is selected from the group consisting of a hydroxy group, an amino group, and an amino group protected by a protecting group.

[30] The compound according to any one of the above [24], [28] and [29], wherein the compound represented by formula (I) is a compound selected from the following:

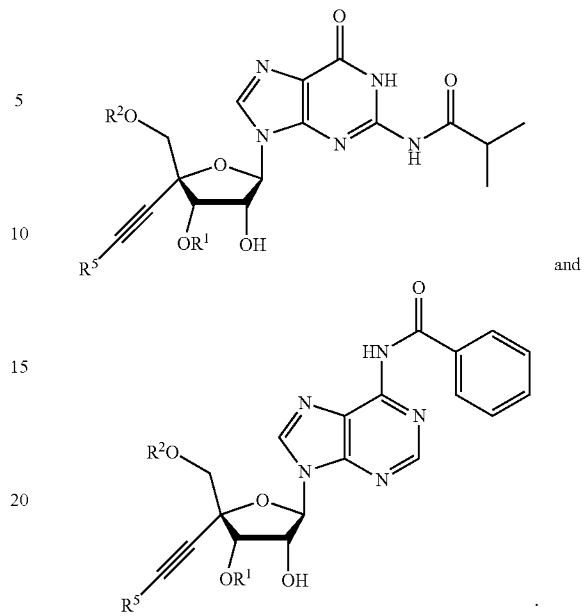

and

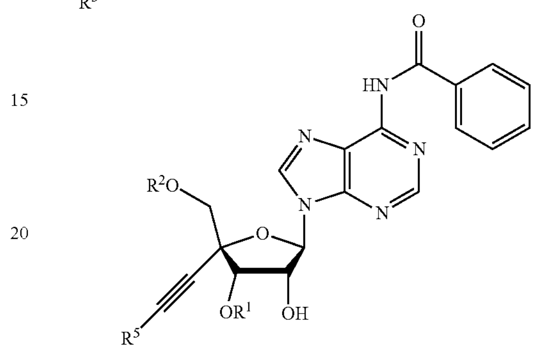

.

[31] A compound represented by formula (II) as described above with the exception of the case where X is a 2,4-dioxo-1,2,3,4-tetrahydropyrimidin-1-yl group, $R^1$ is a naphthyl group, and $R^2$ is a benzyl group; and the case where X is a 2,4-dioxo-1,2,3,4-tetrahydropyrimidin-1-yl group, $R^1$ is a naphthyl group, and $R^2$ is a hydrogen atom.

[32] The compound according to the above [31], wherein X is a group having a uracil skeleton having a substituent or a group having a cytosine skeleton having a substituent.

[33] The compound according to the above [32], wherein the substituent is selected from the group consisting of a hydroxy group and an alkyl group of 1 to 6 carbon atoms.

[34] The compound according to anyone of the above [31] to [33], wherein the compound represented by formula (II) is selected from the following:

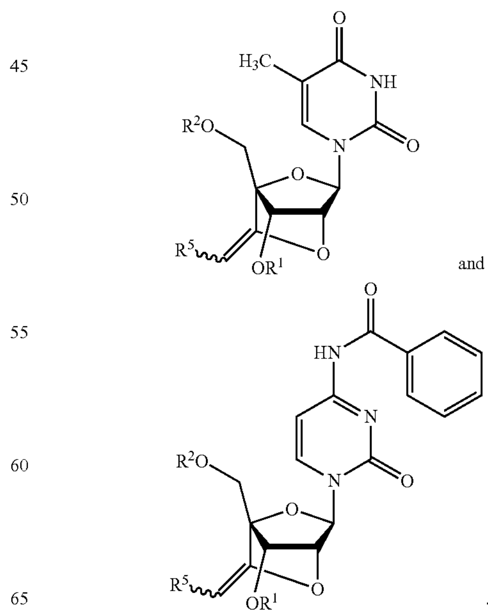

and

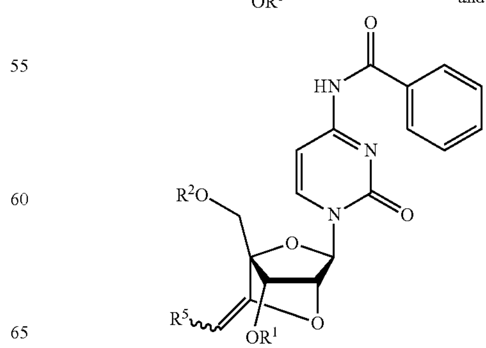

.

[35] The compound according to the above [31], wherein X is a group having a purine skeleton having a substituent.

[36] The compound according to the above [35], wherein the substituent is selected from the group consisting of a hydroxy group, an amino group, and an amino group protected by a protecting group.

[37] The compound according to any one of the above [31], [35] and [36], wherein the compound represented by formula (II) is a compound selected from the following:

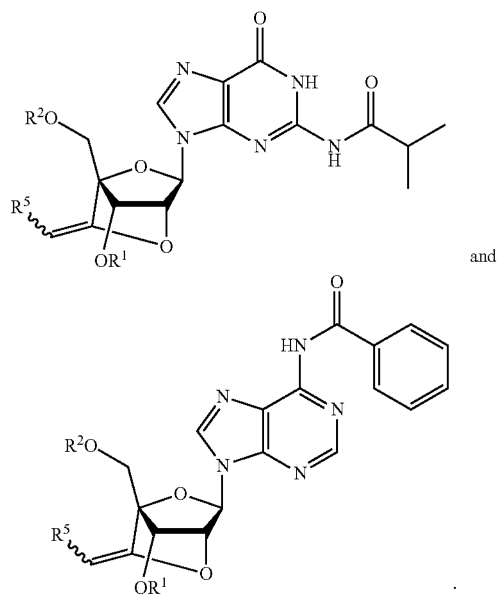

and

.

Advantageous Effects of Invention

The present invention enables efficient production of scpBNAs.

DESCRIPTION OF EMBODIMENTS

The present invention is characterized by use of an intermediate compound represented by formula (I) as described later.

The present invention involves the use of the intermediate compound, resulting in no need of stereoinversion of the hydroxy group at the 2'-position of a nucleoside sugar moiety. The stereoinversion of the hydroxy group is conventionally performed in multiple steps in the art, but the number of steps can be reduced according to the invention, and scpBNAs may be efficiently produced. The present invention is, however, not limited to this assumption.

The terms and definitions as used herein will be described below.

The term "nucleic acid base moiety" refers to a cyclic hydrocarbon group as well as a 5- to 20-membered aromatic heterocyclic group in which the carbon atoms of the ring are substituted with one or more heteroatoms such as nitrogen, sulfur and oxygen atoms. The nucleic acid base moiety includes a monocyclic ring and a fused ring. Specific examples of the hydrocarbon ring include benzene, naphthalene, anthracene, phenanthrene, indane, indene, tetrahydronaphthylene, and biphenylene. Examples of the heterocyclic ring include a purine base of nucleic acids and a pyrimidine base of nucleic acids. Such hydrocarbon and heterocyclic rings may have one or more substituents selected from the group α as described later. The purine base of nucleic acids and the pyrimidine base of nucleic acids include bases commonly known to serve as a constituent of a nucleic acid (for example, guanine, adenine, cytosine, thymine, and uracil), and other similar chemical structures capable of acting as or substituting for a base of nucleic acids or a tautomer thereof (for example, a keto-enol tautomer, or an imine-enamine tautomer). The purine base and the pyrimidine base also include thiophene, thianthrene, furan, pyran, isobenzofuran, chromene, xanthene, phenoxanthiin, pyrrole, imidazole, pyrazole, isothiazole, isoxazole, pyridazine, indolizine, indole, isoindole, isoquinoline, quinoline, naphthyridine, quinoxaline, quinazoline, pteridine, carbazole, phenanthridine, acridine, perimidine, phenazine, phenarsazine, phenothiazine, furazan, phenoxazine, pyrrolidine, pyrroline, imidazolidine, imidazoline, and pyrazolidine. The nucleic acid base moiety is preferably a purine or pyrimidine base, or a purine or pyrimidine base optionally having one or more substituents selected from the group α as described later. Specific examples of preferred nucleic acid base moieties include a purin-9-yl group or a 2-oxo-pyrimidin-1-yl group, or a purin-9-yl or 2-oxo-pyrimidin-1-yl group having a substituent selected from the group α as described below. The group α consists of a hydroxy group, a hydroxy group protected by a protecting group for nucleic acid synthesis, an alkyl group of 1 to 5 carbon atoms, an alkoxy group of 1 to 5 carbon atoms, a mercapto group, a mercapto group protected by a protecting group for nucleic acid synthesis, an alkylthio group of 1 to 5 carbon atoms, an amino group, an amino group protected by a protecting group for nucleic acid synthesis, an amino group substituted with an alkyl group of 1 to 5 carbon atoms, and a halogen atom.

A preferred purine base optionally having a substituent includes 6-aminopurin-9-yl (i.e., adeninyl), 6-aminopurin-9-yl in which the amino group is protected by a protecting group for nucleic acid synthesis, 2,6-diaminopurin-9-yl, 2-amino-6-chloropurin-9-yl, 2-amino-6-chloropurin-9-yl in which the amino group is protected by a protecting group for nucleic acid synthesis, 2-amino-6-fluoropurin-9-yl, 2-amino-6-fluoropurin-9-yl in which the amino group is protected by a protecting group for nucleic acid synthesis, 2-amino-6-bromopurin-9-yl, 2-amino-6-bromopurin-9-yl in which the amino group is protected by a protecting group for nucleic acid synthesis, 2-amino-6-hydroxypurin-9-yl (i.e., guaninyl), 2-amino-6-hydroxypurin-9-yl in which one or both of the amino group and the hydroxy group are protected by a protecting group for nucleic acid synthesis, 6-amino-2-methoxypurin-9-yl, 6-amino-2-chloropurin-9-yl, 6-amino-2-fluoropurin-9-yl, 2,6-dimethoxypurin-9-yl, 2,6-dichloropurin-2-yl and 6-mercaptopurin-9-yl.

A preferred pyrimidine base optionally having a substituent includes 2-oxo-4-amino-1,2-dihydropyrimidin-1-yl (i.e., cytosinyl), 2-oxo-4-amino-1,2-dihydropyrimidin-1-yl in which one or both of the amino group and the hydroxy group are protected by a protecting group for nucleic acid synthesis, 2-oxo-4-amino-5-fluoro-1,2-dihydropyrimidin-1-yl, 2-oxo-4-amino-5-fluoro-1,2-dihydropyrimidin-1-yl in which the amino group is protected by a protecting group for nucleic acid synthesis, 4-amino-2-oxo-5-chloro-1,2-dihydropyrimidin-1-yl, 2-oxo-4-methoxy-1,2-dihydropyrimidin-1-yl, 2-oxo-4-mercapto-1,2-dihydropyrimidin-1-yl, 2-oxo-4-hydroxy-1,2-dihydroxypyrimidin-1-yl (i.e., uracinyl), 2-oxo-4-hydroxy-5-methyl-1,2-dihydropyrimidin-1-yl (i.e., thyminyl), 4-amino-5-methyl-2-oxo-1,2-dihydropyrimidin-1-yl (i.e., 5-methylcytosinyl), and 2-oxo-4-amino-5-methyl- 1,2-dihydropyrimidin-1-yl in which the amino group is protected by a protecting group for nucleic acid synthesis.

A more preferred purine or pyrimidine base optionally having a substituent includes 6-aminopurin-9-yl (i.e., adeninyl), 6-aminopurin-9-yl in which the amino group is protected by a protecting group for nucleic acid synthesis (for example, 6-benzoylaminopurin-9-yl or 1-benzyloxymethyl-6-benzoylaminopurin-9-yl), 2-amino-6-hydroxypurin-9-yl (i.e., guaninyl), 2-amino-6-hydroxypurin-9-yl in which one or both of the amino group and the hydroxy group are protected by a protecting group for nucleic acid synthesis (for example, 2-isobutyrylamino-6-hydroxypurin-9-yl, or 2-isobutyrylamino-6-diphenylcarbamoyloxypurin-9-yl), 2-oxo-4-amino-1,2-dihydropyrimidin-1-yl (i.e., cytosinyl), 2-oxo-4-amino-1,2-dihydropyrimidin-1-yl in which the amino group is protected by a protecting group for nucleic acid synthesis (for example, 2-oxo-4-benzoylamino-1,2-dihydropyrimidin-1-yl), 2-oxo-4-hydroxy-1,2-dihydropyrimidin-1-yl (i.e., uracinyl), 2-oxo-4-hydroxy-5-methyl-1,2-dihydropyrimidin-1-yl (i.e., thyminyl), 4-amino-5-methyl-2-oxo-1,2-dihydropyrimidin-1-yl (i.e., 5-methylcytosinyl), and 4-amino-5-methyl-2-oxo-1,2-dihydropyrimidin-1-yl in which the amino group is protected by a protecting group for nucleic acid synthesis (for example, 2-oxo-4-banzoylamino-5-methyl-1,2-dihydropyrimidin-1-yl).

The term "protecting group" as used in the phrases "a protecting group for an amino group used in nucleic acid synthesis", "a protecting group for a hydroxy group used in nucleic acid synthesis", "an amino group protected by a protecting group for nucleic acid synthesis," and "a hydroxy group protected by a protecting group for nucleic acid synthesis" refers to any group capable of stably protecting an amino or hydroxy group during nucleic acid synthesis. In particular, the protecting group refers to a group that is stable under acidic or neutral conditions and is cleavable by chemical methods such as hydrogenolysis, hydrolysis, electrolysis or photolysis. Examples of the protecting group include aliphatic acyl groups including alkylcarbonyl groups such as formyl, acetyl, propionyl, butyryl, isobutyryl, pentanoyl, pivaloyl, valeryl, isovaleryl, octanoyl, nonanoyl, decanoyl, 3-methylnonanoyl, 8-methylnonanoyl, 3-ethyloctanoyl, 3,7-dimethyloctanoyl, undecanoyl, dodecanoyl, tridecanoyl, tetradecanoyl, pentadecanoyl, hexadecanoyl, 1-methylpentadecanoyl, 14-methylpentadecanoyl, 13,13-dimethyltetradecanoyl, heptadecanoyl, 15-methylhexadecanoyl, octadecanoyl, 1-methylheptadecanoyl, nonadecanoyl, 4-oxopentanoyl (levulinoyl), icosanoyl and henicosanoyl, carboxylated alkylcarbonyl groups such as succinoyl, glutaroyl and adipoyl, halogeno lower alkyl carbonyl groups such as chloroacetyl, dichloroacetyl, trichloroacetyl and trifluoroacetyl, alkoxy lower alkyl carbonyl groups such as methoxyacetyl, phenoxyacetyl and 2-(4-tert-butyl) phenoxyacetyl, and unsaturated alkylcarbonyl groups such as (E)-2-methyl-2-butenoyl; aromatic acyl groups including arylcarbonyl groups such as benzoyl, α-naphthoyl and β-naphthoyl, halogeno arylcarbonyl groups such as 2-bromobenzoyl and 4-chlorobenzoyl, lower alkylated arylcarbonyl groups such as 2,4,6-trimethylbenzoyl and 4-toluoyl, lower alkoxylated arylcarbonyl groups such as 4-anisoyl, carboxylated arylcarbonyl groups such as 2-carboxybenzoyl, 3-carboxybenzoyl and 4-carboxybenzoyl, lower alkoxycarboxylated arylcarbonyl groups such as 2-(methoxycarbonyl)benzoyl, nitrated arylcarbonyl groups such as 4-nitrobenzoyl and 2-nitrobenzoyl, and arylated arylcarbonyl groups such as 4-phenylbenzoyl; lower alkyl groups including methyl, ethyl, n-propyl, isopropyl, n-butyl, isobutyl, s-butyl, tert-butyl, n-pentyl, isopentyl, 2-methylbutyl, neopentyl, 1-ethylpropyl, n-hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl and 2-ethylbutyl; lower alkenyl groups including ethenyl, 1-propenyl, 2-propenyl, 1-methyl-2-propenyl, 1-methyl-1-propenyl, 2-methyl-1-propenyl, 2-methyl-2-propenyl, 2-ethyl-2-propenyl, 1-butenyl, 2-butenyl, 1-methyl-2-butenyl, 1-methyl-1-butenyl, 3-methyl-2-butenyl, 1-ethyl-2-butenyl, 3-butenyl, 1-methyl-3-butenyl, 2-methyl-3-butenyl, 1-ethyl-3-butenyl, 1-pentenyl, 2-pentenyl, 1-methyl-2-pentenyl, 2-methyl-2-pentenyl, 3-pentenyl, 1-methyl-3-pentenyl, 2-methyl-3-pentenyl, 4-pentenyl, 1-methyl-4-pentenyl, 2-methyl-4-pentenyl, 1-hexenyl, 2-hexenyl, 3-hexenyl, 4-hexenyl and 5-hexenyl; halogeno lower alkyl groups including 2,2,2-trichloroethyl, 2,2,2-tribromoethyl, 2,2,2-trifluoroethyl and 2,2,2-trichloro-1,1-dimethylethyl; aralkyl groups including a methyl group substituted with 1 to 3 aryl groups, such as benzyl, α-naphthylmethyl, β-naphthylmethyl, diphenylmethyl, triphenylmethyl, α-naphthyldiphenylmethyl or 9-anthrylmethyl, and a methyl group substituted with 1 to 3 aryl groups substituted with a lower alkyl, a lower alkoxy, a halogen or a cyano group, such as 4-methylbenzyl, 2,4,6-trimethylbenzyl, 3,4,5-trimethylbenzyl, 4-methoxybenzyl, 4-methoxyphenyldiphenylmethyl, 4,4'-dimethoxytriphenylmethyl, 2-nitrobenzyl, 4-nitrobenzyl, 4-chlorobenzyl, 4-bromobenzyl or 4-cyanobenzyl; aryl groups substituted with a halogen atom, a lower alkoxy group or a nitro group, including 4-chlorophenyl, 2-chlorophenyl, 4-methoxyphenyl, 4-nitrophenyl and 2,4-dinitrophenyl; silyl groups including tri-lower alkyl silyl groups such as trimethylsilyl, triethylsilyl, isopropyldimethylsilyl, t-butyldimethylsilyl, methyldiisopropylsilyl, methyl-di-t-butylsilyl and triisopropylsilyl, and a lower alkyl silyl group substituted with 1 or 2 aryl groups, such as diphenylmethylsilyl, tert-butyldiphenylsilyl, diphenylisopropylsilyl or phenyldiisopropylsilyl; tetrahydropyranyl or tetrahydrothiopyranyl groups including tetrahydropyran-2-yl, 3-bromotetrahydropyran-2-yl, 4-methoxytetrahydropyran-4-yl, tetrahydrothiopyran-4-yl and 4-methoxytetrahydrothiopyran-4-yl; tetrahydrofuranyl or tetrahydrothiofuranyl groups including tetrahydrofuran-2-yl and tetrahydrothiofuran-2-yl; lower alkoxy alkyl groups including lower alkoxy methyl groups such as methoxymethyl, 1,1-dimethyl-1-methoxymethyl, ethoxymethyl, propoxymethyl, isopropoxymethyl, butoxymethyl and t-butoxymethyl, and lower alkoxy ethyl groups such as 1-ethoxyethyl and 1-(isopropoxy)ethyl; lower alkoxylated lower alkoxy methyl groups including 2-methoxyethoxymethyl; halogeno lower alkoxy methyl groups including 2,2,2-trichloroethoxymethyl and bis(2-chloroethoxy)methyl; an aralkyloxymethyl group in which the aryl ring may be substituted with 1 or 2 lower alkoxy or nitro groups including benzyloxymethyl, 4-methoxybenzyloxymethyl and 2-naphthylmethoxymethyl; oxycarbonyl groups including lower alkoxy carbonyl groups such as methoxycarbonyl, ethoxycarbonyl, t-butoxycarbonyl and isobutoxycarbonyl, a lower alkoxy carbonyl group substituted with a halogen atom or a tri-lower alkyl silyl group, such as 2,2,2-trichloroethoxycarbonyl or 2-trimethylsilylethoxycarbonyl, alkenyloxycarbonyl groups such as vinyloxycarbonyl and allyloxycarbonyl, an aralkyloxycarbonyl group in which the aryl ring may be substituted with 1 or 2 lower alkoxy or nitro groups, such as benzyloxycarbonyl, 4-methoxybenzyloxycarbonyl, 3,4-dimethoxybenzyloxycarbonyl, 2-nitrobenzyloxycarbonyl or 4-nitrobenzyloxycarbonyl, and 9-fluorenylmethyloxycarbonyl; and a carbamoyl group in which the nitrogen atom may be substituted with an alkyl group, an aryl group, an alkenyl group, a lower alkoxy group or an aralkyl group, including dimethylcarbamoyl, diphenylcarbamoyl, methylphenylcarbamoyl, 1-pyrrolidinylcarbamoyl or morpholinocarbamoyl. For example, preferred protecting groups serving as "the protecting group for a hydroxy group used in nucleic acid synthesis" are an aliphatic acyl group, an aromatic acyl group, a methyl group substituted with 1 to 3 aryl groups, a methyl group substituted with 1 to 3 aryl groups substituted with a lower alkyl, a lower alkoxy, a halogen, or a cyano group, and a silyl group, and more preferred protecting groups are an acetyl group, a benzoyl group, a benzyl group, a p-methoxybenzoyl group, a dimethoxytrityl group, a monomethoxytrityl group, a tert-butyldiphenylsilyl group, a tert-butyldimethylsilyl group, and a 4-oxopentanoyl (levulinoyl) group. Preferred protecting groups used in the context of "the hydroxy group protected by a protecting group for nucleic acid synthesis" are an aliphatic acyl group, an aromatic acyl group, a methyl group substituted with 1 to 3 aryl groups, an aryl group substituted with a halogen atom, a lower alkoxy group or a nitro group, a lower alkyl group and a lower alkenyl group, and more preferred protecting groups are a benzoyl group, a benzyl group, a 2-chlorophenyl group, a 4-chlorophenyl group and a 2-propenyl group.

A protecting group used in the context of "the mercapto group protected by a protecting group used in nucleic acid synthesis" may be any protecting group capable of stably protecting a mercapto group during nucleic acid synthesis. In particular, the protecting group refers to a group that is stable under acidic or neutral conditions and is cleavable by chemical methods such as hydrogenolysis, hydrolysis, electrolysis or photolysis. Examples of the protecting group include the protecting groups listed above as the protecting group for a hydroxy group, as well as a group capable of forming a disulfide, including alkylthio groups such as methylthio, ethylthio and tert-butylthio, and arylthio groups such as benzylthio. Preferred protecting groups for a mercapto group are an aliphatic acyl group and an aromatic acyl group, and more preferred is a benzoyl group.

A protecting group used in the context of "a phosphate group protected by a protecting group used in nucleic acid synthesis" may be any protecting group capable of stably protecting a phosphate group during nucleic acid synthesis. In particular, the protecting group refers to a group that is stable under acidic or neutral conditions and is cleavable by chemical methods such as hydrogenolysis, hydrolysis, electrolysis or photolysis. Examples of the protecting group include lower alkyl groups, such as methyl, ethyl, n-propyl, isopropyl, n-butyl, isobutyl, s-butyl, tert-butyl, n-pentyl, isopentyl, 2-methylbutyl, neopentyl, 1-ethylpropyl, n-hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl and 2-ethylbutyl; cyanated lower alkyl groups, such as 2-cyanoethyl and 2-cyano-1,1-dimethylethyl; an ethyl group substituted with a silyl group, such as 2-methyldiphenylsilylethyl, 2-trimethylsilylethyl, or 2-triphenylsilylethyl; halogenated lower alkyl groups, such as 2,2,2-trichloroethyl, 2,2,2-triburomoethyl, 2,2,2,-trifluoroethyl and 2,2,2-trichloro-1,1-dimethylethyl; lower alkenyl groups, such as ethenyl, 1-propenyl, 2-propenyl, 1-methyl-2-propenyl, 1-methyl-1-propenyl, 2-methyl-2-propenyl, 2-ethyl-2-propenyl, 1-butenyl, 2-butenyl, 1-methyl-2-butenyl, 1-methyl-1-butenyl, 3-methyl-2-butenyl, 1-ethyl-2-butenyl, 3-butenyl, 1-methyl-3-butenyl, 2-methyl-3-butenyl, 1-ethyl-3-butenyl, 1-pentenyl, 2-pentenyl, 1-methyl-2-pentenyl, 2-methyl-2-pentenyl, 3-pentenyl, 1-methyl-3-pentenyl, 2-methyl-3-pentenyl, 4-pentenyl, 1-methyl-4-pentenyl, 2-methyl-4-pentenyl, 1-hexenyl, 2-hexenyl, 3-hexenyl, 4-hexenyl and 5-hexenyl; cycloalkylgroups, such as cyclopropyl, cyclobutyl, cyclopentyl, cyclohexyl, cycloheptyl, norbornyl and adamantyl; cyanated lower alkenyl groups such as 2-cyanobutenyl; aralkyl groups, such as benzyl, α-naphthylmethyl, β-naphthylmethyl, indenylmethyl, phenanthrenylmethyl, anthracenylmethyl, diphenylmethyl, triphenylmethyl, 1-phenetyl, 2-phenetyl, 1-naphthylethyl, 2-naphthylethyl, 1-phenylpropyl, 2-phenylpropyl, 3-phenylpropyl, 1-naphthylpropyl, 2-naphthylpropyl, 3-naphthylpropyl, 1-phenylbutyl, 2-phenylbutyl, 3-phenylbutyl, 4-phenylbutyl, 1-naphthylbutyl, 2-naphthylbutyl, 3-naphthylbutyl, 4-naphthylbutyl, 1-phenylpentyl, 2-phenylpentyl, 3-phenylpentyl, 4-phenylpentyl, 5-phenylpentyl, 1-naphthylpentyl, 2-naphthylpentyl, 3-naphthylpentyl, 4-naphthylpentyl, 5-naphthylpentyl, 1-phenylhexyl, 2-phenylhexyl, 3-phenylhexyl, 4-phenylhexyl, 5-phenylhexyl, 6-phenylhexyl, 1-naphtylpentyl, 2-naphthylpentyl, 3-naphthylpentyl, 4-naphthylpentyl, 5-naphthylpentyl and 6-naphthylpentyl; an aralkyl group in which the aryl ring is substituted with a nitro group or a halogen atom, such as 4-chlorobenzyl, 2-(4-nitrophenyl)ethyl, o-nitrobenzyl, 4-nitrobenzyl, 2,4-dinitrobenzyl or 4-chloro-2-nitrobenzyl; aryl groups, such as phenyl, indenyl, naphthyl, phenanthrenyl and anthracenyl; and an aryl group substituted with a lower alkyl group, a halogen atom or a nitro group, such as 2-methylphenyl, 2,6-dimethylphenyl, 2-chlorophenyl, 4-chlorophenyl, 2,4-dichlorophenyl, 2,5-dichlorophenyl, 2-bromophenyl, 4-nitrophenyl and 4-chloro-2-nitrophenyl. Preferred protecting groups for a phosphate group are a lower alkyl group, a lower alkyl group substituted with a cyano group, an aralkyl group, an aralkyl group in which the aryl ring is substituted with a nitro group or a halogen atom, and an aryl group substituted with a lower alkyl group, a halogen atom or a nitro group, and more preferred protecting groups are a 2-cyanoethyl group, a 2,2,2-trichloroethyl group, a benzyl group, a 2-chlorophenyl group and a 4-chlorophenyl group.

The term "alkyl group" generally refers to a linear or branched alkyl group of 1 to 20 carbon atoms. Examples of the alkyl group include a linear or branched alkyl group of 1 to 6 carbon atoms (may also be called herein a lower alkyl group), such as methyl, ethyl, n-propyl, isopropyl, n-butyl, isobutyl, s-butyl, tert-butyl, n-pentyl, isopentyl, 2-methylbutyl, neopentyl, 1-ethylpropyl, n-hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl or 2-ethylbutyl; and a linear or branched alkyl group of 7 to 20 carbon atoms, such as heptyl, octyl, nonyl or decyl. Part of the group may form a ring.

The term "alkoxy group" generally refers to an alkoxy group having the alkyl group as described above. Examples of the alkoxy group include methyloxy (methoxy), ethyloxy (ethoxy), n-propyloxy (n-propoxy), isopropoxy, n-butyloxy (n-butoxy), isobutoxy, s-butoxy, tert-butoxy, and n-pentyloxy (n-pentoxy).

The term "cyanoalkoxy group" generally refers to an alkoxy group substituted with any number of cyano groups. Examples of the cyanoalkoxy group include cyanomethoxy, 2-cyanoethoxy, 3-cyanopropoxy, 4-cyanobutoxy, 3-cyano-2-methylpropoxy, 1-cyanomethyl-1,1-dimethylmethoxy, 5-cyanopentyloxy and 6-cyanohexyloxy.

The term "alkylthio group" generally refers to an alkylthio group having the alkyl group as described above. Examples of the alkylthio group include methylthio, ethylthio, propylthio, isopropylthio, butylthio, isobutylthio, 2-butylthio, tert-butylthio, and n-pentylthio.

The term "alkylamino group" generally refers to an alkylamino group having one or two alkyl groups as described above. Examples of the alkylamino group include methylamino, ethylamino, propylamino, isopropylamino, butylamino, isobutylamino, s-butylamino, tert-butylamino, dimethylamino, diethylamino, dipropylamino, diisopropylamino, dibutylamino, diisobutylamino, di(s-butyl)amino, di(tert-butyl)amino, and pentylamino.

The term "alkenyl group" generally refers to a linear or branched alkenyl group of 2 to 20 carbon atoms. Examples of the alkenyl group include a linear or branched alkenyl group of 2 to 6 carbon atoms (may also be called a lower alkenyl group), such as ethenyl, 1-propenyl, 2-propenyl, 1-methyl-2-propenyl, 1-methyl-1-propenyl, 2-methyl-1-propenyl, 2-methyl-2-propenyl, 2-ethyl-2-propenyl, 1-butenyl, 2-butenyl, 1-methyl-2-butenyl, 1-methyl-1-butenyl, 3-methyl-2-butenyl, 1-ethyl-2-butenyl, 3-butenyl, 1-methyl-3-butenyl, 2-methyl-3-butenyl, 1-ethyl-3-butenyl, 1-pentenyl, 2-pentenyl, 1-methyl-2-pentenyl, 2-methyl-2-pentenyl, 3-pentenyl, 1-methyl-3-pentenyl, 2-methyl-3-pentenyl, 4-pentenyl, 1-methyl-4-pentenyl, 2-methyl-4-pentenyl, 1-hexenyl, 2-hexenyl, 3-hexenyl, 4-hexenyl or 5-hexenyl; or heptenyl, geranyl or farnesyl. Part of the group may form a ring.

The term "aryl group" generally means a monovalent substituent group of 6 to 14 carbon atoms derived from removing one hydrogen atom from an aromatic hydrocarbon group. Examples of the aryl group include phenyl, indenyl, naphthyl, phenanthrenyl, and anthracenyl. The aryl ring may be substituted with one or more of a halogen atom, a lower alkyl group, a hydroxy group, an alkoxy group, an aryloxy group, an amino group, a nitro group, a trifluoromethyl group, a phenyl group, etc. Examples of such an optionally substituted aryl group include 2-methylphenyl, 2,6-dimethylphenyl, 2-chlorophenyl, 4-chlorophenyl, 2,4-dichlorophenyl, 2,5-dichlorophenyl, 2-bromophenyl, 4-methoxyphenyl, 4-chloro-2-nitrophenyl, 4-nitrophenyl, 2,4-dinitrophenyl and biphenyl. The aryl group may contain a heteroatom, and may include, for example, a heteroaryl in which at least one ring carbon atom of the aryl group is substituted with a heteroatom (for example, a nitrogen atom, an oxygen atom, a sulfur atom, etc.). Examples of the heteroaryl include pyridyl, pyrrolyl, quinolyl, indolyl, imidazolyl, furyl, and thienyl.

The term "aralkyl group" generally means an alkyl group of 1 to 6 carbon atoms substituted with an aryl group. Examples of the aralkyl group include a methyl group substituted with to 3 aryl groups, such as benzyl, α-naphthylmethyl, β-naphthylmethyl, indenylmethyl, phenanthrenylmethyl, anthracenylmethyl, diphenylmethyl, triphenylmethyl, α-naphthyldiphenylmethyl or 9-anthrylmethyl; a methyl group substituted with 1 to 3 aryl groups substituted with a lower alkyl, a lower alkoxy, a halogen or a cyano group, such as 4-methylbenzyl, 2,4,6-trimethylbenzyl, 3,4,5-trimethylbenzyl, 4-methoxybenzyl, 4-methoxyphenyldiphenylmethyl, 4,4'-dimethoxytriphenylmethyl, 2-nitrobenzyl, 4-nitrobenzyl, 4-chlorobenzyl, 4-bromobenzyl or 4-cyanobenzyl; an alkyl group of 2 to 6 carbon atoms substituted with an aryl group, such as 1-phenethyl, 2-phenethyl, 1-naphthylethyl, 2-naphthylethyl, 1-phenylpropyl, 2-phenylpropyl, 3-phenylpropyl, 1-naphthylpropyl, 2-naphthylpropyl, 3-naphthylpropyl, 1-phenylbutyl, 2-phenylbutyl, 3-phenylbutyl, 4-phenylbutyl, 1-naphthylbutyl, 2-naphthylbutyl, 3-naphthylbutyl, 4-naphthylbutyl, 1-phenylpentyl, 2-phenylpentyl, 3-phenylpentyl, 4-phenylpentyl, 5-phenylpentyl, 1-naphthylpentyl, 2-naphthylpentyl, 3-naphthylpentyl, 4-naphthylpentyl, 5-naphthylpentyl, 1-phenylhexyl, 2-phenylhexyl, 3-phenylhexyl, 4-phenylhexyl, 5-phenylhexyl, 6-phenylhexyl, 1-naphthylpentyl, 2-naphthylpentyl, 3-naphthylpentyl, 4-naphthylpentyl, 5-naphthylpentyl, or 6-naphthylpentyl; etc.

The "acyl group" includes, for example, aliphatic acyl groups including alkylcarbonyl groups such as a formyl, acetyl, propionyl, butyryl, isobutyryl, pentanoyl, pivaloyl, valeryl, isovaleryl, octanoyl, nonanoyl, decanoyl, 3-methylnonanoyl, 8-methylnonanoyl, 3-ethyloctanoyl, 3,7-dimethyloctanoyl, undecanoyl, dodecanoyl, tridecanoyl, tetradecanoyl, pentadecanoyl, hexadecanoyl, 1-methylpentadecanoyl, 14-methylpentadecanoyl, 13,13-dimethyltetradecanoyl, heptadecanoyl, 15-methylhexadecanoyl, octadecanoyl, 1-methylheptadecanoyl, nonadecanoyl, icosanoyl and henicosanoyl, carboxylated alkylcarbonyl groups such as succinoyl, glutaroyl and adipoyl, halogeno lower alkyl carbonyl groups such as chloroacetyl, dichloroacetyl, trichloroacetyl and trifluoroacetyl, lower alkoxy lower alkyl carbonyl groups such as methoxyacetyl, unsaturated alkylcarbonyl groups such as (E)-2-methyl-2-butenoyl; and aromatic acyl groups including arylcarbonyl groups such as benzoyl, α-naphthoyl and β-naphthoyl, halogeno arylcarbonyl groups such as 2-bromobenzoyl and 4-chlorobenzoyl, lower alkylated arylcarbonyl groups such as 2,4,6-trimethylbenzoyl and 4-toluoyl, lower alkoxylated arylcarbonyl groups such as 4-anisoyl, carboxylated arylcarbonyl groups such as 2-carboxybenzoyl, 3-carboxybenzoyl and 4-carboxybenzoyl, nitrated arylcarbonyl groups such as 4-nitrobenzoyl and 2-nitrobenzoyl, lower alkoxycarboxylated arylcarbonyl groups such as 2-(methoxycarbonyl)benzoyl, and arylated arylcarbonyl groups such as 4-phenylbenzoyl.

The "silyl group" includes tri-lower alkyl silyl groups such as trimethylsilyl, triethylsilyl, isopropyldimethylsilyl, t-butyldimethylsilyl, methyldiisopropylsilyl, methyl-di-t-butylsilyl and triisopropylsilyl; a lower alkyl silyl group substituted with 1 or 2 aryl groups, such as diphenylmethylsilyl, butyldiphenylbutylsilyl, diphenylisopropylsilyl or phenyldiisopropylsilyl; etc.

The "halogen atom" includes, for example, a fluorine atom, a chlorine atom, a bromine atom and an iodine atom.

The present invention will be described in detail below.

A method for producing a compound represented by formula (III) according to the present invention may be any method using a compound represented by formula (I) below as a starting material, and comprises at least using a compound represented by formula (I):

(I)

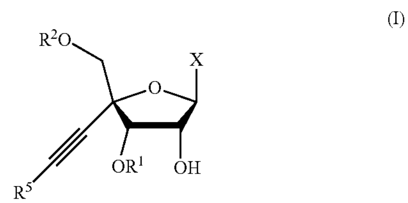

wherein

X represents a nucleic acid base moiety optionally having one or more substituents selected from the group α; $R^1$ and $R^2$ each independently represent a hydrogen atom, a protecting group for a hydroxy group used in nucleic acid synthesis, an optionally branched or cyclic alkyl group of 1 to 7 carbon atoms, an optionally branched or cyclic alkenyl group of 2 to 7 carbon atoms, an aryl group of 3 to 10 carbon atoms optionally having one or more substituents selected from the group α and optionally containing a heteroatom, an aralkyl group having an aryl moiety of 3 to 12 carbon atoms optionally having one or more substituents selected from the group α and optionally containing a heteroatom, an acyl group optionally having one or more substituents selected from the group α, a silyl group optionally having one or more substituents selected from the group α, a phosphate group optionally having one or more substituents selected from the group α, a phosphate group protected by a protecting group for nucleic acid synthesis, or —$P(R^3)R^4$ (wherein $R^3$ and $R^4$ each independently represent a hydroxy group, a hydroxy group protected by a protecting group for nucleic acid synthesis, a mercapto group, a mercapto group protected by a protecting group for nucleic acid synthesis, an amino group, an alkoxy group of 1 to 5 carbon atoms, an alkylthio group of 1 to 5 carbon atoms, a cyanoalkoxy group of 1 to 6 carbon atoms, or an amino group substituted with an alkyl group of 1 to 6 carbon atoms); and $R^5$ represents a hydrogen atom, a halogen atom, an optionally branched or cyclic alkyl group of 1 to 7 carbon atoms optionally substituted with an aryl group of 3 to 12 carbon atoms optionally containing a heteroatom, an aralkyl group having an aryl moiety of 3 to 12 carbon atoms optionally containing a heteroatom, or a silyl group.

X in formula (I) may be the nucleic acid base moiety as described above. For the application of the compound to a nucleic acid medicine, X is preferably a purine or pyrimidine base optionally having a substituent, and is preferably, for example, any of a 2-oxo-4-hydroxy-5-methyl-1,2-dihydropyrimidin-1-yl group (thyminyl group), a 2-oxo-4-amino-1,2-dihydropyrimidin-1-yl group (cytosinyl group), a 6-aminopurin-9-yl group (adeninyl group), a 2-amino-6-hydroxypurin-9-yl group (guaninyl group), a 4-amino-5-methyl-2-oxo-1,2-dihydropyrimidin-1-yl group, and a 2-oxo-4-hydroxy-1,2-dihydropyrimidin-1-yl group (uracilyl group) as shown in the following formulas, respectively:

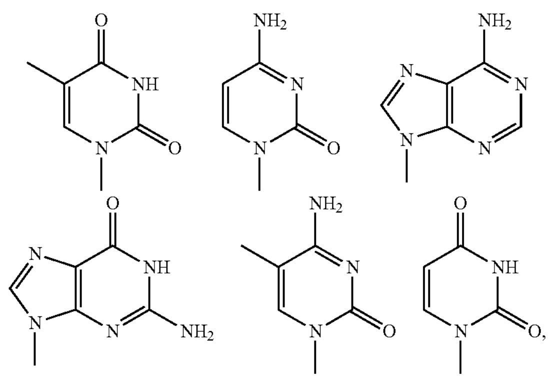

or any of these groups in which one or more of the amino or carbonyl groups are protected by a protecting group, or a tautomer thereof.

$R^1$ to $R^5$ in formula (I) can independently and appropriately be selected from the substituents as described above. The group represented by —$P(R^3)$ $R^4$ preferably includes a group represented by the formula —$P(OC_2H_4CN)(N(iPr)_2)$ and a group represented by the formula —$P(OCH_3)(N(iPr)_2)$, wherein iPr represents an isopropyl group.

The production method using a compound represented by formula (I) as a starting material may be carried out by, for example, intramolecular cyclizing a compound represented by formula (I) to produce a compound represented by formula (II) for use in the subsequent production step. An aspect of the present invention thus includes a method comprising at least intramolecularly cyclizing a compound represented by formula (I). This intramolecular cyclization step may also be called step A.

The intramolecular cyclization can be performed by a known method in the art, for example, addition reaction of an alcohol to an alkyne. The addition reaction is typically preferably performed by adding a base to the substrate in a solvent or neat, if necessary, under cooling or heating.

Examples of the base include alkoxides such as sodium methoxide, sodium ethoxide, sodium t-butoxide, lithium methoxide, lithium ethoxide, lithium t-butoxide, potassium methoxide, potassium ethoxide and potassium t-butoxide; carbonates such as sodium carbonate, potassium carbonate, sodium bicarbonate and potassium bicarbonate; organic metal reagents such as methyllithium, ethyllithium, n-butyllithium and methylmagnesium chloride; metal hydrides such as sodium hydride; metal amides such as lithium diisopropylamide, lithium hexamethyldisilazide, sodium hexamethyldisilazide and lithium dicyclohexylamide; and organic bases such as triethylamine, diisopropylethylamine, tributylamine, t-butylamine, N,N-dimethylaniline, N,N-diethylaniline, pyridine, 4-dimethylaminopyridine, pyrrolidine, piperidine, collidine, lutidine, morpholine, piperazine, diazabicycloundecene, diazabicyclononene and 1,4-diazabicyclo[2.2.2]octane. These bases may be used alone or in combination, and can be selected based on the type, reactivity and selectivity of the substrate.

The amount of the substrate, base, etc. used in the reaction, the reaction temperature, the reaction time, etc. can be appropriately selected in accordance with a known technique. For example, the reaction temperature is −80 to 200° C., the reaction time is 1 to 24 hours, and the amount of the base is 1.0 to 30 equivalents. Purification technique after the reaction is not limited.

The compound represented by formula (I) may be a commercially available product that has $R^1$ to $R^5$ and X as defined above or a compound having $R^1$ to $R^5$ and X as defined above prepared in accordance with a known method. For example, the compound represented by formula (I) may be a compound of formula (I) wherein X is a group having a uracil or cytosine skeleton optionally having a substituent (preferably a hydroxy group, an amino group, or a hydroxy or amino group protected by a protecting group), or a tautomer thereof. Specific structures thereof are shown below.

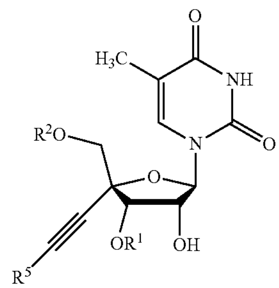

-continued

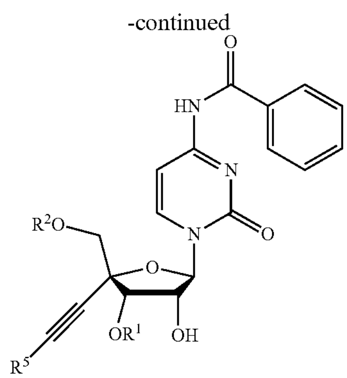

The compound represented by formula (I) may also be a compound of formula (I) wherein X is a group having a purine skeleton optionally having a substituent (preferably a hydroxy group, an amino group, or a hydroxy or amino group protected by a protecting group), or a tautomer thereof. Specific structures thereof are shown below.

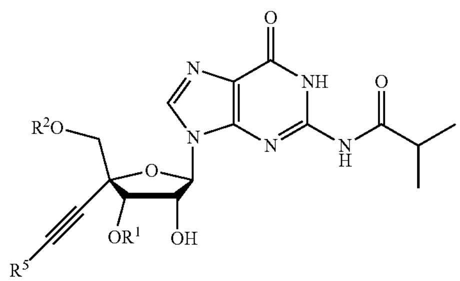

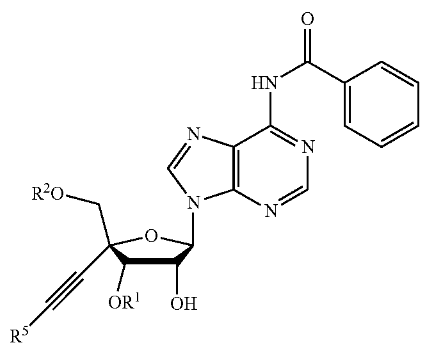

The compound represented by formula (I) herein may also be a compound of formula (I) wherein X is a 2,4-dioxo-1,2,3,4-tetrahydropyrimidin-1-yl group, $R^1$ and $R^2$ are benzyl groups, and $R^5$ is a hydrogen atom, and a compound of formula (I) wherein X is a 2,4-dioxo-1,2,3,4-tetrahydropyrimidin-1-yl group, and $R^1$, $R^2$ and $R^5$ are hydrogen atoms.

The compound represented by formula (I) can be prepared by deprotecting a compound represented by formula (IV) shown below. An aspect of the present invention thus includes the production method further comprising producing the compound represented by formula (I) by deprotecting a compound represented by formula (IV):

(IV)

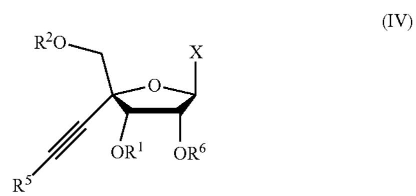

wherein

X represents a nucleic acid base moiety optionally having one or more substituents selected from the group α;

$R^1$ and $R^2$ each independently represent a hydrogen atom, a protecting group for a hydroxy group used in nucleic acid synthesis, an optionally branched or cyclic alkyl group of 1 to 7 carbon atoms, an optionally branched or cyclic alkenyl group of 2 to 7 carbon atoms, an aryl group of 3 to 10 carbon atoms optionally having one or more substituents selected from the group α and optionally containing a heteroatom, an aralkyl group having an aryl moiety of 3 to 12 carbon atoms optionally having one or more substituents selected from the group α and optionally containing a heteroatom, an acyl group optionally having one or more substituents selected from the group α, a silyl group optionally having one or more substituents selected from the group α, a phosphate group optionally having one or more substituents selected from the group α, a phosphate group protected by a protecting group for nucleic acid synthesis, or —$P(R^3)R^4$ (wherein $R^3$ and $R^4$ each independently represent a hydroxy group, a hydroxy group protected by a protecting group for nucleic acid synthesis, a mercapto group, a mercapto group protected by a protecting group for nucleic acid synthesis, an amino group, an alkoxy group of 1 to 5 carbon atoms, an alkylthio group of 1 to 5 carbon atoms, a cyanoalkoxy group of 1 to 6 carbon atoms, or an amino group substituted with an alkyl group of 1 to 6 carbon atoms);

$R^5$ represents a hydrogen atom, a halogen atom, an optionally branched or cyclic alkyl group of 1 to 7 carbon atoms optionally substituted with an aryl group of 3 to 12 carbon atoms optionally containing a heteroatom, an aralkyl group having an aryl moiety of 3 to 12 carbon atoms optionally containing a heteroatom, or a silyl group; and $R^6$ represents a protecting group for a hydroxy group used in nucleic acid synthesis.

In a preferred aspect of the invention, the compound represented by formula (I) is produced by deprotecting a compound represented by formula (IV) wherein $R^6$ represents a removable group.

$R^1$ to $R^6$ and X in formula (IV) can independently and appropriately be selected from the substituents as described above, and are selected depending on the desired structure of the compound represented by formula (I).

The deprotection can be performed by a known method in the art selected depending on the type of protecting group. For example, when $R^6$ is an acetyl group, the compound is preferably dissolved in an organic solvent with addition of a base, and is allowed to react, if necessary, under cooling or heating. For example, the reaction temperature is −80 to 200° C., the reaction time is 0.1 to 24 hours, and the amount of the base is 1.0 to 30 equivalents.

The compound represented by formula (IV) may be a commercially available product that has $R^1$ to $R^6$ and X as defined above, or a compound having $R^1$ to $R^6$ and X as defined above prepared in accordance with a known method. For example, the compound represented by formula (IV) may be a compound of formula (IV) wherein $R^6$ is an acetyl group, or a compound of formula (IV) wherein X is a group having a uracil or cytosine skeleton optionally having a substituent (preferably a hydroxy group, an amino group, or a hydroxy or amino group protected by a protecting group), or a tautomer thereof. Specific structures thereof are shown below.

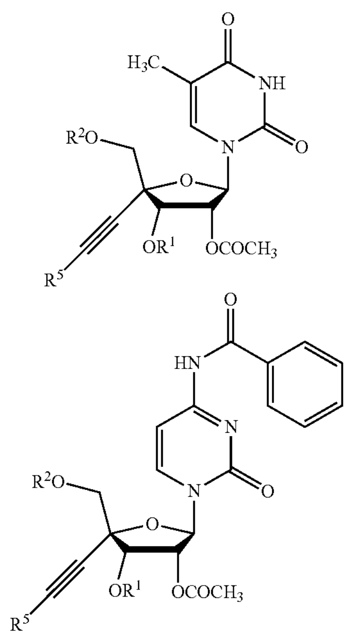

The compound represented by formula (IV) may also be a compound of formula (IV) wherein X is a group having a purine skeleton optionally having a substituent (preferably a hydroxy group, an amino group, or a hydroxy or amino group protected by a protecting group), or a tautomer thereof. Specific structures thereof are shown below.

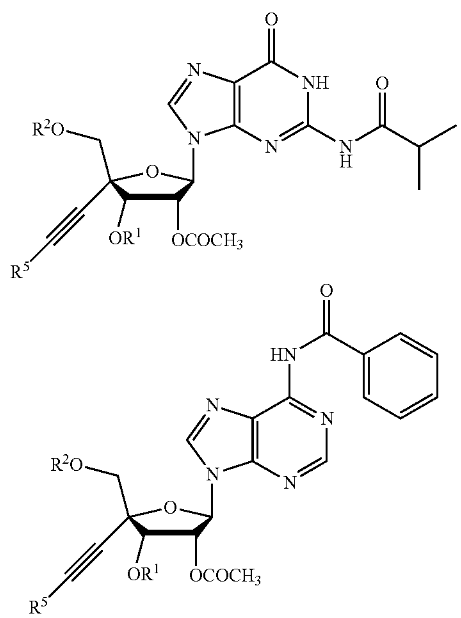

The compound represented by formula (IV) herein may be a compound of formula (IV) wherein X is a 2,4-dioxo-1,2,3,4-tetrahydropyrimidin-1-yl group, $R^1$ and $R^2$ are benzyl groups, and $R^6$ is an acetyl group, and a compound of formula (IV) wherein X is a 2,4-dioxo-1,2,3,4-tetrahydro-pyrimidin-1-yl group, and $R^1$, $R^2$ and $R^6$ are acetyl groups.

The compound represented by formula (I) can be prepared from a compound represented by formula (V) as a starting material. An aspect of the invention thus includes a production method comprising producing the compound represented by formula (I) using, as a starting material, a compound represented by formula (V):

(V)

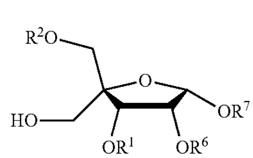

wherein $R^1$ and $R^2$ each independently represent a hydrogen atom, a protecting group for a hydroxy group used in nucleic acid synthesis, an optionally branched or cyclic alkyl group of 1 to 7 carbon atoms, an optionally branched or cyclic alkenyl group of 2 to 7 carbon atoms, an aryl group of 3 to 10 carbon atoms optionally having one or more substituents selected from a group α and optionally containing a heteroatom (wherein the group α consists of a hydroxy group, a hydroxy group protected by a protecting group for nucleic acid synthesis, an alkyl group of 1 to 5 carbon atoms, an alkoxy group of 1 to 5 carbon atoms, a mercapto group, a mercapto group protected by a protecting group for nucleic acid synthesis, an alkylthio group of 1 to 5 carbon atoms, an amino group, an amino group protected by a protecting group for nucleic acid synthesis, an amino group substituted with an alkyl group of 1 to 5 carbon atoms, and a halogen atom), an aralkyl group having an aryl moiety of 3 to 12 carbon atoms optionally having one or more substituents selected from the group α and optionally containing a heteroatom, an acyl group optionally having one or more substituents selected from the group α, a silyl group optionally having one or more substituents selected from the group α, a phosphate group optionally having one or more substituents selected from the group α, a phosphate group protected by a protecting group for nucleic acid synthesis, or $—P(R^3)R^4$ (wherein $R^3$ and $R^4$ each independently represent a hydroxy group, a hydroxy group protected by a protecting group for nucleic acid synthesis, a mercapto group, a mercapto group protected by a protecting group for nucleic acid synthesis, an amino group, an alkoxy group of 1 to 5 carbon atoms, an alkylthio group of 1 to 5 carbon atoms, a cyanoalkoxy group of 1 to 6 carbon atoms, or an amino group substituted with an alkyl group of 1 to 6 carbon atoms); and $R^6$ and $R^7$ each independently represent a protecting group for a hydroxy group used in nucleic acid synthesis, an optionally branched or cyclic alkyl group of 1 to 7 carbon atoms, an optionally branched or cyclic alkenyl group of 2 to 7 carbon atoms, an aryl group of 3 to 10 carbon atoms optionally having one or more substituents selected from the group α and optionally containing a heteroatom, an aralkyl group having an aryl moiety of 3 to 12 carbon atoms optionally having one or more substituents selected from the group α and optionally containing a heteroatom, an acyl group optionally having one or more substituents selected from the group α, a silyl group optionally having one or more substituents selected from the group α, a phosphate group optionally having one or more substituents selected from the group α, or a phosphate group protected by a protecting group for nucleic acid synthesis, or $R^6$ and $R^7$ are joined together to form —C($R^8$)($R^9$)— (wherein $R^8$ and $R^9$ each independently represent a hydrogen atom, an optionally branched or cyclic alkyl group of 1 to 7 carbon atoms optionally substituted with an aryl group of 3 to 12 carbon atoms optionally containing a heteroatom, or an aralkyl group having an aryl moiety of 3 to 12 carbon atoms optionally containing a heteroatom).

$R^1$ to $R^4$, $R^6$ and $R^7$ in formula (V) can independently and appropriately be selected from the substituents as described above, and are selected depending on the desired structure of the compound represented by formula (I).

The preparation of the compound of formula (I) from the compound of formula (V) may be performed in accordance with a known method in the art, or alternatively, may be performed as described below for simplifying the production process.

Specifically, for example, the compound of formula (V) is first allowed to react in the presence of a reacting agent to prepare a 4-formyl compound represented by formula (VI). The reaction temperature is preferably −80 to 200° C. and the reaction time is preferably 0.1 to 24 hours.

(VI)

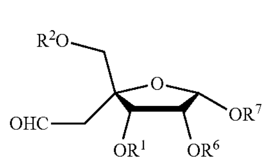

wherein $R^1$ and $R^2$ each independently represent a hydrogen atom, a protecting group for a hydroxy group used in nucleic acid synthesis, an optionally branched or cyclic alkyl group of 1 to 7 carbon atoms, an optionally branched or cyclic alkenyl group of 2 to 7 carbon atoms, an aryl group of 3 to 10 carbon atoms optionally having one or more substituents selected from a group α and optionally containing a heteroatom (wherein the group α consists of a hydroxy group, a hydroxy group protected by a protecting group for nucleic acid synthesis, an alkyl group of 1 to 5 carbon atoms, an alkoxy group of 1 to 5 carbon atoms, a mercapto group, a mercapto group protected by a protecting group for nucleic acid synthesis, an alkylthio group of 1 to 5 carbon atoms, an amino group, an amino group protected by a protecting group for nucleic acid synthesis, an amino group substituted with an alkyl group of 1 to 5 carbon atoms, and a halogen atom), an aralkyl group having an aryl moiety of 3 to 12 carbon atoms optionally having one or more substituents selected from the group α and optionally containing a heteroatom, an acyl group optionally having one or more substituents selected from the group α, a silyl group optionally having one or more substituents selected from the group α, a phosphate group optionally having one or more substituents selected from the group α, a phosphate group protected by a protecting group for nucleic acid synthesis, or —P($R^3$)$R^4$ (wherein $R^3$ and $R^4$ each independently represent a hydroxy group, a hydroxy group protected by a protecting group for nucleic acid synthesis, a mercapto group, a mercapto group protected by a protecting group for nucleic acid synthesis, an amino group, an alkoxy group of 1 to 5 carbon atoms, an alkylthio group of 1 to 5 carbon atoms, a cyanoalkoxy group of 1 to 6 carbon atoms, or an amino group substituted with an alkyl group of 1 to 6 carbon atoms); and $R^6$ and $R^7$ each independently represent a protecting group for a hydroxy group used in nucleic acid synthesis, an optionally branched or cyclic alkyl group of 1 to 7 carbon atoms, an optionally branched or cyclic alkenyl group of 2 to 7 carbon atoms, an aryl group of 3 to 10 carbon atoms optionally having one or more substituents selected from the group α and optionally containing a heteroatom, an aralkyl group having an aryl moiety of 3 to 12 carbon atoms optionally having one or more substituents selected from the group α and optionally containing a heteroatom, an acyl group optionally having one or more substituents selected from the group α, a silyl group optionally having one or more substituents selected from the group α, a phosphate group optionally having one or more substituents selected from the group α, or a phosphate group protected by a protecting group for nucleic acid synthesis, or $R^6$ and $R^7$ are joined together to form —C($R^8$)($R^9$)— (wherein $R^8$ and $R^9$ each independently represent a hydrogen atom, an optionally branched or cyclic alkyl group of 1 to 7 carbon atoms optionally substituted with an aryl group of 3 to 12 carbon atoms optionally containing a heteroatom, or an aralkyl group having an aryl moiety of 3 to 12 carbon atoms optionally containing a heteroatom).

The reacting agent may be a reacting agent used in a known oxidation reaction. For example, the reacting agent may be a known oxidant, including Dess-Martin reagent, 2,2,6,6-tetramethylpiperidin-1-oxyl radical/sodium hypochlorite, oxalyl chloride/dimethyl sulfoxide, acetic anhydride/dimethyl sulfoxide, trifluoroacetic anhydride/dimethyl sulfoxide, dicyclohexylcarbodiimide/dimethyl sulfoxide, 1-(3-dimethylaminopropyl)-3-ethylcarbodiimide/dimethyl sulfoxide, and a sulfur trioxide-pyridine complex/dimethyl sulfoxide. Preferred is a sulfur trioxide-pyridine complex/dimethyl sulfoxide, which can achieve mild reaction conditions. The amount of the reacting agent is preferably 1.0 to 20 equivalents.

$R^1$ to $R^4$, $R^6$ and $R^7$ in formula (VI) can independently and appropriately be selected from the substituents as described above, and are selected depending on the desired structure of the compound represented by formula (I).

Then, the prepared 4-formyl compound is allowed to react in accordance with a known method to prepare a 4-dibromoethenyl compound.

$R^5$ is then introduced into the 4-dibromoethenyl compound to prepare a 4-ethynyl compound having $R^5$. Alternatively, the 4-dibromoethenyl compound is converted into a 4-ethynyl compound, and $R^5$ is introduced into the 4-ethynyl compound to prepare a 4-ethynyl compound having $R^5$.

To a solution of the 4-ethynyl compound in acetic acid and acetic anhydride, concentrated sulfuric acid is added to synthesize a compound represented by formula (VII) below. A nucleic acid base moiety is then introduced at position 1 of the compound to prepare a compound of formula (I). For the reaction for preparation of the compound of formula (VII), the reaction temperature is preferably 0 to 40° C., the reaction time is preferably 0.1 to 24 hours, and the amount of concentrated sulfuric acid is preferably 0.01 to 1.0 equivalent. These reaction conditions allow for reduction of the number of reaction steps from two steps to one step, thereby increasing the efficiency of synthesis.

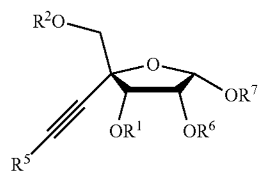

(VII)

wherein $R^1$ and $R^2$ each independently represent a hydrogen atom, a protecting group for a hydroxy group used in nucleic acid synthesis, an optionally branched or cyclic alkyl group of 1 to 7 carbon atoms, an optionally branched or cyclic alkenyl group of 2 to 7 carbon atoms, an aryl group of 3 to 10 carbon atoms optionally having one or more substituents selected from a group α and optionally containing a heteroatom (wherein the group α consists of a hydroxy group, a hydroxy group protected by a protecting group for nucleic acid synthesis, an alkyl group of 1 to 5 carbon atoms, an alkoxy group of 1 to 5 carbon atoms, a mercapto group, a mercapto group protected by a protecting group for nucleic acid synthesis, an alkylthio group of 1 to 5 carbon atoms, an amino group, an amino group protected by a protecting group for nucleic acid synthesis, an amino group substituted with an alkyl group of 1 to 5 carbon atoms, and a halogen atom), an aralkyl group having an aryl moiety of 3 to 12 carbon atoms optionally having one or more substituents selected from the group α and optionally containing a heteroatom, an acyl group optionally having one or more substituents selected from the group α, a silyl group optionally having one or more substituents selected from the group α, a phosphate group optionally having one or more substituents selected from the group α, a phosphate group protected by a protecting group for nucleic acid synthesis, or —$P(R^3)R^4$ (wherein $R^3$ and $R^4$ each independently represent a hydroxy group, a hydroxy group protected by a protecting group for nucleic acid synthesis, a mercapto group, a mercapto group protected by a protecting group for nucleic acid synthesis, an amino group, an alkoxy group of 1 to 5 carbon atoms, an alkylthio group of 1 to 5 carbon atoms, a cyanoalkoxy group of 1 to 6 carbon atoms, or an amino group substituted with an alkyl group of 1 to 6 carbon atoms);

$R^5$ represents a hydrogen atom, a halogen atom, an optionally branched or cyclic alkyl group of 1 to 7 carbon atoms optionally substituted with an aryl group of 3 to 12 carbon atoms optionally containing a heteroatom, an aralkyl group having an aryl moiety of 3 to 12 carbon atoms optionally containing a heteroatom, or a silyl group; and $R^6$ and $R^7$ each independently represent a protecting group for a hydroxy group used in nucleic acid synthesis, an optionally branched or cyclic alkyl group of 1 to 7 carbon atoms, an optionally branched or cyclic alkenyl group of 2 to 7 carbon atoms, an aryl group of 3 to 10 carbon atoms optionally having one or more substituents selected from the group α and optionally containing a heteroatom, an aralkyl group having an aryl moiety of 3 to 12 carbon atoms optionally having one or more substituents selected from the group α and optionally containing a heteroatom, an acyl group optionally having one or more substituents selected from the group α, a silyl group optionally having one or more substituents selected from the group α, a phosphate group optionally having one or more substituents selected from the group α, or a phosphate group protected by a protecting group for nucleic acid synthesis.

$R^1$ to $R^7$ in formula (VII) can independently and appropriately be selected from the substituents as described above, and are selected depending on the desired structure of the compound represented by formula (I).

The compound represented by formula (V) may be a commercially available product that has $R^1$ to $R^4$, $R^6$ and $R^7$ as defined above, or a compound having $R^1$ to $R^4$, $R^6$ and $R^7$ as defined above prepared in accordance with a known method.

The resulting compound represented by formula (I) may be appropriately purified by a known technique.

In step A as described above, the compound represented by formula (I) is converted into the compound represented by formula (II):

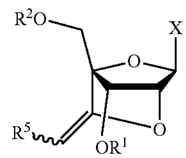

(II)

wherein

X represents a nucleic acid base moiety optionally having one or more substituents selected from the group α;

$R^1$ and $R^2$ each independently represent a hydrogen atom, a protecting group for a hydroxy group used in nucleic acid synthesis, an optionally branched or cyclic alkyl group of 1 to 7 carbon atoms, an optionally branched or cyclic alkenyl group of 2 to 7 carbon atoms, an aryl group of 3 to 10 carbon atoms optionally having one or more substituents selected from the group α and optionally containing a heteroatom, an aralkyl group having an aryl moiety of 3 to 12 carbon atoms optionally having one or more substituents selected from the group α and optionally containing a heteroatom, an acyl group optionally having one or more substituents selected from the group α, a silyl group optionally having one or more substituents selected from the group α, a phosphate group optionally having one or more substituents selected from the group α, a phosphate group protected by a protecting group for nucleic acid synthesis, or —$P(R^3)R^4$ (wherein $R^3$ and $R^4$ each independently represent a hydroxy group, a hydroxy group protected by a protecting group for nucleic acid synthesis, a mercapto group, a mercapto group protected by a protecting group for nucleic acid synthesis, an amino group, an alkoxy group of 1 to 5 carbon atoms, an alkylthio group of 1 to 5 carbon atoms, a cyanoalkoxy group of 1 to 6 carbon atoms, or an amino group substituted with an alkyl group of 1 to 6 carbon atoms); and $R^5$ represents a hydrogen atom, a halogen atom, an optionally branched or cyclic alkyl group of 1 to 7 carbon atoms optionally substituted with an aryl group of 3 to 12 carbon atoms optionally containing a heteroatom, an aralkyl group having an aryl moiety of 3 to 12 carbon atoms optionally containing a heteroatom, or a silyl group.

The substituents in formula (II) are selected as appropriate for the compound represented by formula (I) used in the reaction.

The preparation of a compound represented by formula (III) from the compound represented by formula (II) will be described below. Specifically, a compound represented by formula (III) can be prepared by cyclopropanating the compound represented by formula (II). An aspect of the invention thus includes a method comprising cyclopropanating a compound represented by formula (II). This cyclopropanation step may also be called step B below.

(III)

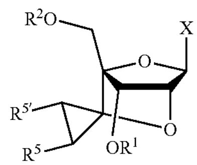

wherein

X represents a nucleic acid base moiety optionally having one or more substituents selected from the group α;

$R^1$ and $R^2$ each independently represent a hydrogen atom, a protecting group for a hydroxy group used in nucleic acid synthesis, an optionally branched or cyclic alkyl group of 1 to 7 carbon atoms, an optionally branched or cyclic alkenyl group of 2 to 7 carbon atoms, an aryl group of 3 to 10 carbon atoms optionally having one or more substituents selected from the group α and optionally containing a heteroatom, an aralkyl group having an aryl moiety of 3 to 12 carbon atoms optionally having one or more substituents selected from the group α and optionally containing a heteroatom, an acyl group optionally having one or more substituents selected from the group α, a silyl group optionally having one or more substituents selected from the group α, a phosphate group optionally having one or more substituents selected from the group α, a phosphate group protected by a protecting group for nucleic acid synthesis, or $—P(R^3)R^4$ (wherein $R^3$ and $R^4$ each independently represent a hydroxy group, a hydroxy group protected by a protecting group for nucleic acid synthesis, a mercapto group, a mercapto group protected by a protecting group for nucleic acid synthesis, an amino group, an alkoxy group of 1 to 5 carbon atoms, an alkylthio group of 1 to 5 carbon atoms, a cyanoalkoxy group of 1 to 6 carbon atoms, or an amino group substituted with an alkyl group of 1 to 6 carbon atoms); and $R^5$ and $R^{5'}$ represent a hydrogen atom, an optionally branched or cyclic alkyl group of 1 to 7 carbon atoms optionally substituted with an aryl group of 3 to 12 carbon atoms optionally containing a heteroatom, or an aralkyl group having an aryl moiety of 3 to 12 carbon atoms optionally containing a heteroatom.

The cyclopropanation can be performed by, for example, the Simmons-Smith reaction. This reaction is performed in the presence of a zinc carbenoid. Instead of zinc, diethylzinc or a $CH_2N_2—ZnI_2$ reagent can be used in modified version of the reaction. The amount of a zinc carbenoid to be reacted is, for example, preferably 1.0 to 20 equivalents.

The progress of the cyclopropanation reaction in step B varies with the type of a zinc carbenoid. To address this, the reaction may be performed in the presence of an organic acid. The presence of an organic acid inhibits precipitation and side reactions. The organic acid may be any known organic acid, and is preferably formic acid, acetic acid, dichloroacetic acid, trichloroacetic acid, trifluoroacetic acid, diphenylphosphoric acid, tosylic acid, phenol, or the like. The amount of the organic acid is preferably, for example, 0.5 to 2.0 equivalents relative to that of a zinc carbenoid.

The reaction in the presence of an organic acid as described above can be applied to any compound represented by formula (II), but the compound of formula (II) undergoing the reaction is preferably a compound of formula (II) wherein X has a purine skeleton, or a tautomer thereof.

The compound represented by formula (II) to be subjected to the reaction may be a commercially available compound or a compound prepared in accordance with a known method. The compound represented by formula (II) to be subjected to the reaction may be a compound prepared in accordance with step A as described above.

The compound represented by formula (II) may be a compound of formula (II) wherein X is a group having a uracil or cytosine skeleton optionally having a substituent (preferably a hydroxy group, an amino group, or a hydroxy or amino group protected by a protecting group), or a tautomer thereof. Specific structures thereof are shown below.

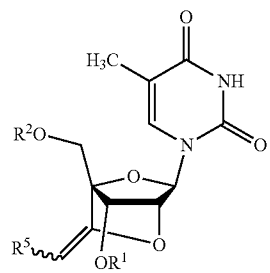

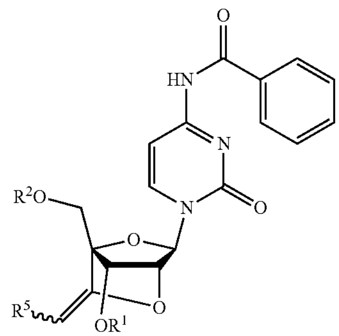

The compound represented by formula (II) may also be a compound of formula (II) wherein X is a group having a purine skeleton having a substituent (preferably a hydroxy group, an amino group, or a hydroxy or amino group protected by a protecting group), or a tautomer thereof. Specific structures thereof are shown below.

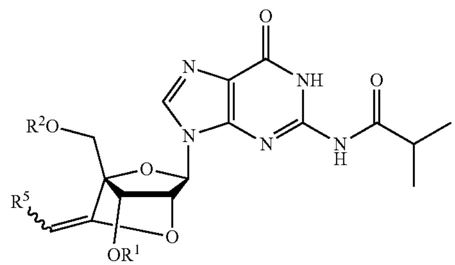

-continued

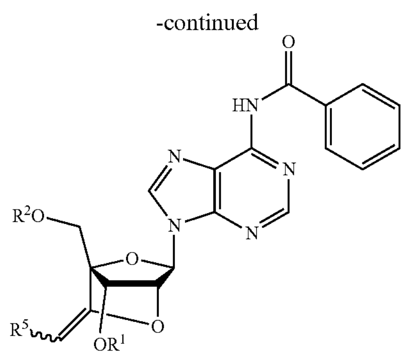

The compound represented by formula (II) herein may also be a compound of formula (II) wherein X is a 2,4-dioxo-1,2,3,4-tetrahydropyrimidin-1-yl group, $R^1$ is a naphthyl group, $R^2$ is a benzyl group, and $R^5$ is a hydrogen atom, and a compound of formula (II) wherein X is a 2,4-dioxo-1,2,3,4-tetrahydropyrimidin-1-yl group, $R^1$ is a naphthyl group, and $R^2$ and $R^5$ are hydrogen atoms.

For improving the yield, for example, when the compound represented by formula (II) to be subjected to cyclopropanation has an active reactive group at the position X, a part or the whole of the active reactive group may be protected by a known protective group. For example, when X is a compound having a purine skeleton protected by a protecting group, side reactions occurring at the position X as a reactive site are inhibited, thereby improving the yield.

The compound obtained in step B can be appropriately purified by a known technique. For example, for ease of carrying out post-treatment after the reaction, the reaction mixture may be post-treated with ammonia. Post-treatment with ammonia facilitates the removal of residues of the reagents and enables the appropriate use of the purified product.

The post-treatment can be applied to any compound represented by formula (III), but the compound of formula (III) undergoing the post-treatment is preferably a compound of formula (III) wherein X has a pyrimidine skeleton. When such a compound is subjected to the post-treatment, the border between the organic and aqueous layers is clearly visible, and the organic and aqueous layers are efficiently separated.

In step B as described above, the compound represented by formula (III) can be prepared from the compound represented by formula (II).

In an aspect of the present invention, when the compound represented by formula (II) is prepared in accordance with step A, the method for producing a compound represented by formula (III) according to the present invention may include at least steps A and B. The method may further include preparing a compound represented by formula (I) used in step A by the method as described above. The compound represented by formula (III) may be a compound of formula (III) wherein X is a compound having a group (a hydroxy group, a mercapto group, an amino group, etc.) protected by a protecting group used in nucleic acid synthesis, or may be a compound of formula (III) wherein part or all of the protected groups are deprotected. The deprotection of groups (a hydroxy group, a mercapto group, an amino group, etc.) protected by a protecting group used in nucleic acid synthesis may be performed by a known deprotection method [for example, treatment with a weak acid (for example, carboxylic acid, silica gel, etc.)].

Various compounds represented by formula (III) can be prepared in the present invention. For example, a compound represented by formula (VII) can be prepared as a shared structure, and various desired nucleic acid moieties can be introduced into the compound. In this manner, efficient preparation is achieved.

The compound represented by formula (III) prepared by the present invention can be converted into an amidite in accordance with a known method. The resulting amidite derivative is expected to be useful as a starting material for synthesis of a nucleic acid medicine (an antisense nucleic acid medicine) capable of inhibiting the functions of a specific gene to treat a disease.

EXAMPLES

The present invention will be described in more detail below with reference to Examples, but the present invention is not limited thereto. The room temperature (RT) as used herein means 15 to 35° C.

Example 1: Synthesis of Shared Intermediate Compounds

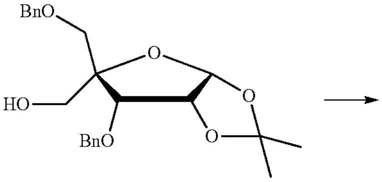

1

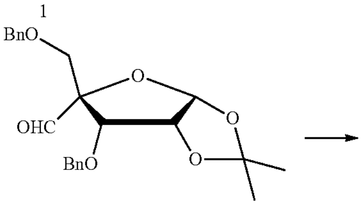

2

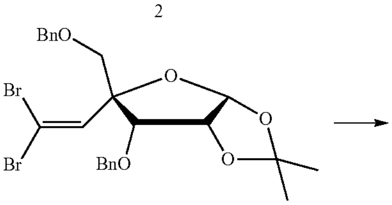

3

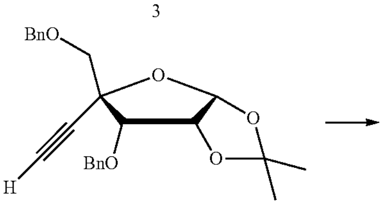

4

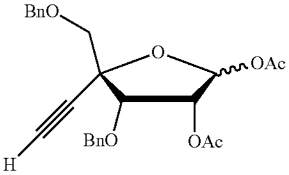

5

(1) Synthesis of Compound 2

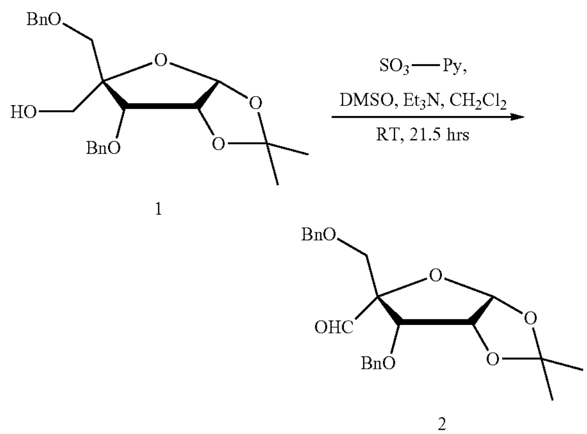

1

2

Dimethyl sulfoxide (32 mL, 0.45 mol, 9.0 eq.) and triethylamine (27.7 mL, 0.200 mol, 4.0 eq.) were added to a solution of compound 1 (20 g, 50 mmol) in dichloromethane anhydride (167 mL). The mixture was cooled to an internal temperature of 7° C., and sulfur trioxide-pyridine complex (15.9 g, 0.100 mol, 2.0 eq.) was gradually added. The mixture was stirred at room temperature for 21.5 hours. Tap water (300 mL) was added to the reaction mixture. The reaction mixture was subjected to extraction with a mixed solvent of ethyl acetate (200 mL) and hexane (100 mL) and separated into an organic layer I and an aqueous layer I. The organic layer I was washed with a mixture of tap water (200 mL) and a saturated aqueous ammonium chloride solution (100 mL) to give an organic layer II and an aqueous layer II. The organic layer II was further washed with tap water (100 mL) and a saturated aqueous ammonium chloride solution (100 mL) to give an organic layer III and an aqueous layer III. The aqueous layers II and III were combined, subjected to extraction with ethyl acetate (100 mL), and washed with tap water (100 mL) to give an organic layer IV. The organic layers III and IV were combined, washed with a saturated brine solution (100 mL), and dried over anhydrous sodium sulfate. The solvent was evaporated under reduced pressure to give a crude product of compound 2 (20.24 g) as a pale orange oily liquid. The resulting compound 2 was used in the subsequent step without further purification. The yield was quantitative.

1H NMR (600 MHz, $CDCl_3$) δ: 9.91 (s, 1H), 7.37-7.26 (m, 8H), 7.25-7.21 (m, 2H), 5.84 (d, J=3.5 Hz, 1H), 4.71 (d, J=12.0 Hz, 1H), 4.59 (d, J=12.0 Hz, 1H), 4.60 (dd, J=4.4, 3.5 Hz, 1H), 4.52 (d, J=12.0 Hz, 1H), 4.46 (d, J=12.0 Hz, 1H), 4.37 (d, J=4.4 Hz, 1H), 3.67 (d, J=11.4 Hz, 1H), 3.61 (d, J=11.4 Hz, 1H), 1.60 (s, 3H), 1.35 (s, 3H)

(2) Synthesis of Compound 3

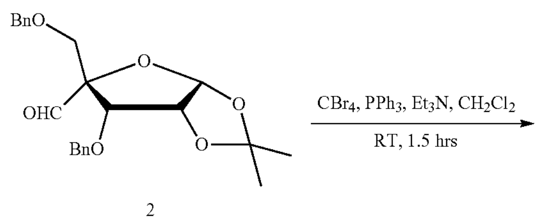

2

-continued

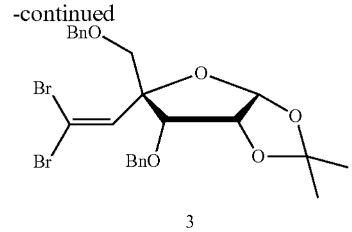

3

The crude product of compound 2 (20.24 g) obtained in the previous step was azeotropically distilled with toluene. The residue was dissolved in dichloromethane anhydride (250 mL), and carbon tetrabromide (33.1 g, 100 mmol, 2.0 eq.) was added. Triphenylphosphine (52.4 g, 200 mmol, 4.0 eq.) was added to the mixture at an internal temperature of 20° C. or lower, and the mixture was stirred at room temperature for 1.5 hours. Triethylamine (41.5 mL, 300 mmol, 6.0 eq.) was added to the mixture at an internal temperature of 25° C. or lower, and the mixture was further stirred for 2 hours. Hexane (200 mL) was added to the reaction mixture, and the reaction mixture was cooled on ice. The insoluble matter was filtered off, and the filtrate was washed with ethyl acetate and dichloromethane (50 mL). The washing solution and the filtrate were combined, and evaporated under reduced pressure. The residue was introduced into a silica gel pad (silica gel: 100 g) using a mixture of dichloromethane/hexane=1/1 (v/v), and eluted with hexane/ethyl acetate=1/2 (v/v) (300 mL) and then with ethyl acetate (400 mL). The eluate was concentrated under reduced pressure, and the residue was suspended in and washed with hexane/ethyl acetate=1/1 (v/v) (200 mL), and the insoluble matter was filtered off. The mother liquid was concentrated under reduced pressure, and the residue was suspended in and washed with hexane/ethyl acetate=2/1 (v/v) (100 mL) and the insoluble matter was filtered off. The mother liquid was concentrated under reduced pressure to give a mixture of compound 3 and triphenylphosphine oxide (28.1 g) as a brown viscous liquid. The resulting compound 3 was used in the subsequent step without further purification. The yield was quantitative.

1H NMR (600 MHz, $CDCl_3$) δ: 7.39-7.26 (m, 8H), 7.26-7.22 (m, 2H), 7.11 (s, 1H), 5.76 (d, J=4.1 Hz, 1H), 4.72 (d, J=12.0 Hz, 1H), 4.60 (d, J=12.0 Hz, 1H), 4.59 (d, J=12.0 Hz, 1H), 4.53 (dd, J=4.7, 4.1 Hz, 1H), 4.42 (d, J=12.0 Hz, 1H), 4.21 (d, J=4.7 Hz, 1H), 3.83 (d, J=11.4 Hz, 1H), 3.40 (d, J=11.4 Hz, 1H), 1.59 (s, 3H), 1.30 (s, 3H)

(3) Synthesis of Compound 4

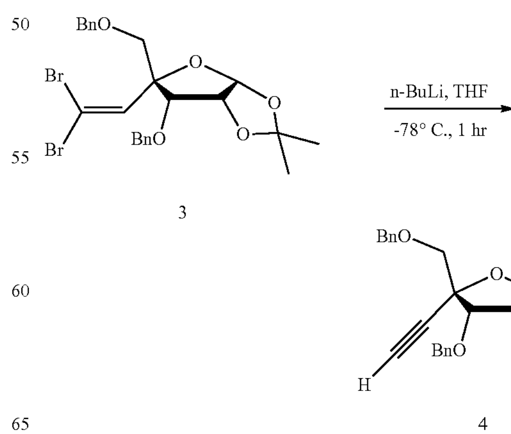

3

4

The mixture of compound 3 and triphenylphosphine oxide (28.1 g) obtained in the previous step was azeotropically distilled with anhydrous tetrahydrofuran under nitrogen atmosphere, and the residue was dissolved in anhydrous tetrahydrofuran. Then, n-butyllithium (a 1.6 M solution in hexane, 71 mL, 110 mmol, 2.2 eq.) was added dropwise over 30 minutes at an internal temperature of −50° C. or lower, and the mixture was stirred at −70° C. for 1 hour. Water (100 mL) was added at the same temperature. Ethyl acetate (400 mL), tap water (100 mL) and a saturated brine solution (100 mL) were added and extraction was performed to give an organic layer I and an aqueous layer I. The aqueous layer I was subjected to extraction with ethyl acetate (100 mL) to give an organic layer II. The organic layers I and II were combined, washed successively with a saturated aqueous ammonium chloride solution (200 mL) and a saturated brine solution (100 mL), dried over anhydrous sodium sulfate, and concentrated under reduced pressure to give a crude product of compound 4 (21.2 g) as a brown liquid. The resulting compound 4 was used in the subsequent step without further purification. The yield was quantitative.

1H NMR (600 MHz, $CDCl_3$) δ: 7.41-7.27 (m, 8H), 7.22-7.19 (m, 2H), 5.70 (d, J=3.5 Hz, 1H), 4.77 (d, J=12.6 Hz, 1H), 4.69 (d, J=12.6 Hz, 1H), 4.55 (dd, J=4.7, 3.5 Hz, 1H), 4.52 (d, J=12.3 Hz, 1H), 4.44 (d, J=12.3 Hz, 1H), 4.16 (d, J=4.7 Hz, 1H), 3.70 (d, J=11.2 Hz, 1H), 3.55 (d, J=11.3 Hz, 1H), 2.65 (s, 1H), 1.72 (s, 3H), 1.33 (s, 3H)

(4) Synthesis of Compound 5

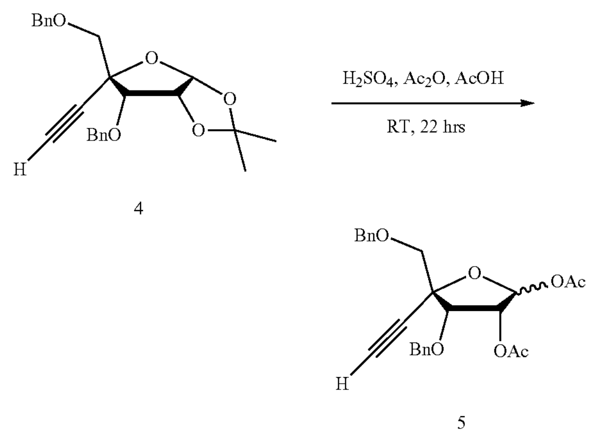

4

5

A solution of concentrated sulfuric acid (255 mg, 2.60 mmol, 0.05 eq.) in acetic acid (60 mL, 1.0 mol) was added to a solution of the crude product of compound 4 (21.0 g) of the previous step in acetic anhydride (94.5 mL, 1.00 mol), and the mixture was stirred at room temperature for 7 hours. Acetic acid (57.2 mL, 1.00 mol) was added to the reaction mixture, and the mixture was further stirred for 15 hours. The reaction mixture was poured into a mixture of ethyl acetate (200 mL) and a saturated sodium bicarbonate solution (300 mL) under ice cooling, and the aqueous layer was extracted twice with ethyl acetate (100 mL). The combined organic layers were washed successively with a saturated sodium bicarbonate solution (100 mL), tap water (100 mL) and a saturated brine solution (100 mL), dried over anhydrous sodium sulfate, and concentrated under reduced pressure. The residue was purified by silica gel column chromatography (silica gel: 100 g, hexane/ethyl acetate=1/0 to 2/1 (v/v)) to give compound 5 (17.7 g, 40.4 mmol, overall yield in four steps: 82%) as an orange viscous liquid.

1H NMR (600 MHz, $CDCl_3$) δ: 7.36-7.27 (m, 8H), 7.26-7.16 (m, 2H), 6.19 (s, 1H), 5.29 (d, J=4.7 Hz, 1H), 4.72 (d, J=12.2 Hz, 1H), 4.59 (d, J=12.2 Hz, 1H), 4.50 (d, J=11.9 Hz, 1H), 4.46 (d, J=4.7 Hz, 1H), 4.39 (d, J=11.9 Hz, 1H), 3.67 (d, J=11.2 Hz, 1H), 3.56 (d, J=11.2 Hz, 1H), 2.65 (s, 1H), 2.15 (s, 3H), 1.80 (s, 3H)

Example 2: Synthesis of T-Dibenzyl Derivative

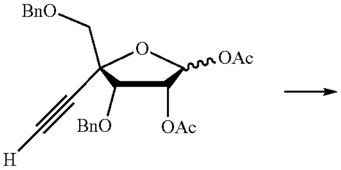

5

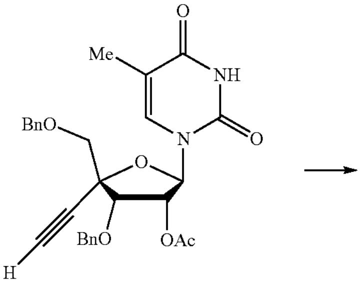

6

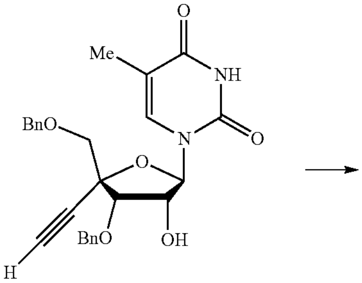

7

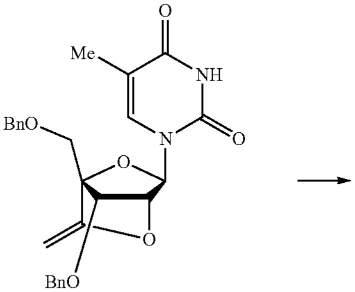

8

-continued

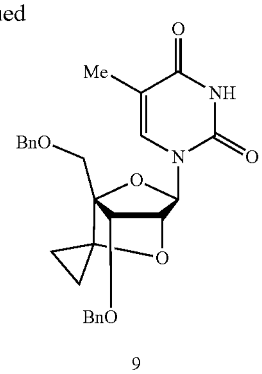

9

(1) Synthesis of compound 6

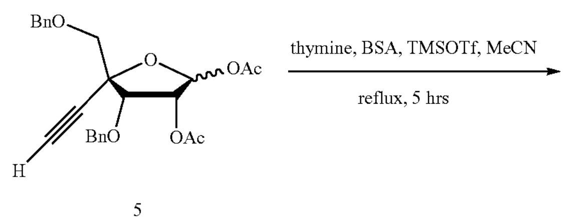

5

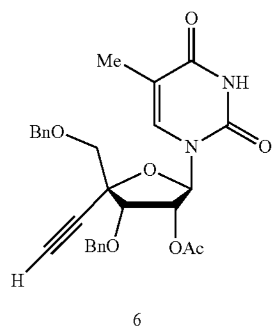

6

Thymine (3.79 g, 30.1 mmol, 3.0 eq.), N,O-bis(trimethylsilyl)acetamide (7.15 mL, 49.9 mmol, 5.0 eq.) and trimethylsilyl triflate (2.71 mL, 15.0 mmol, 1.5 eq.) were successively added to a solution of compound 5 (4.38 g, 10.0 mmol) in anhydrous acetonitrile (50 mL) under nitrogen atmosphere, and the mixture was heated to reflux for 5 hours. The reaction mixture was left to cool down to room temperature, poured into a saturated sodium bicarbonate solution (300 mL), subjected to extraction twice with ethyl acetate (300 mL and 200 mL), and dried over anhydrous sodium sulfate. The solvent was evaporated under reduced pressure, and the residue was purified by silica gel column chromatography (silica gel: 80 g, hexane/ethyl acetate=2/1 to 1/2 (v/v)) to give compound 6 (4.02 g, 7.97 mmol, 79.7%) as a pale yellow amorphous solid.

1H NMR (600 MHz, $CDCl_3$) δ: 8.45 (s, 1H), 7.37-7.29 (m, 9H), 7.26-7.22 (m, 2H), 6.28 (d, J=4.8 Hz, 1H), 5.26 (dd, J=6.0, 4.8 Hz, 1H), 4.67 (d, J=11.7 Hz, 1H), 4.62 (d, J=11.7 Hz, 1H), 4.50 (d, J=11.3 Hz, 1H), 4.46 (d, J=11.3 Hz, 1H), 4.40 (d, J=6.0 Hz, 1H), 3.85 (d, J=10.6 Hz, 1H), 3.62 (d, J=10.6 Hz, 1H), 2.68 (s, 1H), 2.11 (s, 3H), 1.54 (d, J=1.2 Hz, 3H)

(2) Synthesis of Compound 7

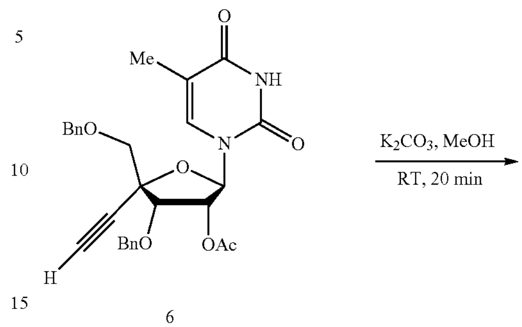

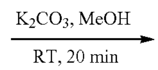

6

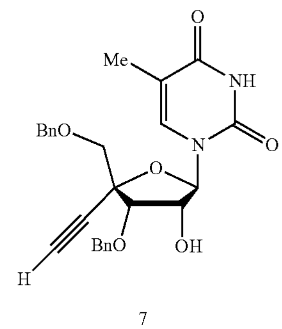

7

Potassium carbonate (821 mg, 5.94 mmol, 3.0 eq.) was added to a solution of compound 6 (1.0 g, 2.0 mmol) in methanol (10 mL), and the mixture was stirred at room temperature for 20 minutes. Tap water (10 mL) and ethyl acetate (10 mL) were added, and the mixture was subjected to extraction with ethyl acetate (60 mL). The organic layer was washed with a mixture of tap water (30 mL) and a saturated brine solution (a small amount) and then with a saturated brine solution (10 mL), dried over anhydrous sodium sulfate, and concentrated under reduced pressure to give compound 7 (0.83 g, 1.8 mmol, 91%) as a white solid.

1H NMR (600 MHz, $CDCl_3$) δ: 7.40-7.25 (m, 11H), 6.07 (d, J=5.3 Hz, 1H), 4.90 (d, J=11.4 Hz, 1H), 4.68 (d, J=11.4 Hz, 1H), 4.56 (d, J=12.0 Hz, 1H), 4.55 (d, J=12.0 Hz, 1H), 4.29 (dd, J=5.9, 5.3 Hz, 1H), 4.23 (d, J=5.9 Hz, 1H), 3.86 (d, J=10.6 Hz, 1H), 3.70 (d, J=10.6 Hz, 1H), 2.71 (s, 1H), 1.59 (d, J=0.9 Hz, 3H)

(3) Synthesis of Compound 8

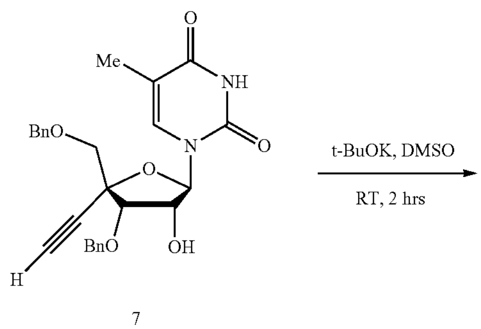

7

-continued

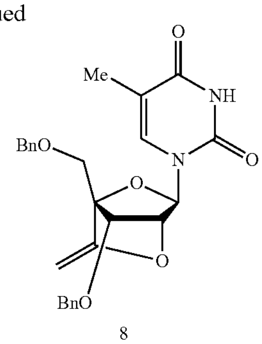

8

Potassium tert-butoxide (303 mg, 2.70 mmol, 2.5 eq.) was added to a solution of compound 7 (500 mg, 1.08 mmol) in anhydrous dimethyl sulfoxide (10 mL) under nitrogen atmosphere, and the mixture was stirred at room temperature for 2 hours. A saturated aqueous ammonium chloride solution (100 mL) was added, and the mixture was subjected to extraction with ethyl acetate (100 mL). The organic layer was washed twice with tap water (50 mL) and once with a saturated brine solution (50 mL), dried over anhydrous sodium sulfate, and concentrated under reduced pressure to give a crude product of compound 8 (435 mg) as a pale yellow amorphous solid. The resulting crude product of compound 8 was used in the subsequent step without further purification.

1H NMR (600 MHz, $CDCl_3$) δ: 9.21 (br s, 1H), 7.48 (d, J=1.2 Hz, 1H), 7.38-7.23 (m, 10H), 5.61 (s, 1H), 4.72 (s, 1H), 4.64 (d, J=10.9 Hz, 1H), 4.66 (d, J=12.0 Hz, 1H), 4.61 (d, J=10.9 Hz, 1H), 4.56 (d, J=12.0 Hz, 1H), 4.50 (d, J=3.1 Hz, 1H), 4.04 (d, J=3.1 Hz, 1H), 4.02 (s, 1H), 4.00 (d, J=11.3 Hz, 1H), 3.94 (d, J=11.3 Hz, 1H), 1.59 (d, J=1.2 Hz, 3H)

(4) Synthesis of Compound 9

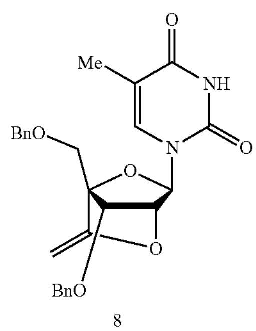

8

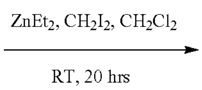

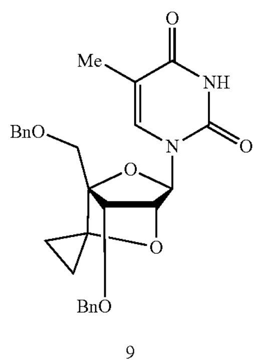

9

A solution of diiodomethane (7.73 g, 28.9 mmol, 5.0 eq.) in anhydrous dichloromethane (15 mL) was added dropwise to a solution of compound 8 (2.67 g, 5.77 mmol) in anhydrous dichloromethane (50 mL) under ice cooling under nitrogen atmosphere. The mixture was rinsed with anhydrous dichloromethane (5 mL). Diethylzinc (a 1.0M solution in hexane, 28.9 mL, 28.9 mmol, 5.0 eq.) was added dropwise over 15 minutes, and the mixture was stirred at the same temperature for 2 hours and then at room temperature for 20 hours. Then, 25 w/w % ammonia water (20 mL) and water (50 mL) were added dropwise over 5 minutes at 10° C. or lower, and the mixture was subjected to extraction twice with ethyl acetate (150 mL). The organic layer was washed with tap water and then with a saturated brine solution, dried over anhydrous sodium sulfate, and concentrated under reduced pressure. The residue was purified by silica gel column chromatography (silica gel: 60 g, chloroform/methanol=1/0 to 9/1 (v/v)) to give compound 9 (2.16 g, 4.53 mmol, 78.5%) as a yellow solid.

1H NMR (600 MHz, $CDCl_3$) δ: 8.89 (br s, 1H), 7.51 (d, J=1.2 Hz, 1H), 7.38-7.27 (m, 10H), 5.74 (s, 1H), 4.70 (d, J=11.7 Hz, 1H), 4.57 (d, J=11.7 Hz, 1H), 4.56 (s, 2H), 4.53 (s, 1H), 4.04 (s, 1H), 3.62 (d, J=10.7 Hz, 1H), 3.50 (d, J=10.7 Hz, 1H), 1.62 (d, J=1.2 Hz, 3H), 1.03-0.96 (m, 1H), 0.96-0.89 (m, 1H), 0.75-0.65 (m, 2H)

According to the conventional synthesis method as described in WO 2015/125783, compound 9 can be synthesized from compound 1 via 11 conversion steps, whereas according to the method as described in Example 1 and Example 2, conversion from compound 1 to compound 9 can be carried out via only 8 steps, resulting in reduction of the number of steps.

Example 3: Synthesis of G-Dibenzyl Derivatives (Part 1)

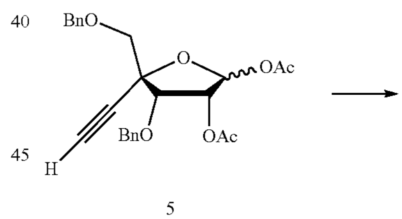

5

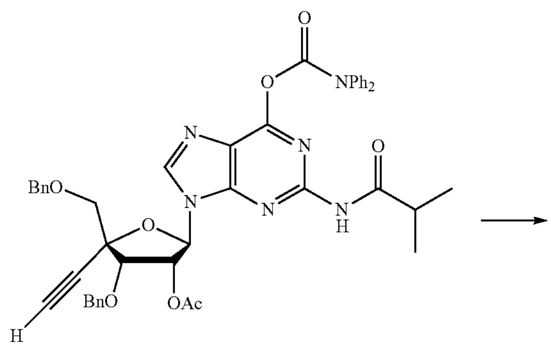

10

-continued

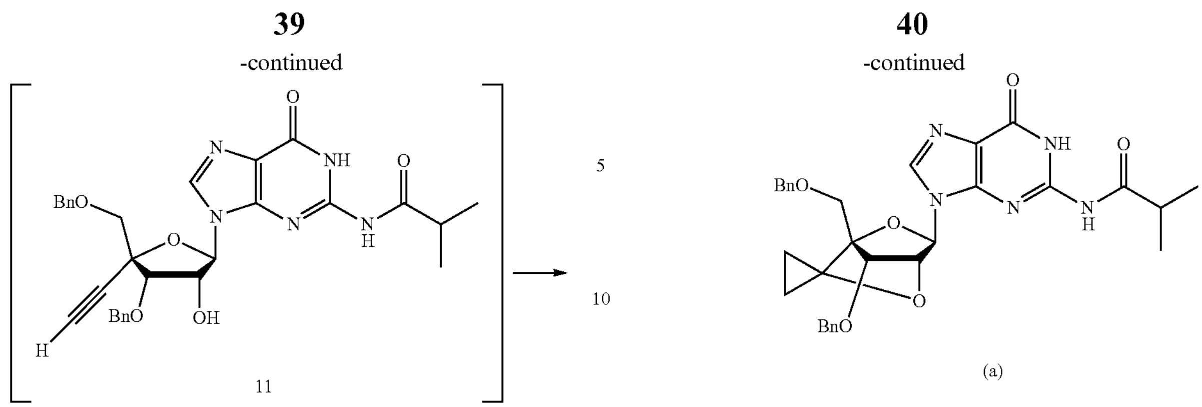

11

(a)

(1) Synthesis of Compound 10

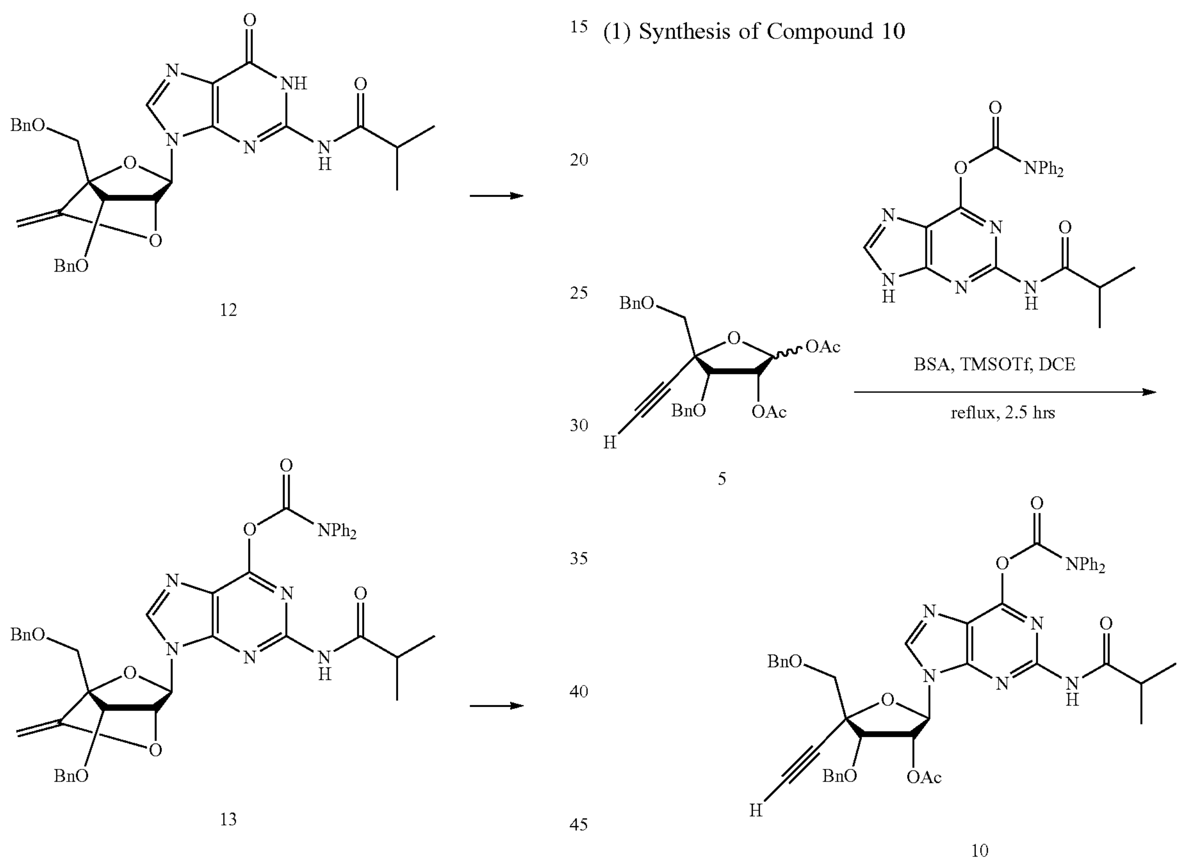

12

13

5

10

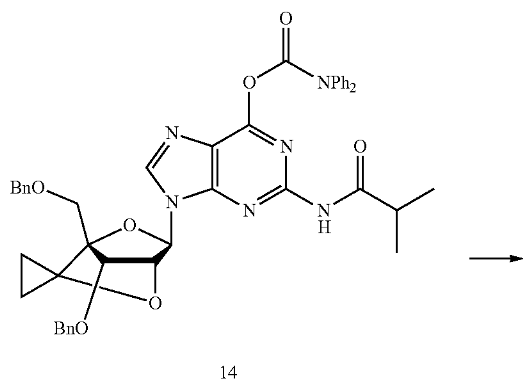

14

N,O-bis(trimethylsilyl)acetamide (1.5 mL, 8.3 mmol, 2.0 eq.) and trimethylsilyl triflate (1.8 mL, 13 mmol, 3.0 eq.) were successively added to a solution of compound 5 (1.86 g, 4.24 mmol) and O—N,N-diphenylcarbamoyl-N-isobutyrylguanine (1.94 g, 4.66 mmol, 1.1 eq.) in 1,2-dichloroethane (20 mL) under ice cooling under nitrogen atmosphere. The mixture was heated to reflux for 2.5 hours. The reaction mixture was left to cool down to room temperature and then cooled on ice, and a saturated sodium bicarbonate solution (50 mL) was poured thereinto. The mixture was subjected to extraction twice with chloroform (100 mL and 50 mL). The combined organic layers were washed with a saturated brine solution (20 mL), dried over anhydrous sodium sulfate, and concentrated under reduced pressure. The residue was purified by silica gel column chromatography (silica gel: 45 g, chloroform/ethyl acetate=1/0 to 85/15 (v/v)) to give compound 10 (1.78 g, 2.24 mmol, 52.8%) as a pale yellow amorphous solid.

1H NMR (600 MHz, $CDCl_3$) δ: 8.09 (s, 1H), 7.88 (s, 1H), 7.39-7.20 (m, 20H), 6.23 (d, J=3.8 Hz, 1H), 5.67 (dd, J=5.9, 3.8 Hz, 1H), 4.94 (d, J=5.9 Hz, 1H), 4.78 (d, J=11.7 Hz, 1H), 4.67 (d, J=11.7 Hz, 1H), 4.52 (d, J=12.1 Hz, 1H), 4.47 (d, J=12.1 Hz, 1H), 3.81 (d, J=10.9 Hz, 1H), 3.68 (d, J=10.9 Hz, 1H), 3.07-2.84 (m, 1H), 2.70 (s, 1H), 2.09 (s, 3H), 1.24 (d, J=6.8 Hz, 3H), 1.24 (d, J=6.8 Hz, 3H)

(2) Synthesis of Compound 12

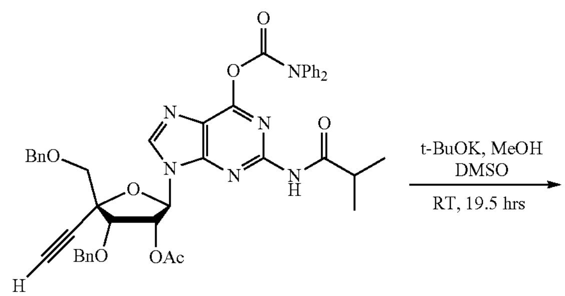

10

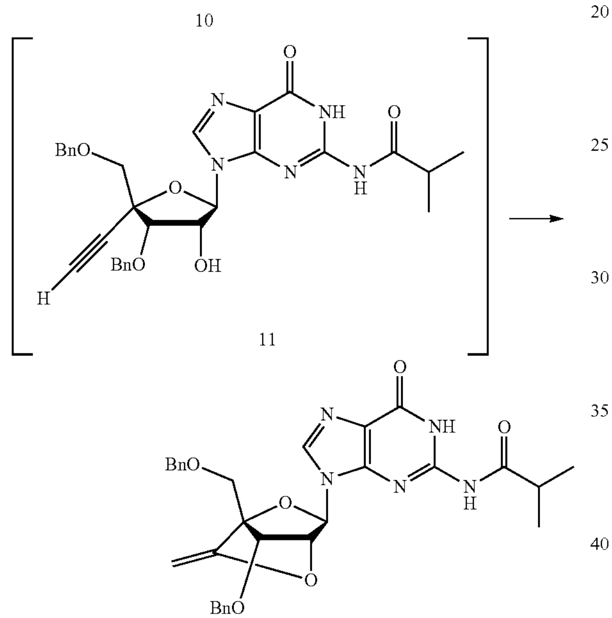

11

12

Potassium tert-butoxide (70.6 mg, 0.629 mmol, 5.0 eq.) was added to a solution of compound 10 (100 mg, 0.126 mmol) in anhydrous dimethyl sulfoxide (1 mL) under nitrogen atmosphere, and the mixture was stirred at room temperature for 30 minutes. Methanol (8.0 μL, 0.20 mmol, 1.6 eq.) was added, and the mixture was further stirred for 3 hours. Methanol (4.0 μL, 0.10 mmol, 0.8 eq.) and potassium tert-butoxide (37.5 mg, 0.334 mmol, 2.7 eq.) were added, and the mixture was further stirred for 16 hours. Ethyl acetate (10 mL) and tap water (10 mL) were added, and the mixture was subjected to extraction twice with ethyl acetate. The combined organic layers were washed twice with a 1 M aqueous hydrochloric acid solution (20 mL) and once with a saturated brine solution (20 mL), dried over anhydrous sodium sulfate, and concentrated under reduced pressure to give a mixture of compound 12 and diphenylamine (76.2 mg, purity: 72%, yield: 78%, based on the integral ratio of 1H-NMR spectra) as a pale brown amorphous solid.

1H NMR (600 MHz, $CDCl_3$) δ: 12.12 (br s, 1H), 9.48 (br s, 1H), 7.81 (s, 1H), 7.39-7.18 (m, 10H), 5.77 (s, 1H), 4.68 (d, J=12.3 Hz, 1H), 4.62 (d, J=12.3 Hz, 1H), 4.62 (s, 1H), 4.59 (d, J=11.7 Hz, 1H), 4.53 (d, J=11.7 Hz, 1H), 4.50 (d, J=2.9 Hz, 1H), 4.28 (s, 1H), 4.12 (d, J=2.9 Hz, 1H), 3.94 (d, J=11.4 Hz, 1H), 3.90 (d, J=11.4 Hz, 1H), 2.71-2.65 (m, 1H), 1.26 (d, J=6.2 Hz, 3H), 1.25 (d, J=6.2 Hz, 3H)

(3) Synthesis of Compound 13

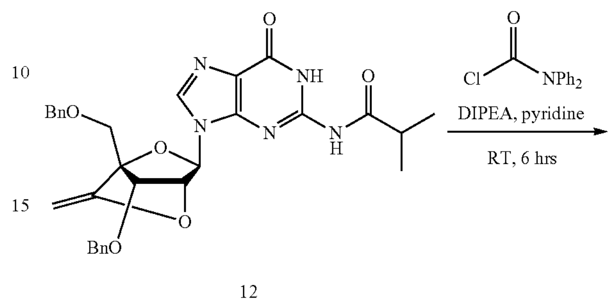

12

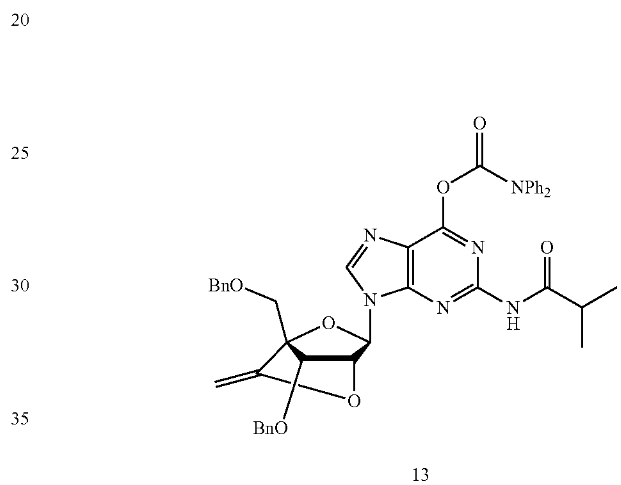

13

N,N-diisopropylethylamine (0.10 mL, 0.59 mmol, 3.0 eq.) and N,N-diphenylcarbamoyl chloride (56 mg, 0.24 mmol, 1.2 eq.) were successively added to a solution of compound 12 (110 mg, 0.197 mmol) in anhydrous pyridine (0.8 mL) under nitrogen atmosphere, and the mixture was stirred at room temperature for 6 hours. Tap water (0.1 mL) was added, and the solvent was evaporated under reduced pressure. The mixture was azeotropically distilled twice with toluene. The residue was dissolved in ethyl acetate, successively washed with a 1 M aqueous hydrochloric acid solution, a saturated sodium bicarbonate solution and a saturated brine solution, dried over anhydrous sodium sulfate, and concentrated under reduced pressure. The residue was azeotropically distilled twice with toluene to give a crude product of compound 13 (178 mg) as a red amorphous solid. The resulting compound 13 was used in the subsequent step without further purification.

1H NMR (600 MHz, $CDCl_3$) δ: 8.18 (s, 1H), 7.98 (br s, 1H), 7.50-7.14 (m, 20H), 5.95 (s, 1H), 4.97 (s, 1H), 4.67 (d, J=12.3 Hz, 1H), 4.62 (d, J=12.3 Hz, 1H), 4.59-4.55 (m, 2H), 4.52 (d, J=3.2 Hz, 1H), 4.28 (s, 1H), 4.12 (d, J=3.2 Hz, 1H), 3.94 (d, J=11.3 Hz, 1H), 3.89 (d, J=11.3 Hz, 1H), 3.06-2.90 (m, 1H), 1.26-1.24 (m, 6H)

(4) Synthesis of Compound 14

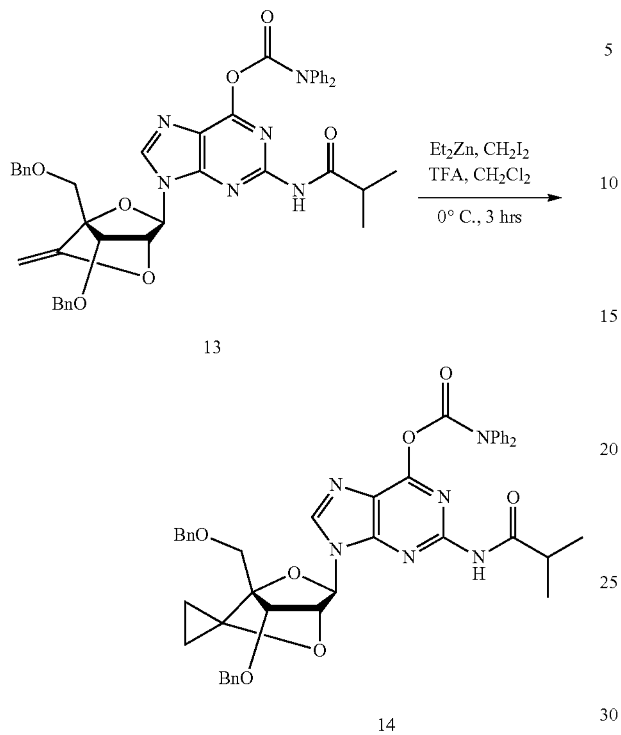

13

14

Diethylzinc (a 1 M solution in hexane, 2.0 mL, 2.0 mmol, 10 eq.) was added to anhydrous dichloromethane (3 mL) under ice cooling under nitrogen atmosphere. A solution of trifluoroacetic acid (230 mg, 2.02 mmol, 10 eq.) in anhydrous dichloromethane (1 mL) was added dropwise over 5 minutes, and the mixture was stirred at the same temperature for 30 minutes. A solution of diiodomethane (542 mg, 2.02 mmol, 10 eq.) in anhydrous dichloromethane (1 mL) was added dropwise over 5 minutes, and the mixture was further stirred at the same temperature for 30 minutes. To the solution, a solution of the crude product of compound 13 (178 mg) in anhydrous dichloromethane (0.5 mL) (and then rinsed with 0.5 mL of anhydrous dichloromethane) was added dropwise, and the mixture was stirred at the same temperature for 3 hours. A 0.5M aqueous hydrochloric acid solution (10 mL) and chloroform (15 mL) were added, and the mixture was vigorously stirred at room temperature for 1 hour. The solution was separated into an aqueous layer and an organic layer, and the aqueous layer was further subjected to extraction with chloroform. The aqueous layer was combined with the organic layer, washed with a saturated brine solution, dried over anhydrous sodium sulfate, and concentrated under reduced pressure. The residue was purified by silica gel column chromatography (silica gel: 14 g, hexane/ethyl acetate/methanol=90/5/5 to 75/20/5 (v/v/v)) to give compound 14 (86.4 mg, 0.113 mmol, 57.2%) as a reddish brown viscous liquid.

1H NMR (600 MHz, $CDCl_3$) δ: 8.19 (s, 1H), 7.97 (s, 1H), 7.51-7.20 (m, 20H), 6.10 (s, 1H), 4.78 (s, 1H), 4.62 (d, J=11.9 Hz, 1H), 4.59-4.53 (m, 1H), 4.55 (d, J=11.9 Hz, 1H), 4.30 (s, 1H), 3.64 (d, J=11.0 Hz, 1H), 3.54 (d, J=11.0 Hz, 1H), 3.08-2.95 (m, 1H), 1.25 (d, J=6.9 Hz, 3H), 1.25 (d, J=6.9 Hz, 3H), 1.01-0.91 (m, 2H), 0.88-0.83 (m, 1H), 0.76-0.70 (m, 1H)

(5) Synthesis of a Compound Represented by Formula (a)

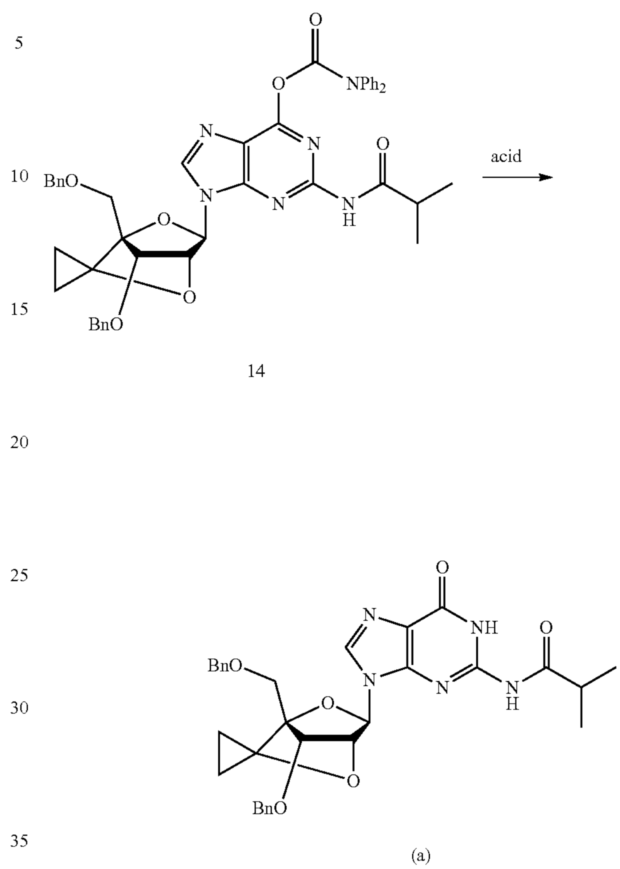

14

(a)

Compound 14 was found to be easily converted into a compound represented by formula (a) by treating compound 14 with a weak acid (e.g., carboxylic acid, etc.).

A compound represented by formula (a):

(a)

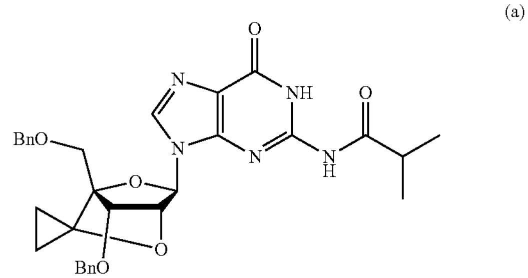 [SMILES: CC(C)C(=O)Nc1nc2c(ncn2[C@@H]2O[C@]3(COCc4ccccc4)C(OCc4ccccc4)[C@@H]2OC32CC2)c(=O)[nH]1]

can be used as a precursor of scpBNAs, as with compound 14.

According to the conventional synthesis method as described in WO 2015/125783, a compound represented by formula (a) can be synthesized from compound 1 via 12 conversion steps, whereas according to the method as described in Example 1 and Example 3, conversion from compound 1 to a compound represented by formula (a) can be carried out via only 9 steps, resulting in reduction of the number of steps.

Example 4: Synthesis of G-Benzyl Derivatives (Part 2)
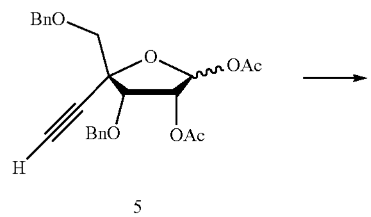
5
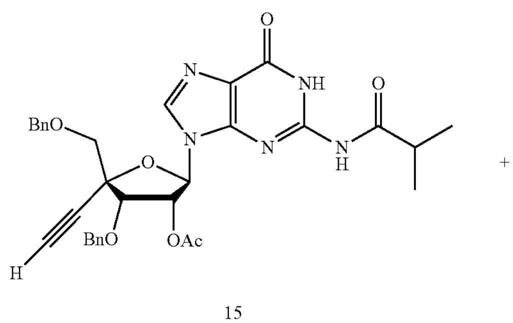
15
+
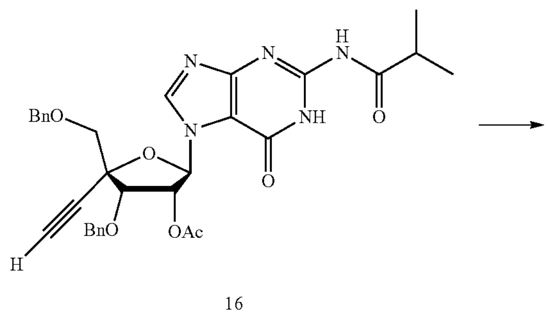
16
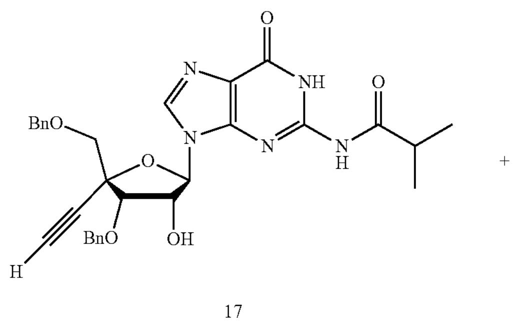
17
+
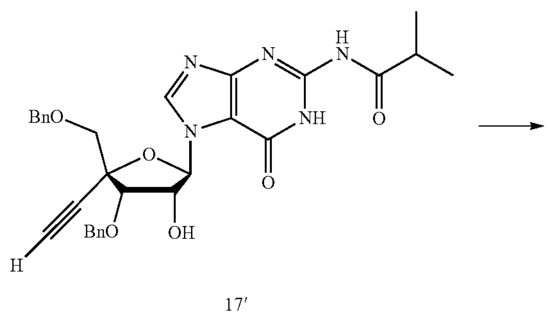
17′
-continued
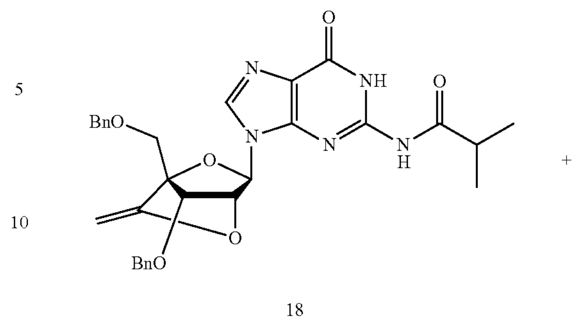
18
+
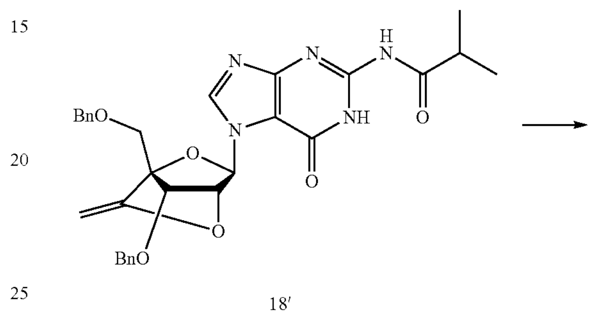
18′
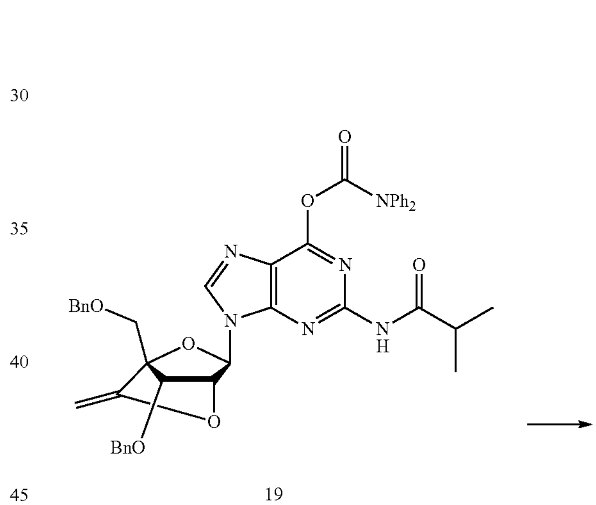
19
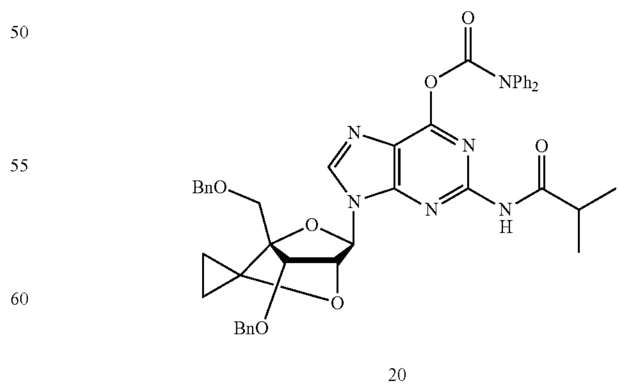
20

(1) Synthesis of Compound 15

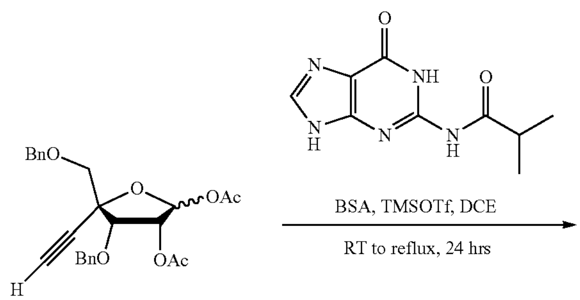

5

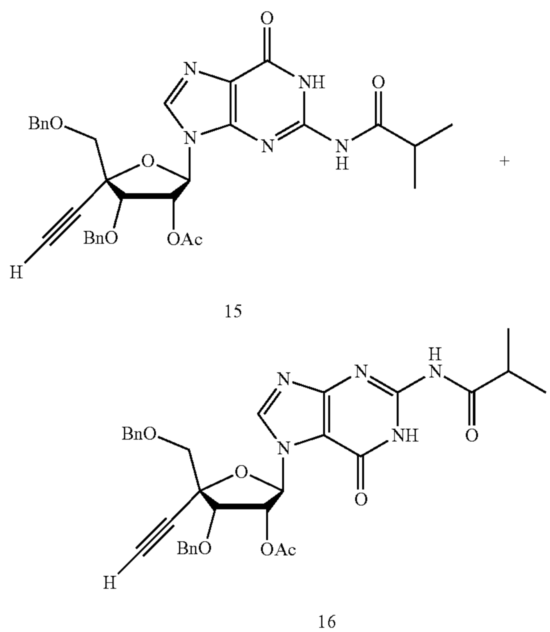

15

+

16

N-isobutyrylguanine (1.94 g, 8.77 mmol, 1.2 eq.), N,O-bis(trimethylsilyl)acetamide (3.14 mL, 21.9 mmol, 3.0 eq.) and trimethylsilyl triflate (2.64 mL, 14.6 mmol, 2.0 eq.) were successively added to a solution of compound 5 (4.0 g, purity: 80%, 7.3 mmol) in 1,2-dichloroethane (100 mL) under ice cooling under nitrogen atmosphere. The mixture was stirred at room temperature for 17 hours, then heated to 50° C. and stirred for 1 hour. N,O-bis(trimethylsilyl)acetamide (3.14 mL, 21.9 mmol, 3.0 eq.) was added, and the mixture was further stirred at the same temperature for 1 hour. The mixture was heated to reflux for 2 hours, left to cool down to room temperature, and further stirred for 3 hours. A saturated sodium bicarbonate solution (50 mL) was poured into the reaction mixture under ice cooling, and the reaction mixture was subjected to extraction three times with chloroform. The combined organic layers were dried over anhydrous sodium sulfate, and concentrated under reduced pressure. The residue was purified by silica gel column chromatography (silica gel: 60 g, hexane/ethyl acetate/chloroform/methanol=3/3/1/0 to 3/3/1/0.4 (v/v/v/v)) to give a mixture of compound 15 and compound 16 (3.00 g, compound 15:compound 16=85:15, 4.25 mmol, yield: 58%, calculated from 1H-NMR) as a pale brown amorphous solid.

1H NMR (600 MHz, $CDCl_3$) δ: 12.21 (s, 0.85H), 12.06 (s, 0.15H), 9.67 (br s, 0.15H), 8.19 (br s, 0.85H), 8.19 (s, 0.15H), 7.83 (s, 0.85H), 7.36-7.30 (m, 8H), 7.26-7.24 (m,

2H), 6.50 (d, J=3.2 Hz, 0.15H), 6.16 (d, J=5.0 Hz, 0.85H), 5.63 (dd, J=6.0, 3.2 Hz, 0.15H), 5.61 (dd, J=5.9, 5.0 Hz, 0.85H), 4.73 (d, J=11.6 Hz, 0.85H), 4.64 (d, J=11.4 Hz, 0.15H), 4.64 (d, J=5.9 Hz, 0.85H), 4.59 (d, J=11.6 Hz, 0.85H), 4.57 (d, J=6.0 Hz, 0.15H), 4.56 (d, J=11.4 Hz, 0.15H), 4.55 (d, J=11.9 Hz, 0.85H), 4.49-4.47 (m, 0.30H), 4.48 (d, J=11.9 Hz, 0.85H), 3.81 (d, J=10.9 Hz, 0.15H), 3.79 (d, J=10.9 Hz, 0.85H), 3.68 (d, J=10.9 Hz, 0.85H), 3.58 (d, J=10.9 Hz, 0.15H), 2.77 (dq, J=6.9, 6.9 Hz, 0.85H), 2.71 (s, 0.85H), 2.70 (s, 0.15H), 2.50 (dq, J=6.9, 6.9 Hz, 0.15H), 2.14 (s, 0.45H), 2.08 (s, 2.55H), 1.28 (d, J=6.9 Hz, 0.45H), 1.27 (d, J=6.9 Hz, 0.45H), 1.23 (d, J=6.9 Hz, 2.55H), 1.22 (d, J=6.9 Hz, 2.55H)

(2) Synthesis of Compound 17

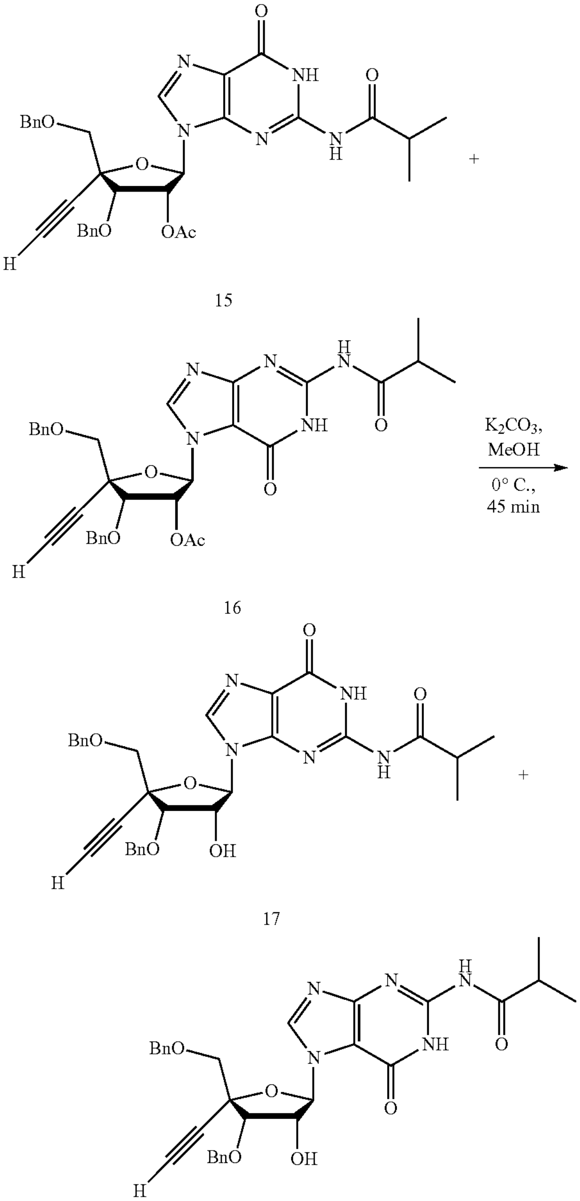

15

+

16

17

+

17′

Potassium carbonate (2.07 g, 15.0 mmol, 3.0 eq.) was added to a solution of the mixture of compound 15 and compound 16 (3.0 g, 5.0 mmol, compound 15:compound 16=85:15) in methanol (30 mL) under ice cooling, and the mixture was stirred at the same temperature for 30 minutes. Potassium carbonate (0.50 g, 3.6 mmol, 0.72 eq.) was added, and the mixture was further stirred for 15 minutes. A saturated aqueous ammonium chloride solution was added, and the mixture was subjected to extraction with ethyl acetate. The organic layer was successively washed with tap water and a saturated brine solution, and dried over anhydrous sodium sulfate. The solvent was evaporated under reduced pressure, and the residue was purified by silica gel column chromatography (silica gel: 30 g, chloroform/ethyl acetate=1/0 to 4/1 (v/v)) to give a mixture of compound 17 and compound 17' (2.41 g, compound 17:compound 17'=85:15, 4.32 mmol, yield: 86%) as a white amorphous solid.

1H NMR (600 MHz, $CDCl_3$) δ: 12.50 (br s, 0.15H), 12.25 (br s, 0.85H), 9.82 (br s, 0.15H), 8.99 (br s, 0.85H), 8.12 (s, 0.85H), 7.88 (s, 0.15H), 7.42-7.21 (m, 10H), 6.31 (d, J=4.4 Hz, 0.85H), 6.02 (d, J=4.7 Hz, 0.15H), 4.91 (d, J=11.4 Hz, 0.15H), 4.82 (d, J=11.4 Hz, 0.85H), 4.78 (d, J=11.4 Hz, 0.15H), 4.70 (d, J=11.4 Hz, 0.85H), 4.65-4.62 (m, 0.15H), 4.59 (d, J=12.0 Hz, 0.85H), 4.55 (d, J=12.0 Hz, 0.15H), 4.55 (d, J=12.0 Hz, 0.85H), 4.55-4.53 (m, 0.15H), 4.54 (ddd, J=6.6, 6.2, 4.4 Hz, 0.85H), 4.49 (d, J=12.0 Hz, 0.15H), 4.40 (d, J=6.2 Hz, 0.85H), 3.87-3.85 (m, 0.15H), 3.85 (d, J=10.4 Hz, 0.85H), 3.78 (d, J=10.9 Hz, 0.15H), 3.71 (d, J=10.9 Hz, 0.15H), 3.69 (d, J=10.4 Hz, 0.85H), 3.52 (d, J=6.6 Hz, 0.85H), 2.81 (dq, J=6.9, 6.9 Hz, 0.85H), 2.74 (s, 0.85H), 2.73 (s, 0.15H), 2.62 (dq, J=6.9, 6.9 Hz, 0.15H), 1.26 (d, J=6.9 Hz, 2.55H), 1.26 (d, J=6.9 Hz, 2.55H), 1.22 (d, J=6.9 Hz, 0.45H), 1.22 (d, J=6.9 Hz, 0.45H)

(3) Synthesis of Compound 18

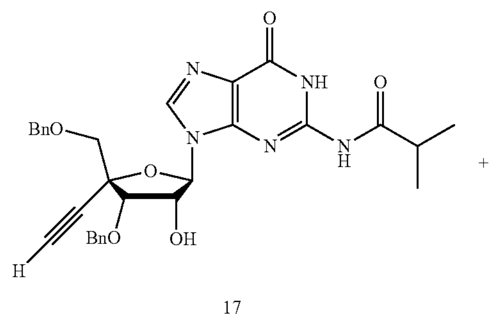

17

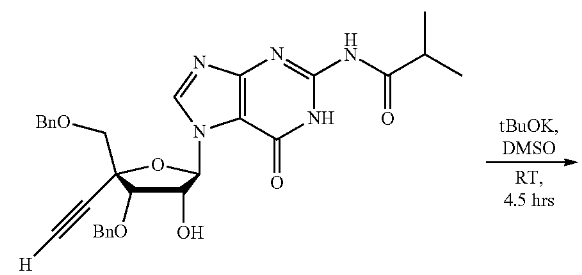

17'

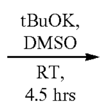

-continued

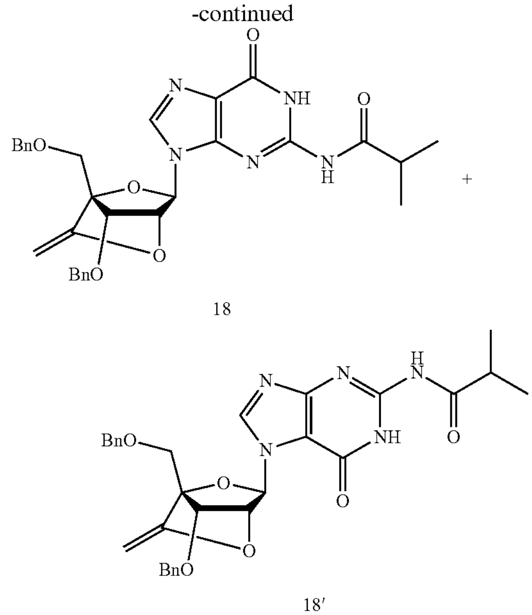

18

18'

Potassium tert-butoxide (302 mg, 2.69 mmol, 1.5 eq.) was added to a solution of the mixture of compound 17 and compound 17' (1.00 g, 1.79 mmol, compound 17:compound 17'=85:15) in anhydrous dimethyl sulfoxide (20 mL) under nitrogen atmosphere, and the mixture was stirred at room temperature for 1 hour. Potassium tert-butoxide (150 mg, 1.34 mmol, 0.75 eq.) was added, and the mixture was stirred for 30 minutes. Potassium tert-butoxide (273 mg, 2.43 mmol, 1.4 eq.) was further added, and the mixture was further stirred for 3 hours. Ethyl acetate (150 mL) and tap water (50 mL) were added under ice cooling, and the mixture was subjected to extraction twice with ethyl acetate. The combined organic layers were washed twice with tap water and then once with a saturated brine solution, dried over anhydrous sodium sulfate, and concentrated under reduced pressure to give a crude product of a mixture of compound 18 and compound 18' (904 mg, compound 18:compound 18'=85:15) as a pale brown amorphous solid.

1H NMR (600 MHz, $CDCl_3$) δ: 12.29 (br s, 0.85H), 12.12 (br s, 0.15H), 9.96 (br s, 0.15H), 8.85 (br s, 0.85H), 8.20 (s, 0.15H), 7.82 (s, 0.85H), 7.37-7.16 (m, 10H), 6.15 (s, 0.15H), 5.75 (s, 0.85H), 4.71-4.47 (m, 6H), 4.26 (s, 0.85H), 4.18 (s, 0.15H), 4.11 (d, J=3.23 Hz, 0.85H), 4.06 (d, J=3.23, 0.15H), 3.96 (d, J=10.9 Hz, 0.15H), 3.93 (d, J=11.2 Hz, 0.85H), 3.90 (d, J=10.9 Hz, 0.15H), 3.89 (d, J=11.2 Hz, 0.85H), 2.78 (dq, J=6.9, 6.9 Hz, 0.15H), 2.67 (dq, J=6.9, 6.9 Hz, 0.85H), 1.28 (d, J=6.9 Hz, 2.55H), 1.27 (d, J=6.9 Hz, 0.45H), 1.27 (d, J=6.9 Hz, 2.55H), 1.25 (d, J=6.9 Hz, 0.45H)

(4) Synthesis of Compound 19

Synthesis was performed under the same conditions as those in step (3) of Example 3.

(5) Synthesis of Compound 20

Synthesis was performed under the same conditions as those in step (4) of Example 3.

As with Example 3, the synthetic process of this Example revealed that scpBNAs having a compound with a guanine skeleton introduced thereinto can be obtained, regardless of use of a protecting group.

Example 5: Synthesis of A-Benzyl Derivatives (Part 1)

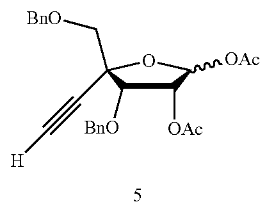

5

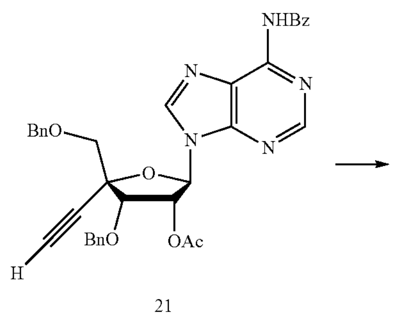

21

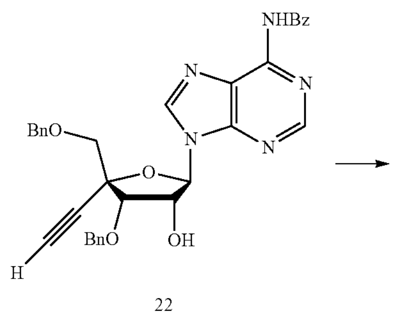

22

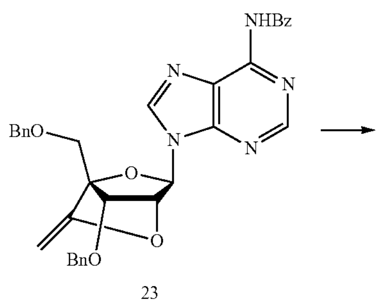

23

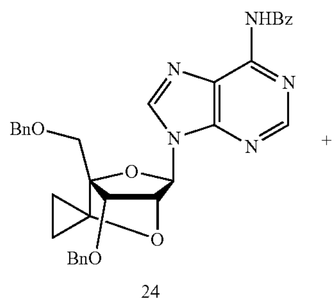

24

+

-continued

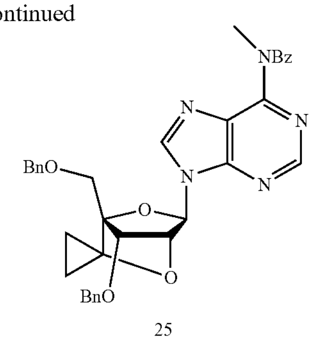

25

(1) Synthesis of Compound 21

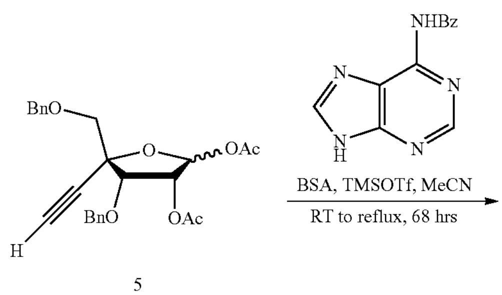

5

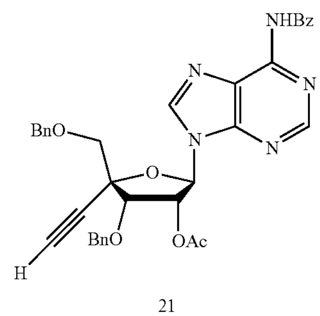

21

$N^6$-benzoyladenine (1.60 g, 6.69 mmol, 1.1 eq.) was added to a solution of compound 5 (3.32 g, purity: 80%, 6.08 mmol) in acetonitrile (80 mL) under nitrogen atmosphere. N,O-bis(trimethylsilyl)acetamide (2.61 mL, 18.2 mmol, 3.0 eq.) and trimethylsilyl triflate (1.65 mL, 9.12 mmol, 1.5 eq.) were successively added under ice cooling, and the mixture was stirred at room temperature for 18 hours. The mixture was heated to reflux for 5.5 hours, left to cool down, and stirred at room temperature for 18 hours. The mixture was heated to reflux for 6 hours, left to cool down again to room temperature, and stirred at room temperature for 20 hours. A saturated sodium bicarbonate solution was added under ice cooling, and the mixture was subjected to extraction with ethyl acetate. The organic layer was successively washed with tap water and a saturated brine solution, dried over anhydrous sodium sulfate, and concentrated under reduced pressure. The residue was purified by silica gel column chromatography (silica gel: 60 g, chloroform/ethyl acetate=1/0 to 6/4 (v/v)) to give compound 21 (3.11 g, 5.04 mmol, yield: 82.8%) as a pale brown amorphous solid.

1H NMR (600 MHz, $CDCl_3$) δ: 8.95 (s, 1H), 8.74 (s, 1H), 8.21 (s, 1H), 8.04-8.00 (m, 2H), 7.64-7.59 (m, 1H), 7.56-7.51 (m, 2H), 7.38-7.27 (m, 8H), 7.23-7.19 (m, 2H), 6.40 (d, J=4.1 Hz, 1H), 5.82 (dd, J=5.6, 4.1 Hz, 1H), 4.76 (d, J=5.6 Hz, 1H), 4.72 (d, J=11.7 Hz, 1H), 4.66 (d, J=11.7 Hz, 1H), 4.49 (d, J=12.0 Hz, 1H), 4.44 (d, J=12.0 Hz, 1H), 3.81 (d, J=10.9 Hz, 1H), 3.63 (d, J=10.9 Hz, 1H), 2.72 (s, 1H), 2.11 (s, 3H)

(2) Synthesis of Compound 22

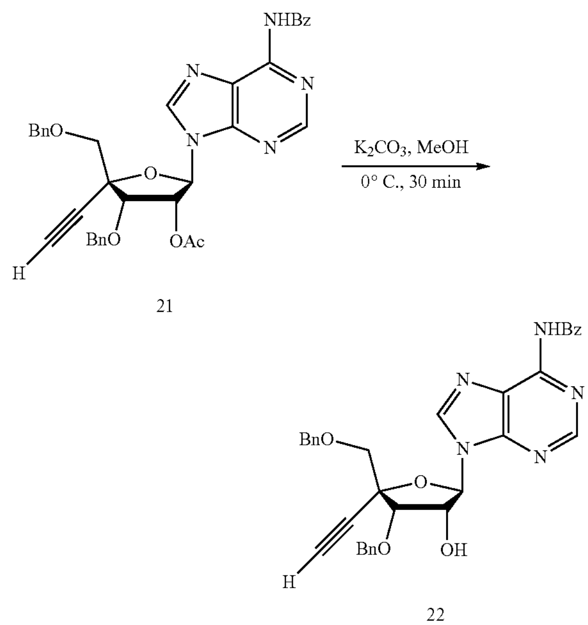

21

22

Potassium carbonate (1.00 g, 7.24 mmol, 3.0 eq.) was added to a solution of compound 21 (1.50 g, 2.43 mmol) in methanol (20 mL) under ice cooling, and the mixture was stirred at the same temperature for 30 minutes. A saturated aqueous ammonium chloride solution was added, and the mixture was subjected to extraction twice with ethyl acetate. The combined organic layers were washed with a saturated brine solution, and dried over anhydrous sodium sulfate. The solvent was evaporated under reduced pressure to give a crude product of compound 22 (1.50 g) as a pale orange amorphous solid. The resulting compound 22 was directly used in the subsequent step without further purification.

1H NMR (600 MHz, $CDCl_3$) δ: 8.91 (s, 1H), 8.74 (s, 1H), 8.19 (s, 1H), 8.03-8.00 (m, 2H), 7.64-7.60 (m, 1H), 7.56-7.51 (m, 2H), 7.43-7.29 (m, 8H), 7.25-7.22 (m, 2H), 6.23 (d, J=4.4 Hz, 1H), 4.92 (d, J=11.4 Hz, 1H), 4.81 (ddd, J=6.7, 5.9, 4.4 Hz, 1H), 4.72 (d, J=11.4 Hz, 1H), 4.60 (d, J=5.9 Hz, 1H), 4.56 (d, J=12.0 Hz, 1H), 4.51 (d, J=12.0 Hz, 1H), 3.83 (d, J=10.6 Hz, 1H), 3.70 (d, J=10.6 Hz, 1H), 3.33 (d, J=6.7 Hz, 1H), 2.76 (s, 1H)

(3) Synthesis of Compound 23

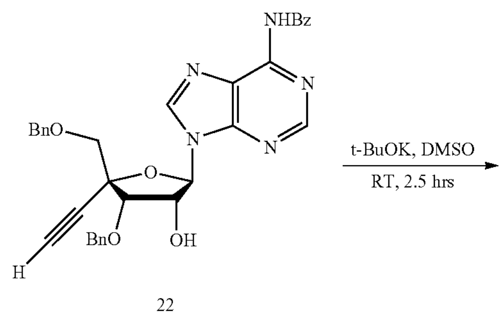

22

-continued

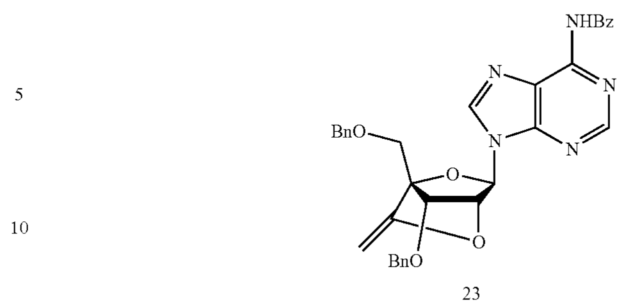

23

Potassium tert-butoxide (545 mg, 4.85 mmol, 2.0 eq.) was added to a solution of the crude product of compound 22 (1.50 g) of the previous step in anhydrous dimethyl sulfoxide (30 mL) under nitrogen atmosphere, and the mixture was stirred at room temperature for 2.5 hours. A saturated aqueous ammonium chloride solution and ethyl acetate were added, and the mixture was subjected to extraction twice with ethyl acetate. The combined organic layers were successively washed with tap water and a saturated brine solution, and dried over anhydrous sodium sulfate. The solvent was evaporated under reduced pressure. The residue was purified through a silica gel pad ($NH_2$ silica gel, hexane/ethyl acetate/methanol=8/8/1) to give compound 23 (1.18 g, 2.05 mmol, yield in two steps: 84.4%) as a brown viscous liquid.

1H NMR (600 MHz, $CDCl_3$) δ: 9.04 (s, 1H), 8.75 (s, 1H), 8.26 (s, 1H), 8.04 (d, J=7.5 Hz, 2H), 7.63 (t, J=7.6 Hz, 1H), 7.54 (dd, J=7.6, 7.5 Hz, 2H), 7.41-7.28 (m, 6H), 7.26-7.17 (m, 4H), 6.06 (s, 1H), 4.98 (s, 1H), 4.69 (d, J=12.2 Hz, 1H), 4.64 (d, J=12.2 Hz, 1H), 4.61 (d, J=12.0 Hz, 1H), 4.58 (d, J=12.0 Hz, 1H), 4.56 (d, J=3.2 Hz, 1H), 4.36 (s, 1H), 4.15 (d, J=3.2 Hz, 1H), 3.98 (d, J=11.2 Hz, 1H), 3.92 (d, J=11.2 Hz, 1H)

(4) Synthesis of Compound 24

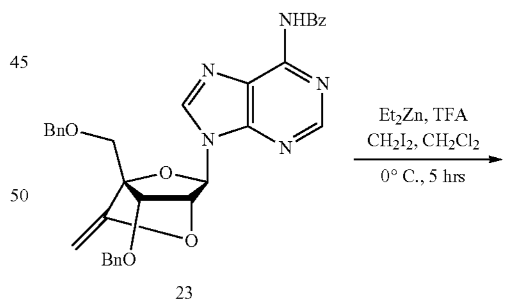

23

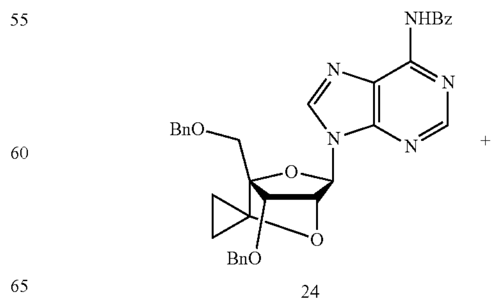

24

-continued

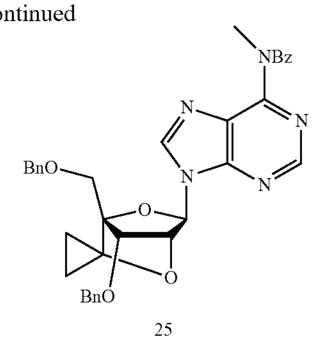

25

Diethylzinc (a 1 M solution in hexane, 2.4 mL, 2.4 mmol, 10 eq.) was added to anhydrous dichloromethane (2.8 mL) under ice cooling under nitrogen atmosphere. A solution of trifluoroacetic acid (274 mg, 2.40 mmol, 10 eq.) in anhydrous dichloromethane (1 mL) was added dropwise over 5 minutes, and the mixture was stirred at the same temperature for 30 minutes. A solution of diiodomethane (643 mg, 2.40 mmol, 10 eq.) in anhydrous dichloromethane (1 mL) was added dropwise over 5 minutes, and the mixture was further stirred at the same temperature for 30 minutes to give a zinc carbenoid solution. The zinc carbenoid solution (720 μL) was added dropwise to a solution of compound 23 (138 mg, 0.240 mmol) in anhydrous dichloromethane (2.0 mL) under ice cooling under nitrogen atmosphere. The mixture was stirred at the same temperature for 1.5 hours, and the zinc carbenoid solution (720 μL) was further added dropwise. The mixture was further stirred for 1 hour, and the zinc carbenoid solution (720 μL) was added dropwise. At 30 and 75 minutes after further stirring of the mixture, the zinc carbenoid solution (1.5 mL each) was further added dropwise, and the mixture was stirred for 1.5 hours. A saturated aqueous ammonium chloride solution and chloroform were added, and the mixture was vigorously stirred at room temperature for 30 minutes. The resulting solution was separated into an aqueous layer and an organic layer, and the aqueous layer was further subjected to extraction with chloroform. The combined organic layers were washed with a saturated brine solution, and dried over anhydrous sodium sulfate. The solvent was evaporated under reduced pressure to give a residue. The ratio of compound 24 and compound 25 in the residue was 3:1 (calculated from LC/MS and 1H-NMR).

Example 6: Synthesis of A-Dibenzyl Derivatives (Part 2)

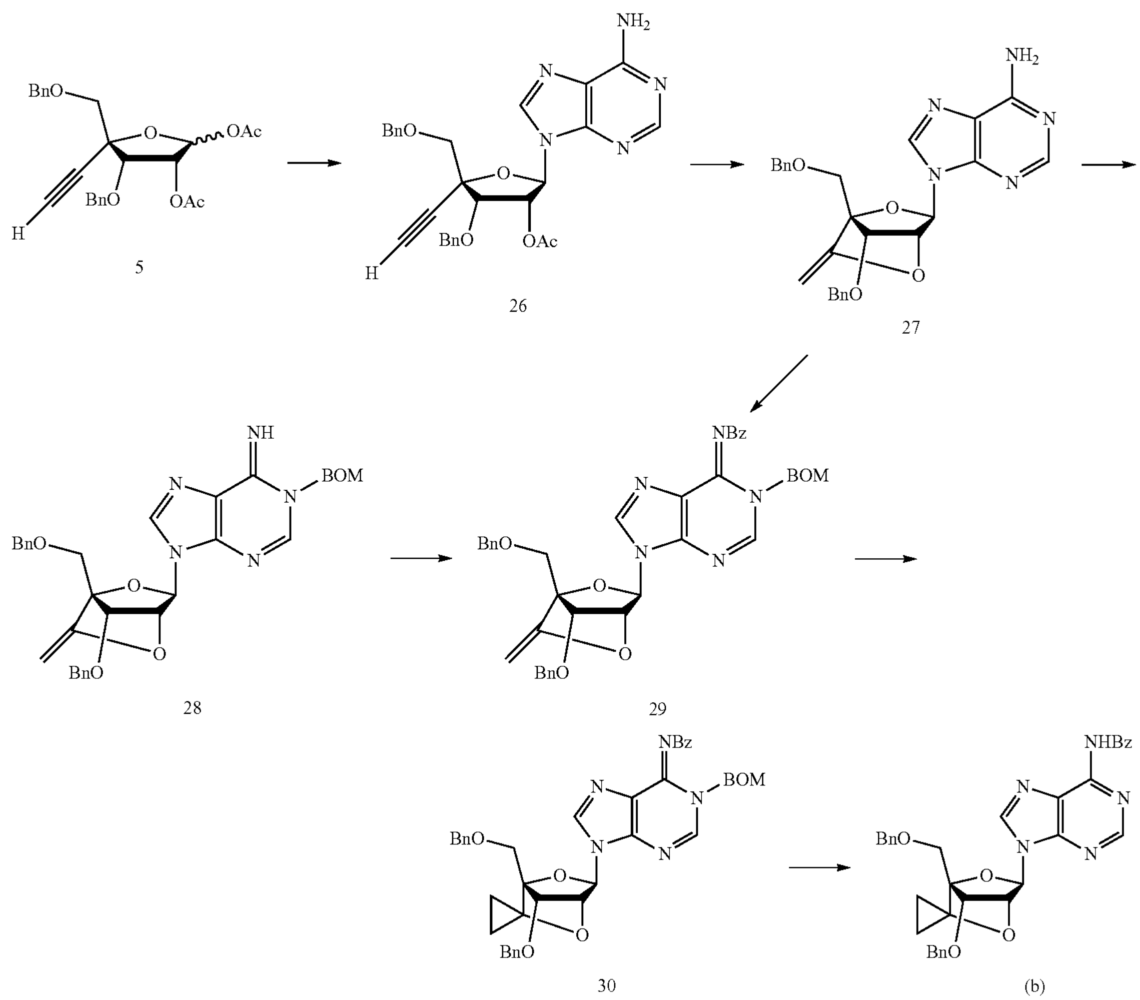

5 26 27 28 29 30 (b)

(1) Synthesis of Compound 26

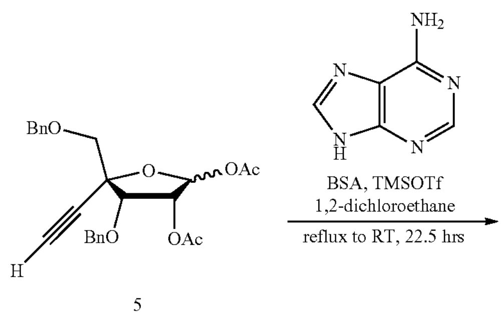

5

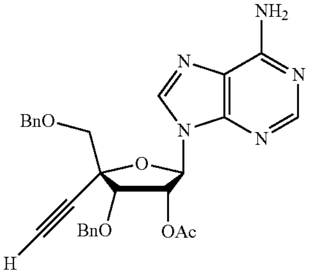

26

Chlorotrimethylsilane (11 mL, 87.1 mmol, 29 eq.) was added to a solution of adenine (1.01 g, 7.47 mmol, 2.5 eq.) in bis(trimethylsilyl)amine (25 mL) under nitrogen atmosphere, and the mixture was heated to reflux for 5 hours. The mixture was left to cool down, and concentrated under reduced pressure. The residue was dissolved in 1,2-dichloroethane (5 mL) under nitrogen atmosphere, and a solution of compound 5 (1.32 g, 3.00 mmol) in dichloroethane (10 mL) was added. Trimethylsilyl triflate (2.70 mL, 14.9 mmol, 5.0 eq.) was added, and the mixture was stirred at room temperature for 17.5 hours. A saturated sodium bicarbonate solution (200 mL) was added, and the mixture was subjected to extraction twice with ethyl acetate (200 mL). The organic layer was washed with a saturated brine solution, dried over anhydrous sodium sulfate, and concentrated under reduced pressure. The residue was purified by silica gel column chromatography (silica gel: 60 g, hexane/ethyl acetate/methanol=75/20/5 to 45/50/5 (v/v/v)) to give compound 26 (1.32 g, 2.57 mmol, yield: 85.7%) as a white waxy solid.

1H NMR (600 MHz, $CDCl_3$) δ: 8.29 (s, 1H), 7.96 (s, 1H), 7.38-7.27 (m, 8H), 7.24-7.20 (m, 2H), 6.32 (d, J=4.1 Hz, 1H), 5.79 (dd, J=5.9, 4.1 Hz, 1H), 5.74 (br s, 2H), 4.76 (d, J=5.9 Hz, 1H), 4.70 (d, J=11.7 Hz, 1H), 4.65 (d, J=11.7 Hz, 1H), 4.50 (d, J=12.0 Hz, 1H), 4.44 (d, J=12.0 Hz, 1H), 3.80 (d, J=10.7 Hz, 1H), 3.63 (d, J=10.7 Hz, 1H), 2.71 (s, 1H), 2.10 (s, 3H)

(2) Synthesis of Compound 27

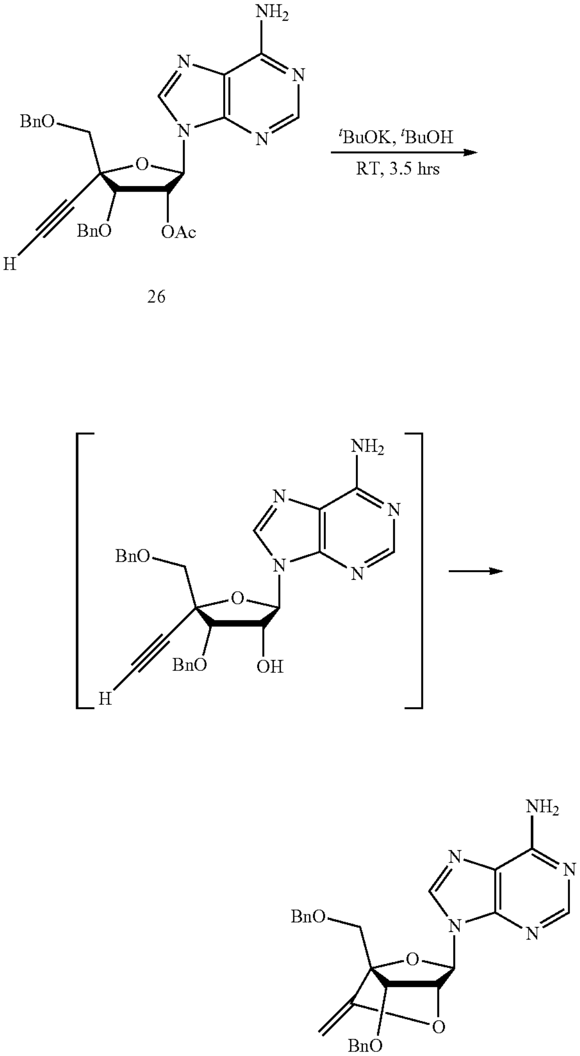

26

27

Potassium tert-butoxide (432 mg, 3.85 mmol, 5.0 eq.) was added to a solution of compound 26 (395 mg, 0.769 mmol) in tert-butyl alcohol (4 mL), and the mixture was stirred at room temperature for 1.5 hours. Potassium tert-butoxide (480 mg, 4.28 mmol, 5.6 eq.) was added, and the mixture was stirred for 1 hour. Potassium tert-butoxide (300 mg, 2.67 mmol, 3.5 eq.) was added, and the mixture was further stirred for 1 hour. Tap water (6 mL) and a saturated brine solution (12 mL) were added, and the mixture was subjected to extraction twice with ethyl acetate. The combined organic layers were washed with a saturated brine solution, and dried over anhydrous sodium sulfate. The solvent was evaporated under reduced pressure to give a crude product of compound 27 (315 mg) as an orange amorphous solid. The crude product of compound 27 was used in the subsequent step without further purification.

1H NMR (600 MHz, $CDCl_3$) δ: 8.31 (s, 1H), 8.00 (s, 1H), 7.30-7.22 (m, 10H), 5.99 (s, 1H), 5.78 (br s, 2H), 4.97 (s, 1H), 4.69 (d, J=12.2 Hz, 1H), 4.63 (d, J=12.2 Hz, 1H), 4.59 (s, 2H), 4.54 (d, J=2.9 Hz, 1H), 4.35 (s, 1H), 4.14 (d, J=2.9 Hz, 1H), 3.97 (d, J=11.3 Hz, 1H), 3.92 (d, J=11.3 Hz, 1H)

(3) Synthesis of Compound 28

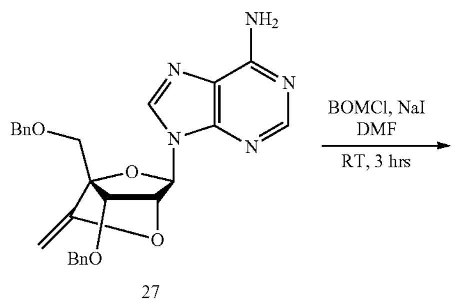

27

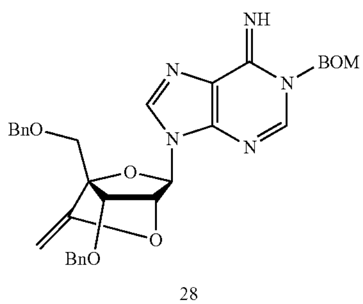

28

Sodium iodide (318 mg, 2.12 mmol, 10 eq.) was added to a solution of compound 27 (100 mg, 0.212 mmol) in N,N-dimethylformamide (2 mL) under nitrogen atmosphere. Benzylchloromethyl ether (300 μL, 2.16 mmol, 10 eq.) was added under ice cooling, and the mixture was stirred at room temperature for 3 hours. A saturated sodium bicarbonate solution (6 mL) and tap water (12 mL) were added, and the mixture was subjected to extraction twice with ethyl acetate. The combined organic layers were successively washed with a 15 w/w % aqueous sodium thiosulfate solution and a saturated brine solution, and dried over anhydrous sodium sulfate. The solvent was evaporated under reduced pressure to give a crude product of compound 28 (390 mg) as an orange oily liquid. The crude product of compound 28 was used in the subsequent step without further purification.

(4) Synthesis of Compound 29

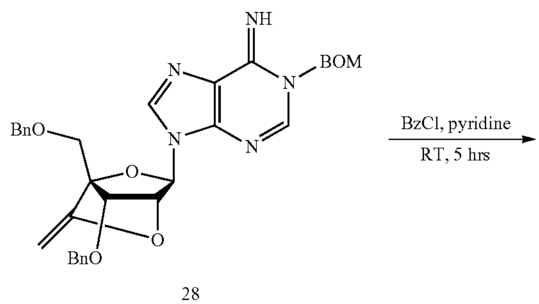

28

-continued

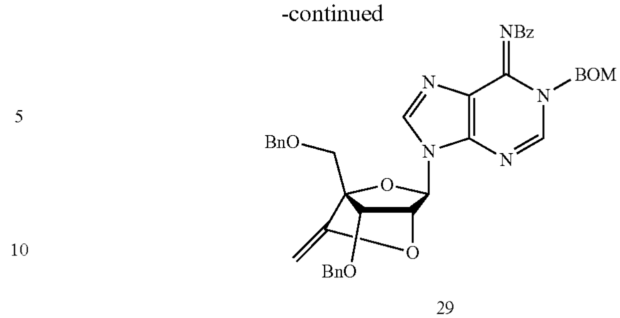

29

Benzoyl chloride (120 μL, 1.03 mmol, 4.9 eq.) was added to a solution of the crude product of compound 28 (390 mg) of the previous step in pyridine (3 mL) under nitrogen atmosphere, and the mixture was stirred at room temperature for 5 hours. Tap water (20 mL) was added, and the mixture was subjected to extraction twice with ethyl acetate. The combined organic layers were successively washed with a 1 M aqueous hydrochloric acid solution, tap water and a saturated brine solution, and dried over anhydrous sodium sulfate. The solvent was evaporated under reduced pressure. The residue was purified by silica gel column chromatography ($NH_2$ silica gel: 20 g, hexane/ethyl acetate/methanol=85/10/5 to 70/25/5 (v/v/v)) to give compound 29 (60.5 mg, 0.0870 mol, yield: 41.0%) as a pale yellow oily liquid.

1H NMR (600 MHz, $CDCl_3$) δ: 8.18-8.15 (m, 2H), 8.02 (s, 1H), 7.98 (s, 1H), 7.53-7.49 (m, 1H), 7.44-7.18 (m, 17H), 5.89 (s, 1H), 5.72 (d, J=10.7 Hz, 1H), 5.70 (d, J=10.7 Hz, 1H), 4.82 (d, J=12.0 Hz, 1H), 4.84 (d, J=12.0 Hz, 1H), 4.74 (s, 1H), 4.63 (d, J=12.6 Hz, 1H), 4.58 (d, J=12.6 Hz, 1H), 4.56 (d, J=12.0 Hz, 1H), 4.52 (d, J=12.0 Hz, 1H), 4.51 (d, J=3.1 Hz, 1H), 4.29 (s, 1H), 4.08 (d, J=3.1 Hz, 1H), 3.88 (d, J=11.2 Hz, 1H), 3.83 (d, J=11.2 Hz, 1H)

(5) Synthesis of Compound 29

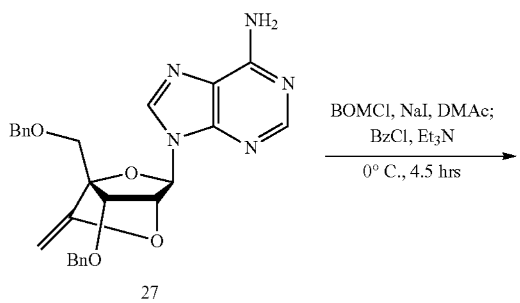

27

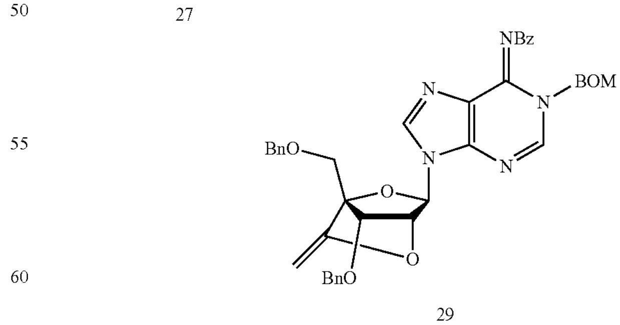

29

Sodium iodide (241 mg, 1.61 mmol, 2.2 eq.) was added to a solution of compound 27 (345 mg, 0.732 mmol) in N,N-dimethylacetamide (1.5 mL) under nitrogen atmosphere. Benzylchloromethyl ether (250 μL, 1.80 mmol, 2.5 eq.) was added under ice cooling, and the mixture was stirred at the same temperature for 2 hours. Benzylchloromethyl ether (35 μL, 0.25 mmol, 0.34 eq.) was added at the same temperature, and the mixture was further stirred for 1.5 hours. Triethylamine (2.0 mL, 14.4 mmol, 20 eq.) and benzoyl chloride (400 μL, 3.44 mmol, 4.7 eq.) were added at the same temperature, and the mixture was stirred for 2 hours. Ethyl acetate (30 mL) and tap water (10 mL) were added, and the mixture was stirred and separated into an organic layer and an aqueous layer. The organic layer was successively washed with a 15 w/w % aqueous sodium thiosulfate solution, tap water and saturated brine solution, and dried over anhydrous sodium sulfate. The solvent was evaporated under reduced pressure. The residue was purified by silica gel column chromatography ($NH_2$ silica gel: 30 g, hexane/ethyl acetate/methanol=90/5/5 to 85/10/5 (v/v/v)) to give compound 29 (462.6 mg, purity: 70%, 0.465 mmol, yield: 63.6%) as a pale yellow oily liquid.

(6) Synthesis of Compound 30

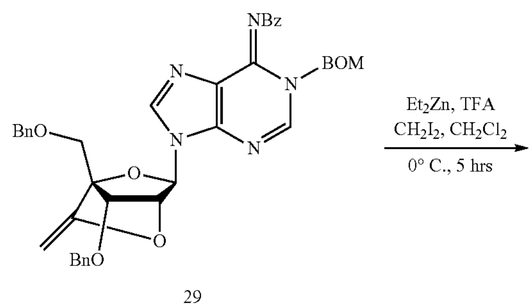

29

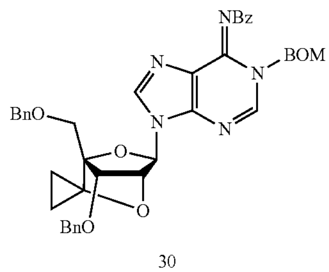

30

Diethylzinc (a 1 M solution in hexane, 0.25 mL, 0.25 mmol, 7.0 eq.) was added to anhydrous dichloromethane (0.25 mL) under ice cooling under nitrogen atmosphere. A solution of trifluoroacetic acid (30.0 mg, 0.263 mmol, 7.3 eq.) in anhydrous dichloromethane (0.25 mL) was added dropwise over 1 minute. The mixture was stirred at the same temperature for 30 minutes. A solution of diiodomethane (67.4 mg, 0.259 mmol, 7.0 eq.) in anhydrous dichloromethane (0.25 mL) was added dropwise over 1 minute, and the mixture was further stirred at the same temperature for 30 minutes to give a zinc carbenoid solution. To the solution, a solution of compound 29 (25.0 mg, 0.0359 mmol) in anhydrous dichloromethane (0.5 mL) (and then rinsed with 0.5 mL of anhydrous dichloromethane) was added dropwise, and the mixture was stirred at the same temperature for 4.5 hours. A saturated aqueous ammonium chloride solution (20 mL) and chloroform (20 mL) were added, and the mixture was vigorously stirred at room temperature for 30 minutes. The resulting solution was separated into an aqueous layer and an organic layer, and the aqueous layer was further subjected to extraction with chloroform. The combined organic layers were washed with a saturated brine solution, and dried over anhydrous sodium sulfate. The solvent was evaporated under reduced pressure. The residue was purified by silica gel column chromatography (silica gel: 10 g, hexane/ethyl acetate/methanol=80/15/5 (v/v/v)) to give compound 30 (20.0 mg, 0.0282 mmol, yield: 78.5%) as a pale yellow oily liquid.

1H NMR (600 MHz, $CDCl_3$) δ: 8.19-8.15 (m, 2H), 8.03 (s, 1H), 7.97 (s, 1H), 7.52-7.48 (m, 1H), 7.44-7.21 (m, 17H), 6.04 (s, 1H), 5.72 (d, J=10.3 Hz, 1H), 5.70 (d, J=10.3 Hz, 1H), 4.84 (d, J=12.0 Hz, 1H), 4.82 (d, J=12.0 Hz, 1H), 4.59-4.52 (m, 4H), 4.52 (s, 1H), 4.27 (s, 1H), 3.54 (d, J=11.2 Hz, 1H), 3.47 (d, J=11.2 Hz, 1H), 1.02-0.65 (m, 4H)

(7) Synthesis of a Compound Represented by Formula (b)

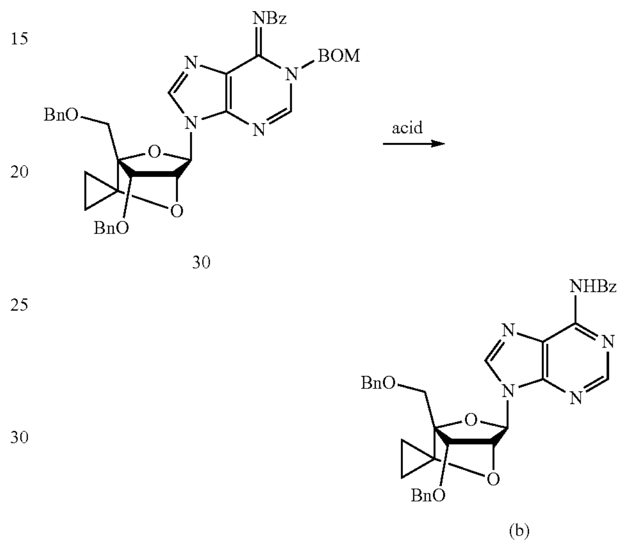

30

(b)

Compound 30 was found to be easily converted into a compound represented by formula (b) by treating compound 30 with a weak acid (carboxylic acid, silica gel, etc.).

As with compound 30, a compound represented by formula (b) below can be used as a precursor of scpBNAs.

(b)

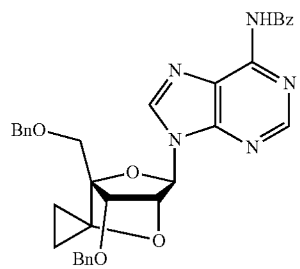

According to the conventional synthesis method as described in WO 2015/125783, a compound represented by formula (b) can be synthesized from compound 1 via 12 conversion steps, whereas according to the method as described in Example 1 and Example 6, conversion from compound 1 to a compound represented by formula (b) can be carried out via only 9 steps, resulting in reduction of the number of steps.

INDUSTRIAL APPLICABILITY

The present invention enables efficient production of spirocyclopropylene bridged nucleic acids (scpBNAs), and is suitable for use in the field of nucleic acid medicines.

The invention claimed is:

1. A method for producing a compound represented by formula (II):

(II)

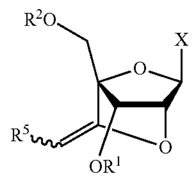

wherein X, $R^1$, $R^2$ and $R^5$ are as defined below, the method comprising at least intramolecularly cyclizing a compound represented by formula (I):

(I)

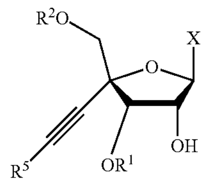

wherein

X represents a nucleic acid base moiety optionally having one or more substituents selected from a group α consisting of a hydroxy group, a hydroxy group protected by a protecting group for nucleic acid synthesis, an alkyl group of 1 to 5 carbon atoms, an alkoxy group of 1 to 5 carbon atoms, a mercapto group, a mercapto group protected by a protecting group for nucleic acid synthesis, an alkylthio group of 1 to 5 carbon atoms, an amino group, an amino group protected by a protecting group for nucleic acid synthesis, an amino group substituted with an alkyl group of 1 to 5 carbon atoms, and a halogen atom;

$R^1$ and $R^2$ each independently represent a hydrogen atom, a protecting group for a hydroxy group used in nucleic acid synthesis, an optionally branched or cyclic alkyl group of 1 to 7 carbon atoms, an optionally branched or cyclic alkenyl group of 2 to 7 carbon atoms, an aryl group of 3 to 10 carbon atoms optionally having one or more substituents selected from the group α and optionally containing a heteroatom, an aralkyl group having an aryl moiety of 3 to 12 carbon atoms optionally having one or more substituents selected from the group α and optionally containing a heteroatom, an acyl group optionally having one or more substituents selected from the group α, a silyl group optionally having one or more substituents selected from the group α, a phosphate group optionally having one or more substituents selected from the group α, a phosphate group protected by a protecting group for nucleic acid synthesis, or —$P(R^3)R^4$ (wherein $R^3$ and $R^4$ each independently represent a hydroxy group, a hydroxy group protected by a protecting group for nucleic acid synthesis, a mercapto group, a mercapto group protected by a protecting group for nucleic acid synthesis, an amino group, an alkoxy group of 1 to 5 carbon atoms, an alkylthio group of 1 to 5 carbon atoms, a cyanoalkoxy group of 1 to 6 carbon atoms, or an amino group substituted with an alkyl group of 1 to 6 carbon atoms); and $R^5$ represents a hydrogen atom, a halogen atom, an optionally branched or cyclic alkyl group of 1 to 7 carbon atoms optionally substituted with an aryl group of 3 to 12 carbon atoms optionally containing a heteroatom, an aralkyl group having an aryl moiety of 3 to 12 carbon atoms optionally containing a heteroatom, or a silyl group.

2. The production method according to claim 1, wherein the intramolecular cyclization is performed in the presence of a base.

3. The production method according to claim 2, wherein the base is an alkoxide.

4. The production method according to claim 1, further comprising producing a compound represented by formula (I) by deprotecting $R^6$ of a compound represented by formula (IV):

(IV)

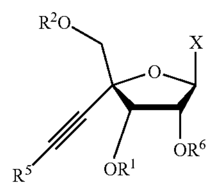

wherein

X represents a nucleic acid base moiety optionally having one or more substituents selected from a group α consisting of a hydroxy group, a hydroxy group protected by a protecting group for nucleic acid synthesis, an alkyl group of 1 to 5 carbon atoms, an alkoxy group of 1 to 5 carbon atoms, a mercapto group, a mercapto group protected by a protecting group for nucleic acid synthesis, an alkylthio group of 1 to 5 carbon atoms, an amino group, an amino group protected by a protecting group for nucleic acid synthesis, an amino group substituted with an alkyl group of 1 to 5 carbon atoms, and a halogen atom;

$R^1$ and $R^2$ each independently represent a hydrogen atom, a protecting group for a hydroxy group used in nucleic acid synthesis, an optionally branched or cyclic alkyl group of 1 to 7 carbon atoms, an optionally branched or cyclic alkenyl group of 2 to 7 carbon atoms, an aryl group of 3 to 10 carbon atoms optionally having one or more substituents selected from the group α and optionally containing a heteroatom, an aralkyl group having an aryl moiety of 3 to 12 carbon atoms optionally having one or more substituents selected from the group α and optionally containing a heteroatom, an acyl group optionally having one or more substituents selected from the group α, a silyl group optionally having one or more substituents selected from the group α, a phosphate group optionally having one or more substituents selected from the group α, a phosphate group protected by a protecting group for nucleic acid synthesis, or —$P(R^3)$ $R^4$ (wherein $R^3$ and $R^4$ each independently represent a hydroxy group, a hydroxy group protected by a protecting group for nucleic acid synthesis, a mercapto group, a mercapto group protected by a protecting group for nucleic acid synthesis, an amino group, an alkoxy group of 1 to 5 carbon atoms, an alkylthio group of 1 to 5 carbon atoms, a cyanoalkoxy group of 1 to 6 carbon atoms, or an amino group substituted with an alkyl group of 1 to 6 carbon atoms);

$R^5$ represents a hydrogen atom, a halogen atom, an optionally branched or cyclic alkyl group of 1 to 7 carbon atoms optionally substituted with an aryl group of 3 to 12 carbon atoms optionally containing a heteroatom, an aralkyl group having an aryl moiety of 3 to 12 carbon atoms optionally containing a heteroatom, or a silyl group; and $R^6$ represents a protecting group for a hydroxy group used in nucleic acid synthesis.

5. The production method according to claim 4, wherein $R^6$ is an acetyl group.

6. The production method according to claim 1, further comprising producing a compound represented by formula (I) using, as a starting material, a compound represented by formula (V):

(V)

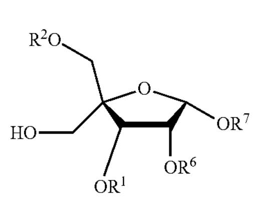

wherein $R^1$ and $R^2$ each independently represent a hydrogen atom, a protecting group for a hydroxy group used in nucleic acid synthesis, an optionally branched or cyclic alkyl group of 1 to 7 carbon atoms, an optionally branched or cyclic alkenyl group of 2 to 7 carbon atoms, an aryl group of 3 to 10 carbon atoms optionally having one or more substituents selected from a group α and optionally containing a heteroatom (wherein the group α consists of a hydroxy group, a hydroxy group protected by a protecting group for nucleic acid synthesis, an alkyl group of 1 to 5 carbon atoms, an alkoxy group of 1 to 5 carbon atoms, a mercapto group, a mercapto group protected by a protecting group for nucleic acid synthesis, an alkylthio group of 1 to 5 carbon atoms, an amino group, an amino group protected by a protecting group for nucleic acid synthesis, an amino group substituted with an alkyl group of 1 to 5 carbon atoms, and a halogen atom), an aralkyl group having an aryl moiety of 3 to 12 carbon atoms optionally having one or more substituents selected from the group α and optionally containing a heteroatom, an acyl group optionally having one or more substituents selected from the group α, a silyl group optionally having one or more substituents selected from the group α, a phosphate group optionally having one or more substituents selected from the group α, a phosphate group protected by a protecting group for nucleic acid synthesis, or $-P(R^3)R^4$ (wherein $R^3$ and $R^4$ each independently represent a hydroxy group, a hydroxy group protected by a protecting group for nucleic acid synthesis, a mercapto group, a mercapto group protected by a protecting group for nucleic acid synthesis, an amino group, an alkoxy group of 1 to 5 carbon atoms, an alkylthio group of 1 to 5 carbon atoms, a cyanoalkoxy group of 1 to 6 carbon atoms, or an amino group substituted with an alkyl group of 1 to 6 carbon atoms); and $R^6$ and $R^7$ each independently represent a protecting group for a hydroxy group used in nucleic acid synthesis, an optionally branched or cyclic alkyl group of 1 to 7 carbon atoms, an optionally branched or cyclic alkenyl group of 2 to 7 carbon atoms, an aryl group of 3 to 10 carbon atoms optionally having one or more substituents selected from the group α and optionally containing a heteroatom, an aralkyl group having an aryl moiety of 3 to 12 carbon atoms optionally having one or more substituents selected from the group α and optionally containing a heteroatom, an acyl group optionally having one or more substituents selected from the group α, a silyl group optionally having one or more substituents selected from the group α, a phosphate group optionally having one or more substituents selected from the group α, or a phosphate group protected by a protecting group for nucleic acid synthesis, or $R^6$ and $R^7$ are joined together to form-$C(R^8)(R^9)$-(wherein $R^8$ and $R^9$ each independently represent a hydrogen atom, an optionally branched or cyclic alkyl group of 1 to 7 carbon atoms optionally substituted with an aryl group of 3 to 12 carbon atoms optionally containing a heteroatom, or an aralkyl group having an aryl moiety of 3 to 12 carbon atoms optionally containing a heteroatom).

7. The production method according to claim 6, wherein $R^1$ and $R^2$ are benzyl groups.

8. A method for producing a compound represented by formula (III):

(III)

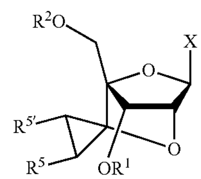

wherein X, $R^1$, $R^2$ and $R^5$ are as defined below, and $R^{5'}$ is independently as defined for $R^5$, the method comprising at least intramolecularly cyclizing a compound represented by formula (I):

(I)

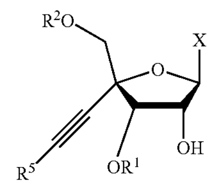

wherein

X represents a nucleic acid base moiety optionally having one or more substituents selected from a group α consisting of a hydroxy group, a hydroxy group protected by a protecting group for nucleic acid synthesis, an alkyl group of 1 to 5 carbon atoms, an alkoxy group of 1 to 5 carbon atoms, a mercapto group, a mercapto group protected by a protecting group for nucleic acid synthesis, an alkylthio group of 1 to 5 carbon atoms, an amino group, an amino group protected by a protecting group for nucleic acid synthesis, an amino group substituted with an alkyl group of 1 to 5 carbon atoms, and a halogen atom;

$R^1$ and $R^2$ each independently represent a hydrogen atom, a protecting group for a hydroxy group used in nucleic acid synthesis, an optionally branched or cyclic alkyl group of 1 to 7 carbon atoms, an optionally branched or cyclic alkenyl group of 2 to 7 carbon atoms, an aryl group of 3 to 10 carbon atoms optionally having one or more substituents selected from the group α and optionally containing a heteroatom, an aralkyl group having an aryl moiety of 3 to 12 carbon atoms optionally having one or more substituents selected from the group α and optionally containing a heteroatom, an acyl group optionally having one or more substituents selected from the group α, a silyl group optionally having one or more substituents selected from the group α, a phosphate group optionally having one or more substituents selected from the group α, a phosphate group protected by a protecting group for nucleic acid synthesis, or —$P(R^3)R^4$ (wherein $R^3$ and $R^4$ each independently represent a hydroxy group, a hydroxy group protected by a protecting group for nucleic acid synthesis, a mercapto group, a mercapto group protected by a protecting group for nucleic acid synthesis, an amino group, an alkoxy group of 1 to 5 carbon atoms, an alkylthio group of 1 to 5 carbon atoms, a cyanoalkoxy group of 1 to 6 carbon atoms, or an amino group substituted with an alkyl group of 1 to 6 carbon atoms); and $R^5$ represents a hydrogen atom, a halogen atom, an optionally branched or cyclic alkyl group of 1 to 7 carbon atoms optionally substituted with an aryl group of 3 to 12 carbon atoms optionally containing a heteroatom, an aralkyl group having an aryl moiety of 3 to 12 carbon atoms optionally containing a heteroatom, or a silyl group, to produce a compound represented by formula (II):

(II)

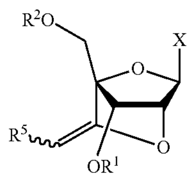

wherein X, $R^1$, $R^2$ and $R^5$ are as defined above, and cyclopropanating the compound represented by formula (II).

9. The production method according to claim 8, further comprising producing a compound represented by formula (I) by deprotecting $R^6$ of a compound represented by formula (IV):

(IV)

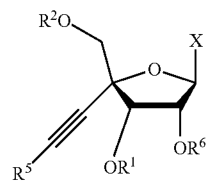

wherein

X represents a nucleic acid base moiety optionally having one or more substituents selected from a group α consisting of a hydroxy group, a hydroxy group protected by a protecting group for nucleic acid synthesis, an alkyl group of 1 to 5 carbon atoms, an alkoxy group of 1 to 5 carbon atoms, a mercapto group, a mercapto group protected by a protecting group for nucleic acid synthesis, an alkylthio group of 1 to 5 carbon atoms, an amino group, an amino group protected by a protecting group for nucleic acid synthesis, an amino group substituted with an alkyl group of 1 to 5 carbon atoms, and a halogen atom;

$R^1$ and $R^2$ each independently represent a hydrogen atom, a protecting group for a hydroxy group used in nucleic acid synthesis, an optionally branched or cyclic alkyl group of 1 to 7 carbon atoms, an optionally branched or cyclic alkenyl group of 2 to 7 carbon atoms, an aryl group of 3 to 10 carbon atoms optionally having one or more substituents selected from the group α and optionally containing a heteroatom, an aralkyl group having an aryl moiety of 3 to 12 carbon atoms optionally having one or more substituents selected from the group α and optionally containing a heteroatom, an acyl group optionally having one or more substituents selected from the group α, a silyl group optionally having one or more substituents selected from the group α, a phosphate group optionally having one or more substituents selected from the group α, a phosphate group protected by a protecting group for nucleic acid synthesis, or —$P(R^3)R^4$ (wherein $R^3$ and $R^4$ each independently represent a hydroxy group, a hydroxy group protected by a protecting group for nucleic acid synthesis, a mercapto group, a mercapto group protected by a protecting group for nucleic acid synthesis, an amino group, an alkoxy group of 1 to 5 carbon atoms, an alkylthio group of 1 to 5 carbon atoms, a cyanoalkoxy group of 1 to 6 carbon atoms, or an amino group substituted with an alkyl group of 1 to 6 carbon atoms);

$R^5$ represents a hydrogen atom, a halogen atom, an optionally branched or cyclic alkyl group of 1 to 7 carbon atoms optionally substituted with an aryl group of 3 to 12 carbon atoms optionally containing a heteroatom, an aralkyl group having an aryl moiety of 3 to 12 carbon atoms optionally containing a heteroatom, or a silyl group; and $R^6$ represents a protecting group for a hydroxy group used in nucleic acid synthesis.

10. The production method according to claim 8, wherein the intramolecular cyclization is performed in the presence of a base.

11. The production method according to claim 8, wherein the cyclopropanation comprises post-treatment of a reaction mixture with ammonia.

12. The production method according to claim 1, wherein X is a purine or pyrimidine base optionally having one or more substituents selected from the above-mentioned group α.

13. The production method according to claim 1, wherein X is a group having a uracil skeleton optionally having a substituent, a group having a cytosine skeleton optionally having a substituent, or a group having a purine skeleton optionally having a substituent.

14. The production method according to claim 8, wherein X is a purine or pyrimidine base optionally having one or more substituents selected from the above-mentioned group α.

15. The production method according to claim 8, wherein X is a group having a uracil skeleton optionally having a substituent, a group having a cytosine skeleton optionally having a substituent, or a group having a purine skeleton optionally having a substituent.

* * * * *